United States Patent
Loew et al.

(10) Patent No.: US 9,453,795 B1
(45) Date of Patent: Sep. 27, 2016

(54) METHOD AND RELATED SYSTEMS FOR MAPPING HIGH RANGES OF TOTAL PHOSPHATE CONTENT IN WATER USING MEASUREMENTS OF REFLECTED LIGHT OF OFF SURFACE WATER

(71) Applicant: BOWLING GREEN STATE UNIVERSITY, Bowling Green, OH (US)

(72) Inventors: Teagan Loew, Bowling Green, OH (US); Robert K. Vincent, Bowling Green, OH (US)

(73) Assignee: Bowling Green State University, Bowling Green, OH (US)

( * ) Notice: Subject to any disclaimer, the term of this patent is extended or adjusted under 35 U.S.C. 154(b) by 366 days.

(21) Appl. No.: 13/773,574

(22) Filed: Feb. 21, 2013

Related U.S. Application Data

(60) Provisional application No. 61/601,267, filed on Feb. 21, 2012.

(51) Int. Cl.
*G01N 21/55* (2014.01)
*G01N 21/27* (2006.01)

(52) U.S. Cl.
CPC .............. *G01N 21/55* (2013.01); *G01N 21/27* (2013.01)

(58) Field of Classification Search
USPC ................. 356/445, 448, 410, 432–444, 249
See application file for complete search history.

(56) References Cited

U.S. PATENT DOCUMENTS

2003/0112446 A1* 6/2003 Miller et al. ................. 356/504

\* cited by examiner

*Primary Examiner* — Tri T Ton
(74) *Attorney, Agent, or Firm* — Marshall & Melhorn, LLC

(57) ABSTRACT

The present invention relates to a method for determining the amount of total phosphate in a body of water from reflected light, and also includes systems for the measurement, calculation and transmission of data relating to or carrying out that method. In addition, the invention relates to methods and systems for determining other parameters of water quality from reflected light, for example, turbidity, dissolved oxygen and/or nitrogen.

42 Claims, 76 Drawing Sheets
(74 of 76 Drawing Sheet(s) Filed in Color)

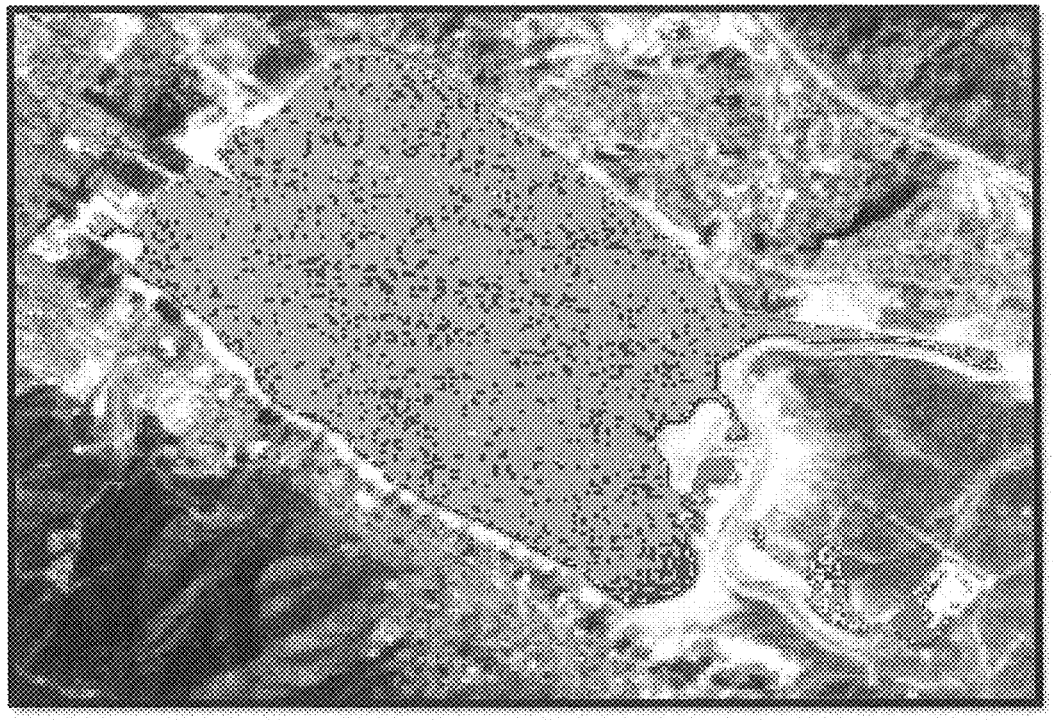
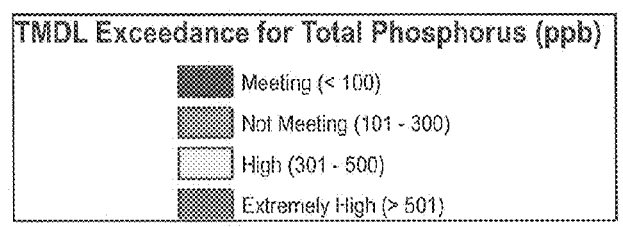
Figure 41

Appendix A: Processed Images for Satellite Passover Dates

Natural Color Image of Lake Elsinore with Stations for Reference

Appendix B: Site Visit Photos
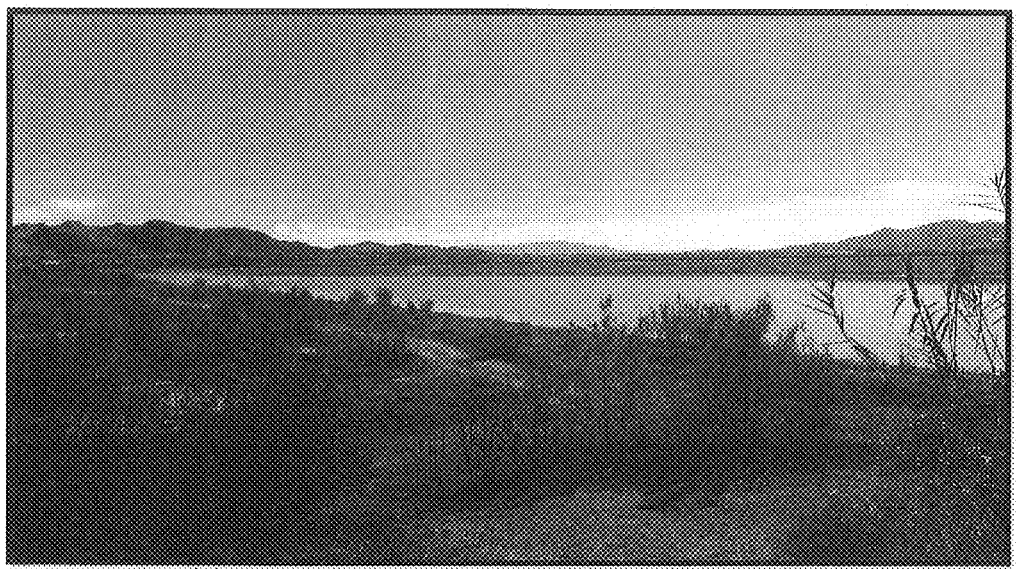
FIG. 60  Photo taken of the inlet channel on the eastern side of the lake, leading to the main body of Elsinore.
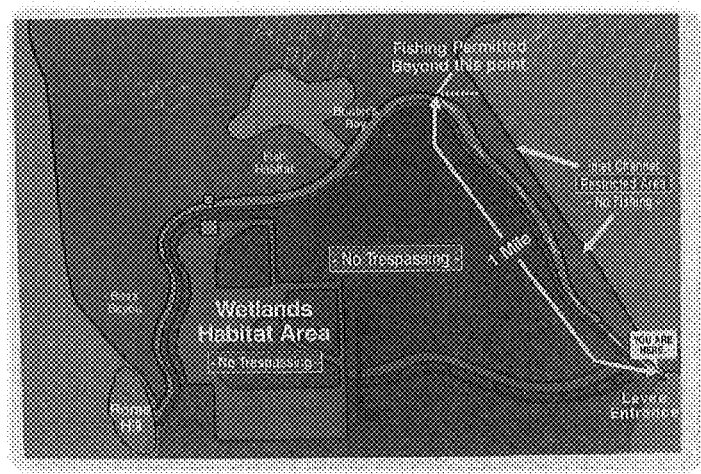
FIG. 61  Sign titled "Lake Elsinore Levee System Fishing & Wildlife Viewing Area," found at the entrance of the levee walk. Note the "fish habitat" and "wetlands habitat area."

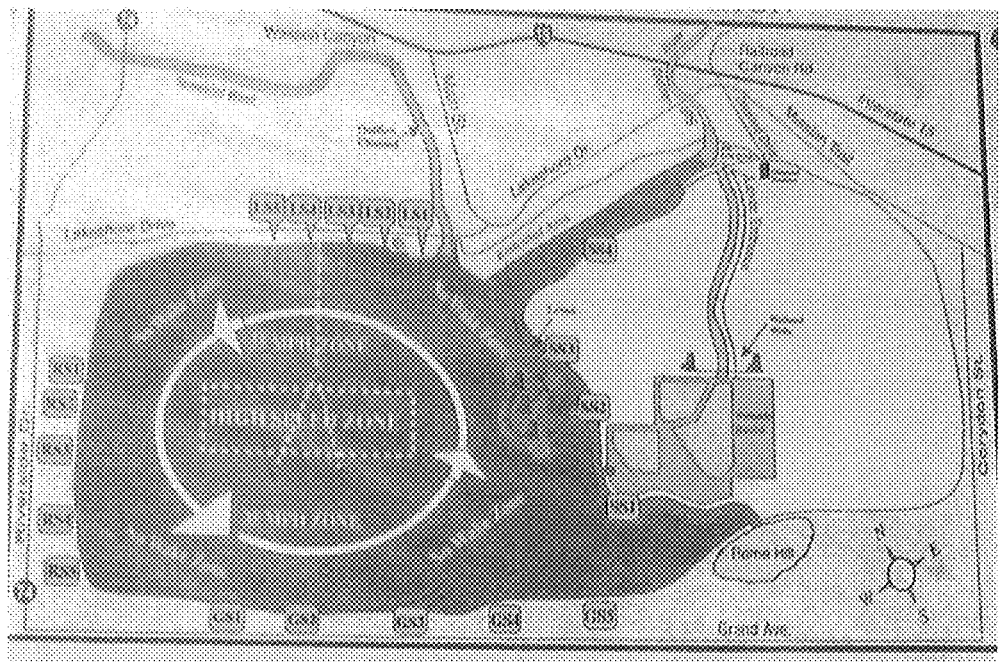

Sign titled "Shoreline Zone Identification," displaying the different regions of the lake. The inlet channel fed by the San Jacinto River is the northeastern arm, while the outflow channel (Temescal Wash), is directly to the west of the inlet. A darker blue line indicates the submerged roadway, and the arm inaccessible by boat titled "fish habitat." This area is shielded on every side, either by the levee or the roadway, and the separation can be viewed in many of the processed images.

FIGURE 62

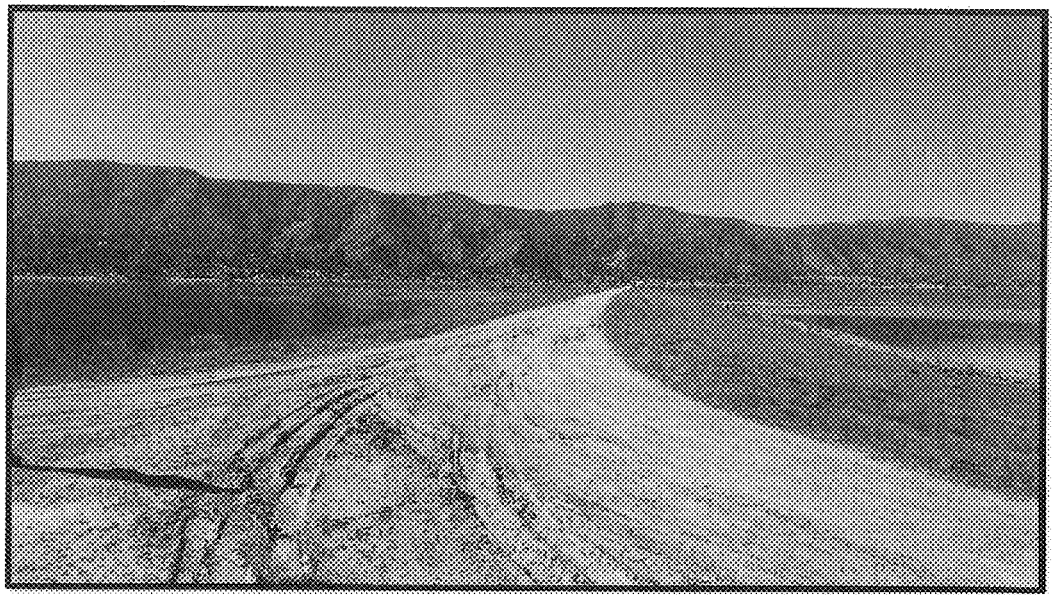

FIG. 63 Photo showing the levee strip that connects with the top of the "T" shape, separating the two small areas of water that meet at this strip. The area of water to the right is labeled "boater's bay" and does not show any significant water quality differences than the rest of the lake. The area of water to the left is the "fish habitat," and mixing with the rest of the lake is limited within this region.

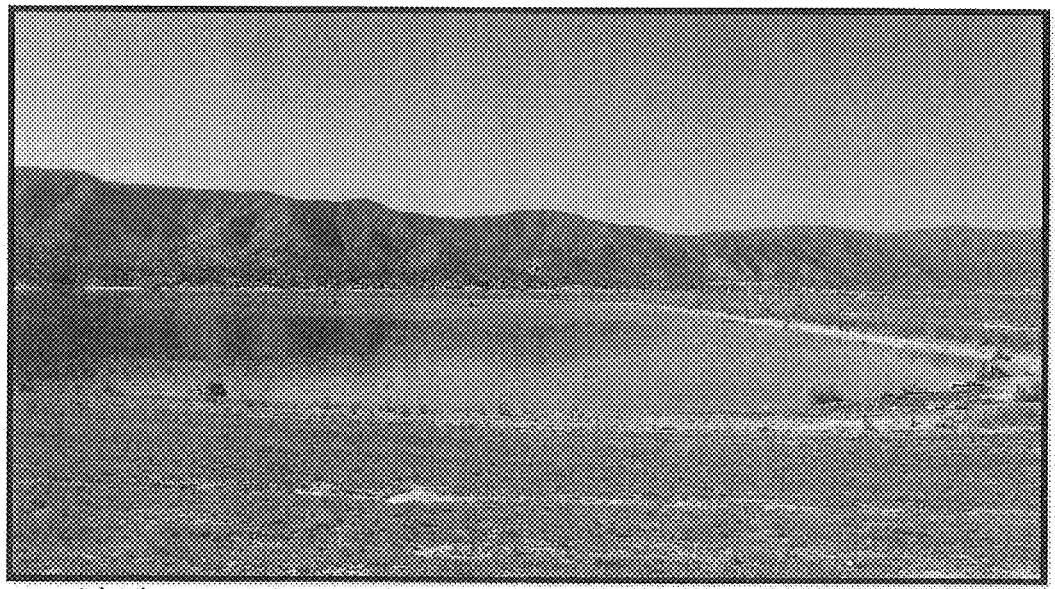

FIG 64 : Photo of the "fish habitat" region directly to the left of the levee strip shown in the previous image. The Elsinore Mountains line the background, which are part of the Santa Ana Mountain Range.

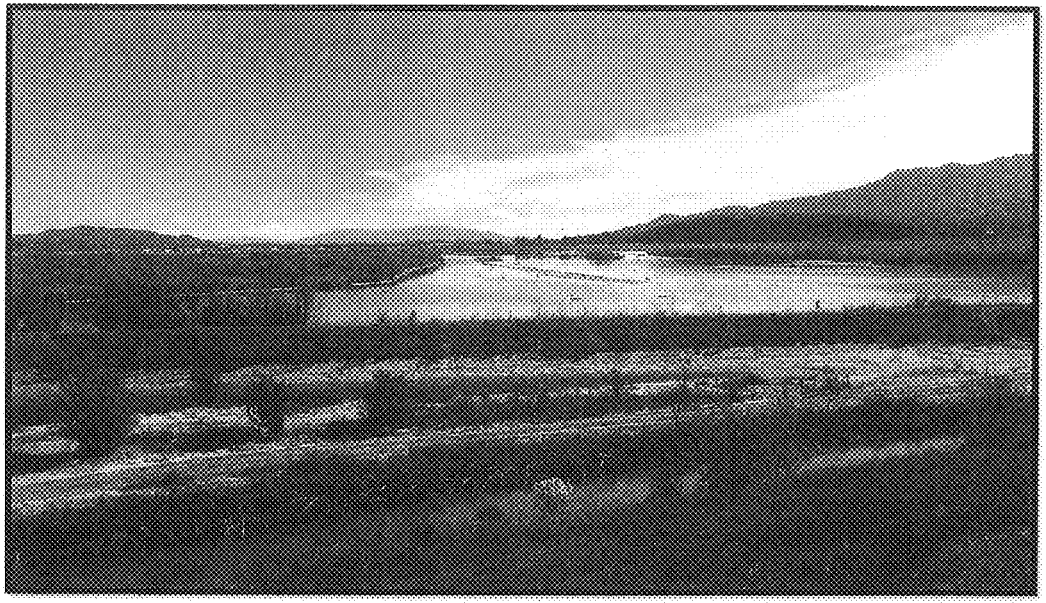

FIG. 65: Photo exhibiting a section of the constructed wetland habitat. Lying beyond these wetlands, on the southeast side, is an airport and a golf course.

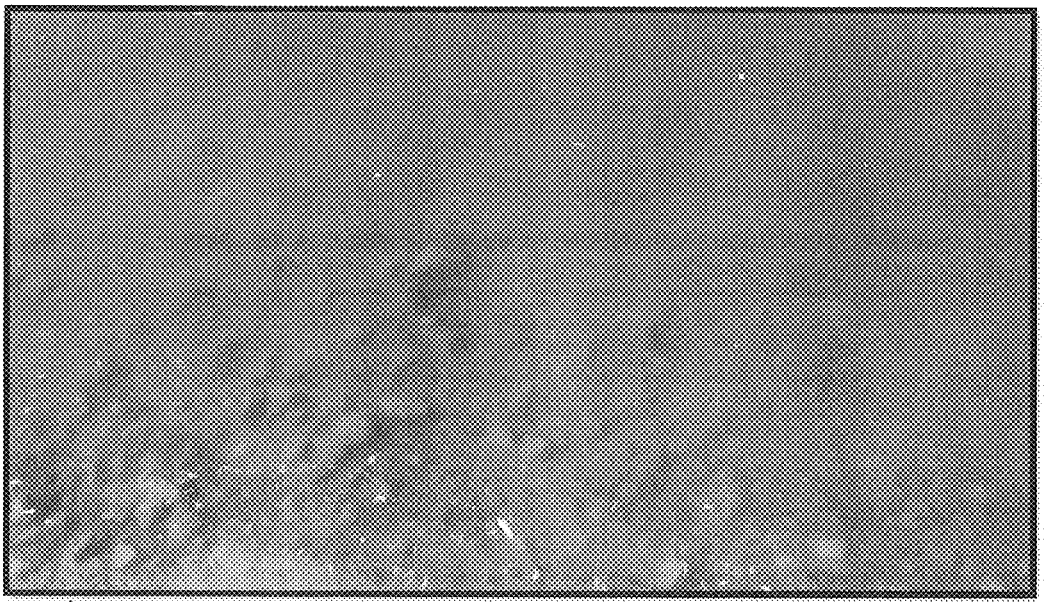

FIG. 66: Photo taken of the water along the shore of Lake Elsinore. The quality of this image represents most of the water around the shoreline, turbid with a brownish green hue. The green color of the lake can even be seen in some of the natural color satellite images. **All photos taken by Teagan Loew, on 1/5/2012.

METHOD AND RELATED SYSTEMS FOR MAPPING HIGH RANGES OF TOTAL PHOSPHATE CONTENT IN WATER USING MEASUREMENTS OF REFLECTED LIGHT OF OFF SURFACE WATER

CROSS-REFERENCE TO RELATED APPLICATIONS

This application is claiming the benefit, under 35 U.S.C. §119(e), of the provisional application filed Feb. 21, 2012 under 35 U.S.C. §111(b), which was granted Ser. No. 61/601,267. This provisional application is hereby incorporated by reference in its entirety.

FIELD OF THE INVENTION

The present invention relates to a method of and related systems of mapping factors indicative of water quality from satellite measurements of reflected sunlight off surface waters.

BACKGROUND

History and Explanation of the TMDL Policy/Program

Protecting and conserving water resources throughout the United States has been a concern and priority since the environmental movement and creation of the Environmental Protection Agency in 1970. In 1972 the Clean Water Act (amendments to the Federal Water Pollution Control Act) brought about many new policies to regulate water bodies across the country (Younos, 2005). Since then significant progress ensued with regards to regulating point sources, due to the National Pollution Discharge Elimination System (NPDES) permit program, under section 402 of the CWA. This permit process applies technology based controls to limit the discharge of pollutants from point sources (Lebowitz, 2001). Once a state regulatory agency has developed an approved NPDES program, it determines the amounts of certain pollutants that may be discharged by a particular discharger, from a specific source, and issues a permit that lists the requirements and limitations that discharger must follow for operation. If a state does not have an approved NPDES program, the U.S. EPA runs the permit process (Lebowitz, 2001).

The CWA also required the adoption of water quality standards for each state. The purpose of these standards is to identify the designated uses of each water body within the state, and to establish the water quality criteria based upon these uses. These standards are composed of chemical and biological components the water body must maintain for it to still meet its designated use (Lebowitz, 2001). The value of the waters for public water supplies, fish and wildlife use, recreational purposes, agricultural, industrial, and navigational use are all details that are taken into consideration. Any NPDES permit must limit the discharge of pollutants so that the water quality standards are met (Lebowitz, 2001). These standards are undeniably the key to protecting and preserving the quality of our country's water bodies. They set the baseline for determining whether regulatory efforts to preserve a water body's quality have been successful or not (U.S. EPA, 2003).

Perhaps the most important policy the CWA enacted is the Total Maximum Daily Load (TMDL) policy and program. Section 303(d) of the CWA states that each state, territory, and authorized tribe are required to develop lists of impaired water bodies, within their jurisdiction, and submit these lists to the U.S. EPA. An impaired water body is one that has failed to meet its designated use, as set by the states water quality standards (U.S. EPA, 1999). Each of these impaired water bodies requires an established TMDL. A TMDL, by definition, represents the maximum input, or load, of a certain pollutant from all the contributing point and/or nonpoint sources that may be added to a water body on a daily basis, while still allowing that water body to maintain or achieve its designated use (Lebowitz, 2001).

This policy lay dormant for some time, mostly due to confusion and the failure of the U.S. EPA to adequately address TMDLs in the basin planning process. The U.S. EPA failed to identify impaired waters as directed, and very few states were compiling lists of these impaired water bodies within their boundaries (Younos, 2005). Extensive litigation in the 1980s and 1990s began to unfold, and subsequently states started making lists of impaired waters and schedules for establishing the first TMDLs. These first few TMDLs only focused on point sources, such as reexamining permits through the NPDES process. By the early 1990s over 20,000 water bodies were identified as impaired and it was clear the U.S. EPA TMDL program needed some revamping (Younos, 2005).

The late 1990s and early 2000s brought about new policy and change focused on the TMDL program. In 1996 the Watershed Protection Approach Framework was adopted by the U.S. EPA as its framework for environmental management. This approach went hand in hand with the TMDL program, as it understood the complexity of nonpoint sources and the importance of stakeholder involvement to ensuring environmental regulations (Lebowitz, 2001). The following year the U.S. EPA also created the Federal Advisory Committee Act to provide states and regions some guidance for TMDL creation and implementation strategies. This committee tried to reach consensus among states, environmental groups, and point and potential nonpoint source dischargers for procedures of implementing the TMDL requirements under section 303(d) (Lebowitz, 2001). The main argument the committee faced, and one that continues today, is whether nonpoint source dischargers, like agricultural and timber industries, should be included in the TMDL regulations or not. These industries argue that nonpoint sources are already being controlled under section 319 of the CWA, which requires states to develop nonpoint source management programs for controlling pollution added from nonpoint sources to a water body identified as impaired. These groups claim that best management practices are enough and specific limits on pollutants are uncalled for.

In 1998 the Clean Water Action Plan (CWAP) was announced by President Clinton to address the lack of progress in meeting the goals of the CWA. The CWAP was the final push to create new rule changes for water quality management areas that were lacking. This plan geared federal, state, and local agencies and organizations to the watershed management approach, and therefore focused on implementing the TMDL program (Lebowitz, 2001). After the creation and discussion of proposals in 1999 regarding new TMDL rules, the administrator of the U.S. EPA signed these new rules on Jul. 1, 2000, titled "The Final Rule". The U.S. EPA stated these new rules were needed to strengthen the TMDL program, and to finally tackle the significant water quality problems that persist more than 25 years after the enactment of the CWA. These final revised rules build on the current TMDL regulatory program by adding needed details, many specific required steps, as well as schedules (Copeland, 2000). Though these new rules were stopped from being enacted by Congress, the draft of these rules provided much more clarity and a framework for states to follow.

Each state has its own TMDL program which can differ greatly from state to state due to resources, staff, funding, and the overall approach followed. Each program is comprised of individual TMDLs for each water body. These TMDLs are large documents that include numerous details to run and ultimately complete the project (U.S. EPA, 1999). The back bones of these documents are the actual TMDLs for each pollutant that is impairing the water body. This states the amount of the pollutant the water body can receive and still meet its water quality standards. These pollutants are then linked to point or nonpoint sources. Allocations are calculated for each pollutant for each source, based on the TMDL. Wasteload allocations refer to point sources, while load allocations refer to nonpoint sources (FIG. 1, U.S. EPA, 1999).

Eleven different elements are required to be included in a state TMDL: 1) impaired water body name and geographic location; 2) identification of the pollutant and applicable water quality standard; 3) amount of the pollutant load that may be present in the water body and still meet its water quality standards; 4) the amount of the pollutant load present in the water body that exceeds the total maximum daily load; 5) identification of the source categories, subcategories, or individual sources of the pollutant for which wasteload and load allocations are being established; 6) wasteload allocations; 7) load allocations; 8) a margin of safety that allows for uncertainty; 9) consideration of seasonal variations; 10) allowance for future growth which may account for reasonably foreseeable pollutant load increases; 11) an implementation plan; (U.S. EPA, 1999).

Problems with TMDL Program and Process

The sampling procedure and analysis process are very important in determining correct and viable maximum loads, to ensure they are not understated or overstated, and that they properly represent the entire water body. The ability to capture water quality data sets over the surface of entire water bodies has been a goal of surface water professionals for decades. The monitoring process for these stated pollutants and their capacities is an essential part of ensuring that the water body will eventually be removed from the impaired list, and will once again meet its water quality standards. Several different studies examining implementation success of TMDLs have pointed out that monitoring is a factor that makes or breaks implementation success (Benham & Zeckoski, 2007; Furtak & Norton, 2009; Virginia Tech, 2006; Younos, 2005). In one study it was stated that one of the two most negative factors affecting TMDL implementation success is a lack of data, due to the failure to properly monitor the impaired water body (Benham & Zeckoski, 2007).

Currently, sampling procedures among different states vary from agency to agency due to the amount of available resources such as staff and funding (Younos, 2005). States that are short staffed or lack funding are not able to enforce a consistent measurement and monitoring routine. Therefore, these impaired water bodies lack the adequate amount of sample sizes and monthly monitoring visits. The state of Ohio is a great example of a state agency lacking adequate funding. The U.S. EPA has provided the agency with a small grant to look at up to 12 lakes per year, over a two year period. When these lakes are sampled, the normal procedure is to collect water samples from one to two locations in the deepest portion of the lake (Merchant, 2010). This current sampling routine and procedure is not enough to confidently consider if a water body has failed to meet its water quality standards, and to accurately provide a sufficient amount of monitoring to supervise the water bodies overall health.

Providing data sets without considerable data gaps is extremely difficult using field sampling methodology. These conventional methods for detecting phosphate concentrations and other water quality markers are time-consuming and expensive, especially for multi-seasonal monitoring over large-scale areas. Further, convention testing methods do not allow mapping of phosphate concentrations and other water quality markers in the past, which is important for understanding sources of phosphate contamination and other water quality markers.

Characterizing the chemistry of a surface water body is often limited by: large surface areas, time constraints, available manpower, access to sample collection points, and project cost or budget constraints. These limitations typically result in the gathering of grab samples that are not sufficient to statistically represent the average chemical characteristics of the entire surface water area being studied. Consequently, these data gaps may lead to the compilation of misleading, overly conservative or inadequate evaluations with respect to monitoring and remedial efforts towards improving water quality.

Currently, surface water data can be collected in situ using field sampling methods. Data is typically collected by a field technician who may analyze water samples using field instruments, portable laboratory kits or through the process of sending samples into a laboratory. Deciding what method to use depends upon the goals of specific projects and data quality requirements. Costs for field sampling include labor, equipment, fuel, laboratory and reporting fees. These costs are typically in the hundreds of United States dollars per sample.

Additionally, in situ testing of remote bodies of water or those that are otherwise difficult to access can be costly and time consuming to even obtain the sample. The present invention allows mapping of these bodies of water without the time, effort, and expense of traveling to such bodies of water.

In 2002 the U.S. EPA stated that sample size is an important element of data quality, and sample sizes are important for statistical tests in detecting Water Quality Standard exceedances (U.S. EPA, 2002). In general a sample size of 30 or more is accurate, while smaller sample sizes are inaccurate and have a low probability of detecting any exceedances (U.S. EPA, 2002). Any decisions based on very small data sets should only be made when there is overwhelming evidence of a specific impairment. The National Lake Assessment, completed by the U.S. EPA in 2007, had crews collect one sample at a single station in the deepest point of the lake, and at some sites had an additional ten collection stations around the perimeter of the lake (U.S. EPA, 2009). As the U.S. EPA stated in 2002, taking one sample or even an additional ten samples is not accurate enough to truly represent the overall quality of the entire water body, regardless of how many parameters are measured from those few samples.

As of Jan. 12, 2012 there are a total of 41,266 impaired water bodies throughout the country in need of a TMDL. There are a total of 46,817 TMDLs that have been approved by the U.S. EPA, that are now in the implementation and monitoring phase (U.S. EPA, 2012). The amount of TMDLs focused on impairments by nutrients is 6,893 ($3^{rd}$ most common impairment), while 5,249 nutrient TMDLs have been already been created (USEPA, 2012). The state of California alone has 1,189 approved TMDLs that are now in the implementation and monitoring phase (USEPA, 2012). These numbers clearly indicate that the TMDL program needs assistance, in both the creation and monitoring phases. Satellite remote sensing can provide large amounts of data to help define impairments, design the total maximum daily loads, and efficiently monitor these water bodies.

Satellite Remote Sensing

Over the past decade, satellite remote sensing data has proven to be an essential tool in several different aspects of environmental science. Remote sensing has been shown to aid greatly in analyzing and monitoring bodies of water and assessing their quality. Several different studies have had success at measuring and monitoring different water quality parameters, such as chlorophyll-$\alpha$ and turbidity (Cooper & Ritchie, 2001; Govender, et. al., 2006; Hadjimitsis & Clayton, 2011). Algorithms have been developed that effectively measure various aqueous chemical constituents, completely from space acquired data that has a dense net of data points. The data from these algorithms have high statistical correlations with water measurements taken from within the water body (Vincent, 2010). Satellites provide temporal and spatial data for surface water quality parameters that is not possible from in situ measurements (Cooper & Ritchie, 2001). LANDSAT TM satellite data is free and can be received as quickly as a few hours to a few days after satellite overpass. These satellite images have a 30 meter spatial resolution that produces five measurement points per acre: if a body of water is 3,000 acres in size, then there will be 15,000 measurements for each satellite pass over that body of water (Vincent, 1997).

The incorporation of satellite monitoring into the TMDL process is a low-cost and effective way to obtain a much greater magnitude of accurate data for a particular water body, as compared to manual sample collection procedures. For example, satellite remote sensing gives up to 5,000 times more measurements for a 1,000-acre lake. Satellite monitoring can also be performed on a monthly basis, without having requiring the funding or staff to collect water samples. Though satellite water quality algorithms have currently been developed for only a few water quality parameters, more will be developed in time. Also, some of the current satellite water quality algorithms may also prove to have a strong correlation with other parameters presently without a satellite algorithm. The technology and capability to develop such algorithms are sure to increase in the future, with the development and launching of new satellites designed for this purpose.

Remote sensing of entire water body highlights areas of significant impact so the user can focus monitoring and remedial efforts at those locations. In many instances, this results in reducing costs for monitoring or physical/chemical treatments because the entire water body does not have to be monitored or chemicals may not need to be applied to an entire body of water. This focused approach to remediation results in a level of detail not possible using evaluations from single grab samples. Thus, there is a need for an efficient and cost effective method for obtaining the comprehensive data packages to supplement current monitoring and modeling programs for bodies of water.

Devices and techniques disclosed in U.S. Pat. No. 7,132,254, U.S. patent application Ser. No. 10/762,952, and U.S. patent application Ser. No. 13/284,145 relating to remote sensing may be adapted to the present invention and are hereby incorporated by reference.

The present invention is able to determine the total phosphate concentration for every one-fifth of an acre in a surface body of water within a few seconds. As noted previously, one measurement in a lake by current in situ methods costs approximately $600 dollars per data point. If a measurement were taken for a 1,000 acre lake, 5,000 measurements would be needed to match the present invention. The cost to do so would be approximately $1.5 million. The present invention obtains the same results for only about $0.10 to $2.00 per acre, which would total $100-$2000 for a 1,000 acre lake.

Excessive nutrient input into water bodies accounts for one of the most common type of impairment, and currently 6,893 water bodies are in need of a nutrient TMDL, while 5,249 require the monitoring of nutrient impairments (U.S. EPA, 2012). Many of the studies that have resulted in success with various algorithms to monitor water bodies are mainly parameters that are measured and monitored for nutrient TMDLs, as nutrients are normally the impairments. Therefore, it is evident that this could especially be an area that satellite remote sensing could improve.

One reason it is important to map and detect phosphate concentrations in bodies of water is because elevated phosphate levels are one of the root causes of increased blooms of these harmful algae such as cyanobacteria. Through mapping past phosphate levels, it is possible to track when and how phosphate enters a body of water.

An important factor to note concerning nutrient TMDLs are the resulting algal blooms and the parameters chosen to monitor this degradation. After excessive nutrient inputs, massive blooms of algae often follow, including Harmful Algal Blooms (HAB) that contain cyanobacteria. Different strains of cyanobacteria create dangerous toxins, which are harmful to animals and humans (Ingraham, 2000). Where a nutrient impairment exists, and algal blooms are present, it is extremely important to determine whether these blooms contain cyanobacteria (Gons, 2005). Many water bodies used for recreational purposes are being closed to the public due to these blooms and the dangers they present human health. While chlorophyll-$\alpha$ is currently the most widely used parameter used to monitor algal blooms, a pigment known as phycocyanin should be established as another parameter used to monitor lakes for cyanobacteria. Chlorophyll-$\alpha$ is contained by a majority of all land plants and algae, while phycocyanin is found almost uniquely in cyanobacteria, and in a few other algae species (Ingraham, 2000). Previous studies have created algorithms to accurately measure and monitor the more nearly unique cyanobacterial pigment, phycocyanin, for the regulation of cyanobacteria blooms (Vincent et al., 2004). More attention should be drawn to this parameter, and phycocyanin algorithms for both low blooms and high blooms of cyanobacteria will be applied in this study.

The presented embodiments show how remote sensing applications can improve the TMDL process in two main areas: the original measurement process to determine the impairments and maximum loads of the subject water body, and the subsequent monitoring process, to determine how successfully the impairments have been mitigated.

SUMMARY

The presented embodiments employ remote sensing technology to determine the total phosphate concentration of a body of water. In addition, the presented embodiments employ methods and systems for determining other parameters of water quality from reflected light, for example, turbidity, dissolved oxygen and/or nitrogen.

The presented embodiments allow one to detect and determine the total phosphate concentration in a body of water from reflected light. The presented embodiments allow one to detect the total phosphorus in high ranges of total phosphate concentration in a body of water from reflected light. The presented embodiments may be used advantageously for any purpose, such as (1) to determine changes in phosphate concentrations in a given body of water, (2) to determine sources of phosphate concentration by mapping phosphate concentrations of streams and rivers or noting what areas of a lake or ocean or other large body of water have higher phosphate concentrations, and (3) to quickly determine potentially dangerous phosphate concentrations in a body of water. It will be understood that the presented embodiments may be applied to any surface of water.

The presented embodiments also allow one to detect and determine the turbidity in a body of water from reflected light.

As used herein, remote sensing refers to the capability of obtaining information about an object without touching it. Sensors which are not in direct contact with the object are generally used to obtain the information. In a more limited context, the information obtained by remote sensing is a function of energy emitted by, absorbed by, or reflected from the object.

The presented embodiments are especially useful at high ranges of total phosphate concentrations. As used herein, high ranges of total phosphate concentrations are total phosphate concentrations at least above 0.1 ppm. In other embodiments, high ranges of total phosphate concentrations are between 0.1 and 0.7 ppm. In still other embodiments, high ranges of total phosphate concentrations are between 0.2 and 0.7 ppm. In still other embodiments, high ranges of total phosphate concentrations are between 0.2 and 0.6 ppm. In other embodiments, high ranges of total phosphate concentrations are between 0.3 and 0.7 ppm. In other embodiments, high ranges of total phosphate concentrations are at least 0.3 ppm.

The presented embodiments employ remote sensing technology to determine the chemical contents of bodies of water and to detect other markers of water quality. In general terms, the presented embodiments include a method of determining the amount of total phosphate in a body of water from reflected light as well as systems for determining the amount of total phosphate in a body of water from reflected light. In general terms, the presented embodiments include a method of determining the amount of turbidity in a body of water from reflected light as well as systems for determining the amount of turbidity in a body of water from reflected light. It will be understood that the presented embodiments may be applied to any surface of water, such as rivers, lakes, streams, oceans, and flood plains.

Methods

The presented embodiments include a method of determining the amount of total phosphate in a body of water from reflected light. The method comprises the steps of: (a) obtaining a measurement of reflected light from a body of water, the measurement comprising a measurement of respective amounts of light in at least two, and preferably at least five wavelength ranges; and (b) determining the amount of total phosphate from the respective amounts of light by applying an algorithm relating the respective amounts of light in the wavelength ranges to the amount of the total phosphate in the body of water. This will preferably be done through the use of an algorithm that involves a ratio of the respective amounts of light in the at least two wavelength ranges.

Also presented is a method for determining the amount of turbidity in a body of water. The method comprises the steps of: (a) obtaining a measurement of reflected light from a body of water, the measurement comprising a measurement of respective amounts of light in at least two, and preferably at least five wavelength ranges; and (b) determining the amount of turbidity from the respective amounts of light by applying an algorithm relating the respective amounts of light in the wavelength ranges to the amount of the turbidity in the body of water. This will preferably be done through the use of an algorithm that involves a ratio of the respective amounts of light in the at least two wavelength ranges.

Typically, wavelength ranges may also include a single wavelength, so it will be understood that reference to wavelength ranges herein also includes single wavelengths. The wavelength ranges typically will be discreet ranges for most detectors, such as satellites, although amounts of light in overlapping ranges may be used as well.

It is preferred that the values of the reflectance are determined as dark object subtracted values as DOS-corrected digital number (DN) values of the selected spectral bands (i.e., wavelength ranges), such as in the case of satellite spectral bands.

It will be understood that reference to the concentration of phosphorus or phosphate in water means the detection of this element and/or this element in whatever oxidation state or other bound state that it may be present in the target body of water.

The presented embodiments further includes a method wherein the algorithm comprises a quantitative relationship between: (i) the ratio of the amount of light in a first of the wavelength ranges to the amount of light in a second of the wavelength ranges, (ii) the ratio of the amount of light in a third of the wavelength ranges to the amount of light in the first of the wavelength ranges, (iii) the ratio of the amount of light in a fourth of the wavelength ranges to the amount of light in the first of the wavelength ranges, (iv) the ratio amount of light in a fifth of the wavelength ranges to the amount of light in the first of the wavelength ranges, (v) the ratio of the amount of light in a fifth of the wavelength ranges to the amount of light in the third of the wavelength ranges, and (vi) the ratio of the amount of light in the fifth of the wavelength ranges to the amount of light in the fourth of the wavelength ranges, and the amount of the total phosphate in a body of water.

The method of the presented embodiments may additionally comprise the step of generating a report of the approximate amount of the total phosphate in water. The method of the presented embodiments may additionally comprise the step of generating a report of the approximate amount of turbidity in water. This may be done using electronics adapted to digitize and process the data using an appropriate algorithm, such as that described herein. For instance, the report may include an estimate of the number of the total phosphate in parts per million in the water. Or, the report may include an estimate of the turbidity in NTUs. Such a report generator may be any device that is adapted to place the data into a tangible medium, such as a printer, CD burner, flash memory, magnetic storage media, etc.

The presented embodiments also include a method wherein the measurement of reflected light is obtained using a light measurement device, which may be any device adapted to sense and record and/or transmit the light wavelengths described, such as a photosensor, camera, digital camera, video camera, etc. The measurement device may be placed in any position from which it can sense the required light wavelengths, such as on a buoy, a boat, a light house, a satellite, or similar dedicated structure. The measurement device may also be in the form of a handheld device, such as a camera connected to a processor for processing the recorded light wavelengths, the device may also be in the form of a device similar to a personal digital assistant, smart phone or tablet computer, with light recording and processing functions.

The method according to the presented embodiments is such that the calculated value of total phosphate in a body of water correlated to the actual measured amount of the total phosphate in the water by an adjusted square correlation value (i.e., R2 adjusted) in excess of 70% and as high as in excess of 80%.

The method according to the presented embodiments is such that the calculated value of turbidity in a body of water correlated to the actual measured amount of turbidity in the water by an adjusted square correlation value (i.e., R2 adjusted) in excess of 70% and as high as in excess of 80%.

The method of the presented embodiments may also include the step of transmitting data relating to the approximate amount of the total phosphate in the body of water to a site remote from the site where the measurement takes place. The method of the presented embodiments may also include the step of transmitting data relating to the approximate amount of turbidity in the body of water to a site remote from the site where the measurement takes place. This may be done using any transmission method including land line or wireless transmission. This may also be used advantageously where the reflected light is sense remotely by aircraft, satellite, boat or buoy. Processing of the data may take place at the site of light uptake or may be carried out at a remote location after transmission of the raw data. The estimated total phosphate report may be sent to public authorities, such as police departments, fire and rescue departments or life guard services to warn swimmer, boater, sportsman or the public at large that a given body of water, or portion thereof, likely contains elevated/dangerous levels of phosphate.

The presented embodiments also include a method wherein the wavelength ranges are all in the visible and infrared ranges. Preferably, the presented embodiments include a method wherein the measurement of the amount of light comprises measurements in at least five wavelength ranges, respectively, of: (i) LANDSAT TM band 1, (ii) LANDSAT TM band 2, (iii) LANDSAT TM band 3, (iv) LANDSAT TM band 4, and (v) LANDSAT TM band 5.

Preferably, the algorithm comprises a quantitative relationship between the sum of the following ratios:
1. The reflectance in LANDSAT TM band 2 divided by the reflectance in LANDSAT TM band 1, after subtraction of the reflectance of atmospheric haze separately in each band;
2. The reflectance in LANDSAT TM band 3 divided by the reflectance in LANDSAT TM band 2, after subtraction of the reflectance of atmospheric haze separately in each band;
3. The reflectance in LANDSAT TM band 4 divided by the reflectance in LANDSAT TM band 2, after subtraction of the reflectance of atmospheric haze separately in each band;
4. The reflectance in LANDSAT TM band 5 divided by the reflectance in LANDSAT TM band 2, after subtraction of the reflectance of atmospheric haze separately in each band;
5. The reflectance in LANDSAT TM band 5 divided by the reflectance in LANDSAT TM band 3, after subtraction of the reflectance of atmospheric haze separately in each band; and
6. The reflectance in LANDSAT TM band 5 divided by the reflectance in LANDSAT TM band 4, after subtraction of the reflectance of atmospheric haze separately in each band.

The preferred example of this algorithm is as follows: $TP=1.14+0.385*R21-3.16*R32+1.72*R42+1.88*R52-3.52*R53+1.87*R54$, wherein:
1. TP is the approximate amount of total phosphate expressed in parts per million or milligrams of phosphate per liter of water;
2. R21 is the value of LANDSAT TM band 2 divided by LANDSAT TM band 1, after subtraction for atmospheric haze separately in each band;
3. R32 is the value of LANDSAT TM band 3 divided by LANDSAT TM band 2, after subtraction for atmospheric haze separately in each band;
4. R42 is the value of LANDSAT TM band 4 divided by LANDSAT TM band 2, after subtraction for atmospheric haze separately in each band;
5. R52 is the value of LANDSAT TM band 5 divided by LANDSAT TM band 2, after subtraction for atmospheric haze separately in each band;
6. R53 is the value of LANDSAT TM band 5 divided by LANDSAT TM band 3, after subtraction for atmospheric haze separately in each band; and
7. R54 is the value of LANDSAT TM band 5 divided by LANDSAT TM band 4, after subtraction for atmospheric haze separately in each band.

The presented embodiments therefore include a method of determining the presence of total phosphate in water from light reflected therefrom, the method comprising the steps of: (a) obtaining a measurement of reflected light from the water, the measurement comprising a measurement of the respective amount of light in at least five wavelength ranges comprising, respectively: (i) LANDSAT TM band 1, (ii) LANDSAT TM band 2, (iii) LANDSAT TM band 3, (iv) LANDSAT TM band 4, and (v) LANDSAT TM band 5; and (b) relating the approximate amount of the total phosphate in the water to the respective amount of light by applying an algorithm relating the respective amount of light in the at least five wavelength ranges to the amount of total phosphate in the water, wherein the algorithm is: $TP=1.14+0.385*R21-3.16*R32+1.72*R42+1.88*R52-3.52*R53+1.87*R54$ wherein:
(a) TP is the approximate amount of total phosphate expressed in parts per million or milligrams of phosphate per liter of water;
(b) R21 is the value of LANDSAT TM band 2 divided by LANDSAT TM band 1, after subtraction for atmospheric haze separately in each band;
(c) R32 is the value of LANDSAT TM band 3 divided by LANDSAT TM band 2, after subtraction for atmospheric haze separately in each band;
(d) R42 is the value of LANDSAT TM band 4 divided by LANDSAT TM band 2, after subtraction for atmospheric haze separately in each band;
(e) R52 is the value of LANDSAT TM band 5 divided by LANDSAT TM band 2, after subtraction for atmospheric haze separately in each band;
(f) R53 is the value of LANDSAT TM band 5 divided by LANDSAT TM band 3, after subtraction for atmospheric haze separately in each band; and
(g) R54 is the value of LANDSAT TM band 5 divided by LANDSAT TM band 4, after subtraction for atmospheric haze separately in each band.

The presented embodiments further provide a method of determining the amount of total phosphate in a body of water from light reflected therefrom, the method comprising the steps of: (a) obtaining a measurement of reflected light from the body of water, the measurement comprising a measurement of respective amounts of light in at least five wavelength ranges (i) from about 0.45 µm to about 0.52 µm, (ii) from about 0.52 µm to about 0.61 µm, (iii) from about 0.63 µm to about 0.69 µm, (iv) from about 0.76 µm to about 0.9 µm, and (v) from about 1.55 µm to about 1.75 µm; (b) determining the approximate amount of total phosphate in water from the respective amount of lights of light by applying an algorithm relating the respective amounts of lights in the at least five wavelength ranges to the amount of total phosphate in the water. The wavelength ranges used in the present invention are typically in the visible and infrared ranges. The present invention also includes a method additionally comprising the step of generating a report of the approximate amount of the total phosphate in water.

Systems

The presented embodiments include a system for determining the amount of total phosphate in a body of water from light reflected therefrom, the device comprising: (a) a measurement device adapted to obtain a measurement of reflected light from the body of water, the measurement comprising a measurement of respective amounts of light in at least two, and preferably at least five wavelength ranges; and (b) a processor capable of determining the amount of the total phosphate from the respective amounts of light by applying an algorithm relating the respective amounts of light in the wavelength ranges to the amount of the total phosphate in the body of water, preferably the algorithm comprising a ratio of the amount of light in a first of the at least two wavelength ranges to the amount of light in a second of the at least two wavelength ranges. It is further preferred that the algorithm comprise a first ratio of the amount of light in a first of the at least two wavelength ranges to the amount of light in a second of the at least two wavelength ranges, and a second ratio, different than the first ratio (i.e., not involving the same amounts in the same numerator and denominator position), of the amount of light in one of the at least two wavelength ranges to the amount of light in another of the at least two wavelength ranges.

The presented embodiments also includes a system wherein the system comprises (a) a measurement device adapted to obtain a measurement of reflected light from the water, the measurement comprising a measurement of the respective amount of light in at least five wavelength ranges comprising, respectively: (i) LANDSAT TM band 1, (ii) LANDSAT TM band 2, (iii) LANDSAT TM band 3, (iv) LANDSAT TM band 4, and (v) LANDSAT TM band 5; and (b) a processor capable of determining the approximate amount of the total phosphate in the water to the respective amount of light by applying an algorithm relating the respective amount of light in the at least five wavelength ranges to the amount of total phosphate in the water, wherein the algorithm is: $TP = 1.14 + 0.385*R21 - 3.16*R32 + 1.72*R42 + 1.88*R52 - 3.52*R53 + 1.87*R54$ wherein:

(a) TP is the approximate amount of total phosphate expressed in parts per million or milligrams of phosphate per liter of water;
(b) R21 is the value of LANDSAT TM band 2 divided by LANDSAT TM band 1, after subtraction for atmospheric haze separately in each band;
(c) R32 is the value of LANDSAT TM band 3 divided by LANDSAT TM band 2, after subtraction for atmospheric haze separately in each band;
(d) R42 is the value of LANDSAT TM band 4 divided by LANDSAT TM band 2, after subtraction for atmospheric haze separately in each band;
(e) R52 is the value of LANDSAT TM band 5 divided by LANDSAT TM band 2, after subtraction for atmospheric haze separately in each band;
(f) R53 is the value of LANDSAT TM band 5 divided by LANDSAT TM band 3, after subtraction for atmospheric haze separately in each band; and
(g) R54 is the value of LANDSAT TM band 5 divided by LANDSAT TM band 4, after subtraction for atmospheric haze separately in each band.

Finally, the presented embodiments also include a system for determining the amount of total phosphate in a body of water from light reflected therefrom, the system comprising: (a) a measurement device adapted to obtain a measurement of reflected light from the body of water, the measurement comprising a measurement of respective amounts of light in at least five wavelength ranges (i) from about 0.45 µm to about 0.52 µm, (ii) from about 0.52 µm to about 0.61 µm (iii) from about 0.63 µm to about 0.69 µm, (iv) from about 0.76 µm to about 0.90 µm, and (v) from about 1.55 µm to about 1.75 µm; and (b) a processor capable of determining the approximate amount of total phosphate in water from the respective amount of lights of light by applying an algorithm relating the respective amounts of lights in the at least five wavelength ranges to the amount of total phosphate in the water.

The measurement device and processor may be incorporated into the same article or vehicle, or may be distributed between different components of the system.

The processor may be of any type appropriate to carry out the calculation and determination/estimation of the amount of the target substance as described herein. It may be in data communicative contact with the measurement device through any appropriate means, such as through the use of data transmission means and/or storage media known and used in the information technology and data processing fields.

The measurement device may be selected from the group consisting of cameras, photosensors and satellites.

The system of the presented embodiments may additionally include a report generator adapted to generate a report of the approximate amount of the total phosphate in the body of water. Such a report generator may be any device that is adapted to place the data into a tangible medium, such as a printer, CD burner, flash memory, magnetic storage media, etc.

The system of the presented embodiments may additionally include a display for displaying an image representing the data generated by the system, so as to be able to visualize the results of the assay method carried out by the system, in accordance with the present invention. Typical digital images for use in this method may be prepared from digital information taken from aerial platforms or satellites, and either may be stored digitally when taken or transferred into digital format. Typical sources of data from digital images may include digital or film cameras or spectrometers carried by aircraft or satellite.

The system may additionally include a transmitter adapted to transmit data relating to the approximate amount of the nutrients in the soil from the processor to a site remote from the site where the measurement takes place. Such a transmitter may include those adapted to send data such as through land line or wireless transmission, including telephone, internet, cell phone, radio and the like.

The measurement device may be any device adapted to sense and record and/or transmit the light frequencies described above. Examples include photosensors or any appropriate type considering the distances, reflectivity profile, dispersion, and reflectance in each application of the invention, cameras, digital cameras and video cameras, etc.

The processor may be any data processing device having programming instructions for applying the algorithm(s), such as preferably a microprocessor.

The measurement device may be placed in any position from which it can sense the required light frequencies, such as on an aircraft or satellite or on a support, such as a dedicated tower structure, such as a barn or silo. The measurement device may also be in the form of a handheld device, such as a camera connected to a processor for processing the recorded light frequencies, the device may also be in the form of a device similar to a personal digital assistant with light recording and processing functions. For instance, the measurement device may include sensors adapted to measure the same spectral bands on a tractor or other farming vehicle, such as for measuring the phosphorus, sulfur and/or copper in the bare soil, such as by being mounted in front and/or in back of the tractor.

Another variation of the presented embodiments is a system using transmission of light measurement data to processor at a different location, recognizing that the processing may be done at a different location than the light sensing/recording.

It will be understood that the expression of the amount of total phosphate in a body of water in parts per million, or turbidity in NTUs, is only one way to express the amount, and that reference to mathematical equivalents refers to any mathematically or logically related algorithms or expressions. The method according to the presented embodiments is such that the calculated value of total phosphate concentrations in a body of water correlates to the actual measured amount of total phosphate (based upon well-known physical sampling techniques) by an adjusted square correlation value in excess of 72% and as high as in excess of 85%.

The presented embodiments also include a method of developing an apparatus for determining the amount of phosphate in water from light reflected therefrom, the device comprising (a) obtaining a measurement of reflected light from the water, the measurement comprising a measurement of the respective amount of light of at least two wavelengths, and preferably in at least five wavelengths; (b) developing an algorithm relating the respective amounts of light in the at least two and preferably at least five wavelengths to the amount of phosphate in the water through linear regression analysis; (c) producing a processor capable of relating the approximate amount of the phosphate in the water to the respective amounts of light by applying an algorithm relating the respective amounts of light in the at least two and preferably at least five wavelength ranges to the amount of phosphate in the water; and (d) providing a measurement device adapted to measure reflected light from the water and adapted to provide data relating to the measurement to the processor.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above, as well as other advantages of the present disclosure, will become readily apparent to those skilled in the art from the following detailed description when considered in the light of the accompanying drawings in which:

FIG. 41 shows an image created to display which portions of Lake Elsinore are meeting TMDL requirements for total phosphorus and which are not, for Aug. 28, 2002. In this case, a majority of the lake is within the category of 101-300 ppb, and not meeting the requirement. Note the two areas in the south eastern portion fall into the "extremely high" category, the constructed wetlands and the small channel used for a fish habitat.

FIG. 60 in Appendix B shows a photograph of the inlet channel on the eastern side of Lake Elsinore.

FIG. 61 in Appendix B shows a graphical depiction of Lake Elsinore levee system fishing and wildlife viewing area.

FIG. 62 in Appendix B shows a graphical depiction of Lake Elsinore shoreline zone identification.

FIG. 63 in Appendix B shows a photograph of a levee strip of Lake Elsinore.

FIG. 64 in Appendix B shows a photograph of the fish habitat of Lake Elsinore.

FIG. 65 in Appendix B shows a photograph of a portion of the constructed wetland habitat of Lake Elsinore.

FIG. 66 in Appendix B shows a photograph of water taken along the shore of Lake Elsinore.

DETAILED DESCRIPTION

Figure 1:
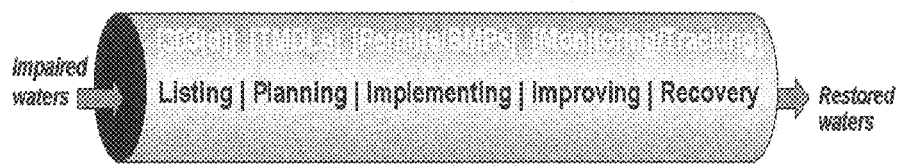
FIG. 1 shows a shortened and simplified depiction of a theoretical TMDL step by step process (Furtak & Norton, 2009).

In accordance with the foregoing summary, the following is a detailed description of the preferred embodiments of the invention, which are considered to be the best mode thereof. The preferred method and system herein described is not intended to be exhaustive or to limit the invention to the precise forms disclosed. They are chosen and described to explain the principles of the invention and the application of the method to practical uses so that others skilled in the art may practice the invention.

The method of the present invention may be carried out using any sensing appropriate light sensing devices adapted to capture the algorithm-relevant frequencies as described herein, including satellite and surface sensors for detection of total phosphate.

An algorithm that may be used in the present invention, which may be carried out by computer instructions for producing a particular type of image that can be used to map a particular substance from a remote sensing platform in space, in an aircraft, or on the ground, may be determined as follows:

LANDSAT Thematic Mapper (TM) is a sensor that has 8 spectral bands, 6 of which have a 30-meter spatial resolution and which detect visible and infrared radiation (sunlight) reflected off the Earth's surface. The following bands were employed, with the wavelength limits (in micrometers, or μm) of their spectral band-widths given below for the LANDSAT 7 version of TM, called ETM+, and the LANDSAT 4 and 5 versions, called TM:

present invention to determine large-scale phosphate concentrations in difficult environments. At least four satellites have been commonly used for mapping of various substances in bodies of water: AVHRR, SEAWIFS, and MODIS, all of which have spatial resolutions that range from 250-1,000 meters in pixel size. Where one is interested in results beyond the large scale lakes, to smaller fresh water lakes and their tributaries, as well as small inland lakes, the 30-meter resolution of the six visible/reflective IR spectral bands of LANDSAT TM and ETM+ are preferably selected. However, LANDSAT TM data has traditionally had one exceptional disadvantage: though data are collected by the LANDSAT satellites with a 16-day frequency (8-day frequency for two LANDSAT satellites), the data were not readily available to civilian scientists in less than approximately 60 days following the data collection. The availability of LANDSAT TM data within 24-48 hours through the OhioView consortium (a remote sensing consortium of eleven of Ohio's public research universities) permits non-government scientists to perform time-sensitive research with LANDSAT data for the first time since ERTS I (later called LANDSAT I) was orbited in 1972.

TABLE 1

TM and ETM+ Spectral Bandwidths
Bandwidth (μ) Full Width - Half Maximum

| Sensor | Band 1 Plot Data | Band 2 Plot Data | Band 3 Plot Data | Band 4 Plot Data | Band 5 Plot Data | Band 6 Plot Data | Band 7 Plot Data | Band 8 Plot Data |
|---|---|---|---|---|---|---|---|---|
| TM | 0.45-0.52 | 0.52-0.60 | 0.63-0.69 | 0.76-0.90 | 1.55-1.75 | 10.4-12.5 | 2.08-2.35 | N/A |
| ETM+ | 0.45-0.52 | 0.53-0.61 | 0.63-0.69 | 0.78-0.90 | 1.55-1.75 | 10.4-12.5 | 2.09-2.35 | .52-.90 |

For instance, band 2 of the LANDSAT 7 version of the TM sensor (called ETM+) has wavelength limits of 0.53-0.61 μm, band 3 has limits of 0.63-0.69 μm, and band 4 has limits of 0.78-0.90 μm. When mapping total phosphate concentrations with LANDSAT 7 data, it had to be determined which or how many of bands 1-5 and 7 (which have 30-m spatial resolution and relatively narrow spectral bands, as opposed to the 60-m spatial resolution of band 6 and the relatively wide band-width of the 15-m-resolution band 8) to use. A mathematical procedure (multiple regressions) was applied to seek the best combinations of those bands to correlate with the target total phosphate concentration.

It was determined that the use of the single band radiances (even if they were reduced to spectral reflectances from theoretical atmospheric models) as inputs to this procedure, the resulting algorithm would not be very robust (i.e., repeatable under different solar illumination and atmospheric conditions). Therefore, spectral ratios (ratios of spectral bands, after empirical correction for atmospheric haze through a process referred to as "dark object subtraction," were input to the mathematical procedure for each pixel from which a water sample had been collected. These 15 non-reciprocal ratios (R21, R31, R32, R41, . . . R75) became the dependent variables and total phosphate concentration became the independent variable, which was the result of lab analysis of the water samples. The best subsets of spectral ratios were determined, and then the ones with the highest R2 (Adjusted) values were tested to see if they passed the Durbin-Watson test. The model with the highest R2 (Adjusted) that also passed the Durbin-Watson test was the model that was considered to be the best.

Figure 2:
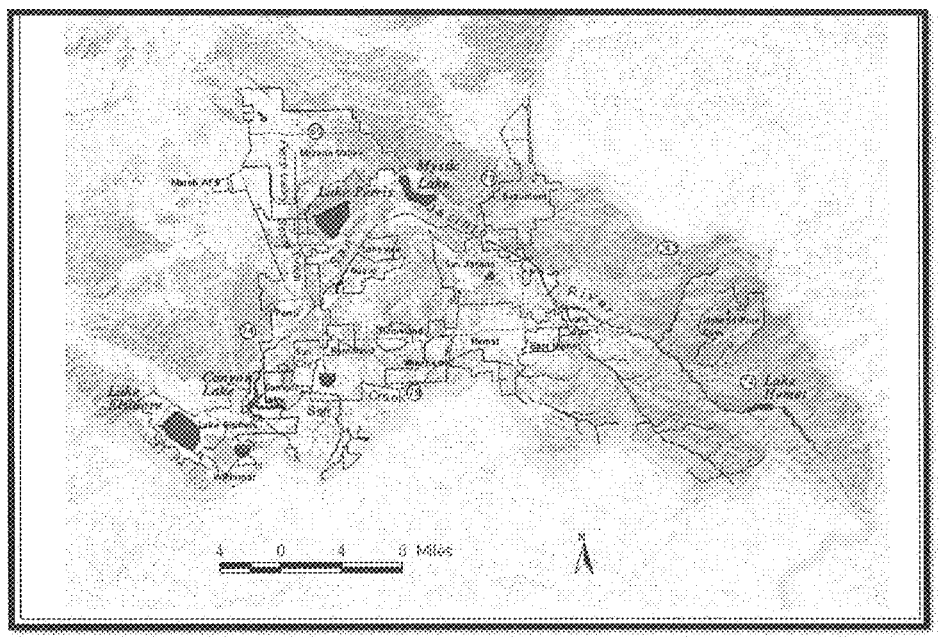
FIG. 2 shows the San Jacinto River Watershed; Lake Elsinore is located in the southwest corner (modified from Li, 2004).

Powerful remote sensing techniques have become available in the last two decades that facilitate practice of the Study Area Lake Elsinore is located in the far western portion of Riverside County, California, 60 miles southeast of Los Angeles. The city of Lake Elsinore is established on its northeastern shore (FIG. 2). It is the largest, and one of the few, natural freshwater lakes in southern California, and is widely used for recreational activities (Kirby, et al. 2004). The lake has a large surface area, but is relatively shallow throughout most of the year. The average depth of the lake is about 24.7 feet, with a surface area of 3,500 acres. The amount of average annual evaporative loss in the area is 56.2 inches while annual average precipitation is only 11.6 inches (Montgomery & Watson, 1997). Due to these imbalanced numbers, the lake can reach extremely shallow levels, and hit a completely dry period during the 1950s and 60s (Li, 2004). Only in extremely wet years is the lake high enough to overflow. When this occurs, the lake flows into Temescal Creek (Temescal Wash.) and can occasionally flood the city of Lake Elsinore. This is a rare event, and has only happened seven times in the last century. The lake levels have been steadily declining since 1998, and are now monitored and replenished with recycled water (Li, 2004).

The lake is situated at the lowest point within the San Jacinto River watershed of approximately 782 square miles. Over ninety percent of the watershed (735 square miles) drains into a reservoir named Canyon Lake. Canyon Lake was formed in 1928 by the construction of the Railroad Canyon dam (Li, 2004). It is located five miles upstream from Lake Elsinore to the northeast. Canyon Lake rarely overflows to Lake Elsinore, only doing so during consistently wet years (Li, 2004). Most watershed runoff never reaches Lake Elsinore, as Canyon Lake is the main receiver, though the lake is the terminus for the San Jacinto River, which passes through urban and agricultural regions within the lower portions (Li, 2004).

Tectonic Setting

Figure 3:
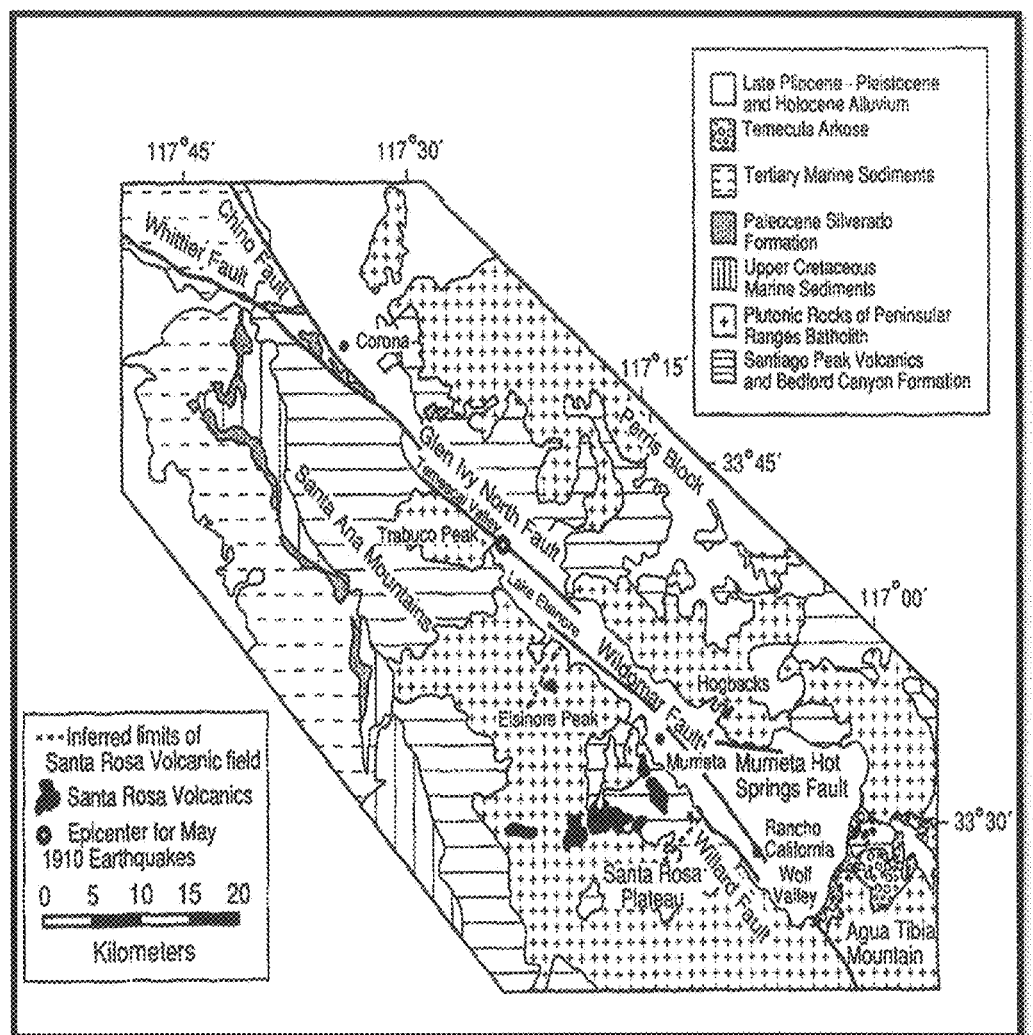
FIG. 3 shows a geological map displaying the region and various faults that are surrounding Lake Elsinore. The lake basin is wedged between the Santa Ana Mountains and the Perris block, as shown here. The four major faults in this area are the Glen Ivy North fault, the Wildomar fault, the Willard fault, and the secondary Murrieta Hot Springs fault (Hull & Nicholson, 1992).

Lake Elsinore sits in a basin bordered to the southwest and west by the Elsinore Mountains, which are part of the Santa Ana Mountain Range. It is a structural depression sandwiched between the Perris tectonic blocks and the Santa Ana Mountains (Hull & Nicholson, 1992; FIG. 3). It is located in a deep, down-faulted graben along the Elsinore fault (Diamata & Lee, 1986). Like many of the other major structural trends in southern California, the lake basin has straight sides and is longer in the northwest direction, as a direct result of faulting (Mann, 1951). The Elsinore Valley represents the northwest surface expression of the trough. The topographic relief of this area is between 373 meters and 1,736 meters in the mountains (Diamata & Lee, 1986).

The Elsinore fault zone is a branch of the San Andreas fault zone, which is situated to the north and northwest of the lake (Hull & Nicholson, 1992). Closer to the lake the fault zone is composed of four major faults: the Glen Ivy North fault, the Wildomar fault, the Willard fault, and the secondary Murrieta Hot Springs fault (Hull & Nicholson, 1992). FIG. 3 shows these faults in relation to Lake Elsinore.

The Glen Ivy North fault compromises the northeast boundary of the trough, mainly characterized by right-slanting movement, with the southwest side down to the northeast (Diamata & Lee, 1986). The Wildomar fault makes up the southwest boundary with a near vertical fault plane that has had right lateral displacement larger than 4.8 kilometers. The Willard fault is further southeast and is characterized by a high-angle, normal fault plane that is dipping to the east (Diamata & Lee, 1986). There are a few other important faults that are also bordering the trough, including the North Elsinore fault and a cross fault. While much is known about these fault systems bordering the trough, within the trough the fault structure is very complex. It has been suggested that there may be as many as eight en echelon fault blocks within the trough, but there is little known about this (Diamata & Lee, 1986).

Regional Bedrock

The entire drainage area of Lake Elsinore basin is mainly composed of three areas. Intermediate plutonic rocks lie to the southwest of the lake and comprise the bedrock in this area. There are a few metamorphic rocks in this region as well, that are mainly quartzite (Mann, 1951). To the north and west of the lake are several different metamorphic rocks: metasediments, predominately slates, quartzite, and meta-andesite, with a few exposed plutonic rocks (Mann, 1951). The part of the drainage basin which is a tributary of the San Jacinto River contains large areas of plutonic and metamorphic rocks, as well as many large dikes of aplite and pegmatite (Mann, 1956).

Stratigraphy of Sediment

The total amount of sediment thickness underlying Lake Elsinore is estimated to be between 600-1,000 meters (Hull & Nicholson, 1992). The sediments at the bottom of the lake are mainly composed of two different types. In the delta of the shallower southern portion of the lake lies compacted micaceous sand (Mann, 1956). These deltaic sands gradually form into finer grained sediments of greenish or black mud once the sand transitions into the flat bottom of the delta. Most of the mud is poorly sorted and consists of clay-sized particles.

The lake shore sediment can be closely correlated with the rocks of the backing terranes, as attested by the grain size distribution and mineral content. These sediments have been split into three zones, based on these relationships (Mann, 1951). Zone A consists of the southwest shore. In this zone there are well sorted sands, which came from the intermediate plutonic rocks and quartzite of the Elsinore Mountains. The percentage of heavy minerals in this location averages about twenty four percent, including hornblende, chlorite, biotite, and zircon.

Zone B, the northeastern and western shore, consists of sediments derived from metamorphic rocks. The pebbles here are rounded from the waves on the beach. There is an alteration between these pebbles and sandy streaks on the northeast portion, and the wave activity is apparent, due to the removal of fine-grained material. The heavy minerals in this location are of a more plutonic facies, including andalusite, kyanite, and garnet. The percentage of heavy metals in this area averages fourteen percent (Mann, 1951).

Zone C consists of deltaic sediments. In the portion that has torrential flow, the lobes of the delta are higher and contain coarser, poorly sorted material. These sediments resemble the metamorphic beach sediment, except that the finer material has not been removed. In certain parts, where the deposition occurred at times of lower flow, the sorting is much better. The heavy minerals and percentages in this zone mirror that of zone B, as well as an addition of grains of pegmatite minerals (Mann, 1951).

Deposition

A majority of the sediment deposited into Lake Elsinore is derived from the Elsinore Mountains, especially during extreme precipitation events (Kirby, et al, 2007). It is important to note that the deposition of sediment into the lake has changed throughout time. A test done by Kirby concluded that the average pre-twentieth century sedimentation rate of 3.8 mm a year is more than three and a half times lower than the average twentieth century sedimentation rate. This is thought to be the result of urbanization, which has raised the rate of direct sediment run-off into the lake, by increasing the percentage of impervious surfaces (Kirby, et al. 2004).

Lake Elsinore Nutrient TMDL

Excessive algal blooms and fish kills have been reported in Lake Elsinore since the early 20$^{th}$ century (Li, 2004). In 1994, the Santa Ana Regional Water Quality Control Board placed Lake Elsinore on the 303(d) list of impaired waters due to excessive levels of nutrients. It was listed again in 1998 and 2002 for the following: unknown toxicity, nutrients, organic enrichment/low dissolved oxygen, and sedimentation/siltation. The designated uses and water quality objectives Lake Elsinore has failed to meet (established in 1995) are warm freshwater aquatic habitat (WARM), body contact recreation (REC1), non-body contact recreation (REC2), and wildlife habitat (WILD) (Li, 2004).

In 2000, the "Lake Elsinore Nutrient TMDL Problem Statement" was prepared and stated that the main problem in the lake was hyper-eutrophication. This condition is due to excessive nutrient input, mainly phosphorous and nitrogen, which results in high algal productivity and algae blooms (Li, 2004). Dead zones and depleted dissolved oxygen are caused by algal respiration and decay, which can result in fish kills. These algal blooms also cause high turbidity in the lake and negatively impact the recreational aspect of the water body. It appears that most of these fish kills correlate with either very shallow lake levels or high watershed flows due to heavy rainfall (Li, 2004). In March of 2004, the Lake Elsinore and Canyon Lake Nutrient TMDL was completed and was incorporated into the Water Quality Control Plan for the entire Santa Ana River Basin in December of that same year. Table 2 shows proposed indicators and numeric targets for Lake Elsinore TMDL (Li, 2004). Table 3 shows proposed final TMDL, wasteload and load allocations for Lake Elsinore, no later than 2015 (Li, 2004). In the following September, the U.S. EPA approved this new resolution, and in 2006 an entire TMDL Task Force was developed to focus on Lake Elsinore and Canyon Lake (Lake Elsinore & San Jacinto Watersheds Authority, 2006). In this same year a Nutrient TMDL Monitoring Plan was submitted to the California Regional Board by the Lake Elsinore and San Jacinto Watersheds Authority, which are a large part of the TMDL Task Force. Monitoring of Lake Elsinore and Canyon Lake has been continuous, with an annual water quality report released each year (Lake Elsinore & San Jacinto Watersheds Authority, 2006). Table 4 presents this data and shows Lake Elsinore Annual Water Quality Summary from Jul. 1, 2009 to Jun. 30, 2010. The TMDL parameters and numeric objectives are listed; each parameter is not meeting its target objective. Note that the Chlorophyll-α summer mean is much higher than the target average (63.5 μg/L above 2015 target, 76.2 μg/L above 2020 target) (modified from Lake Elsinore and Canyon Lake Nutrient TMDL Task Force, 2010).).

TABLE 2

| Indicator | Target Value[c] | Reference |
|---|---|---|
| Total P concentration (interim)[a] | Annual average no greater than 0.1 mg/L; to be attained no later than 2015 | 25th percentile of Lake Elsinore monitoring data (2000-2001 considered as reference state of Lake Elsinore) |
| Total P concentration (final)[a] | Annual average no greater than 0.05 mg/L; to be attained no later than 2020 | Model results discussed in Section 4.0 |
| Total N concentration (interim)[a] | Annual average no greater than 1 mg/L; to be attained no later than 2015 | A ratio of total N to total P of 10 is used to maintain the nutrient balance. |
| Total N concentration (final)[a] | Annual average no greater than 0.5 mg/L; to be attained no later than 2020 | As above |
| Chlorophyll a concentration (interim)[b] | Summer average no greater than 40 μg/L; to be attained no later than 2015 | 25th percentile of Lake Elsinore monitoring data (2000-2001 considered as reference state of Lake Elsinore) |
| Chlorophyll a concentration (final)[b] | Summer average no greater than 25 μg/L; to be attained no later than 2020 | Eutrophic condition (USEPA, 1990, 1999) |
| Dissolved oxygen concentration (interim)[b] | Depth average no less than 5 mg/L; to be attained no later than 2015 | Water quality objective in the Basin Plan |
| Dissolved oxygen concentration (final)[b] | No less than 5 mg/L 1 meter above lake bottom and no less than 2 mg/L from 1 meter to lake sediment: to be attained no later than 2020 | Water quality objective in the Basin Plan |

TABLE 3

| | Lake Elsinore | | | | | |
|---|---|---|---|---|---|---|
| | Phosphorus Load Allocation (kg/yr) | Existing TP Load (kg/yr) | Reduction (%) | Nitrogen load Allocation (kg/yr) | Existing TN load (kg/yr) | Reduction (%) |
| TMDL | 28,584 | 48582 | 41 | 246,530 | 271,206 | 9 |
| WLA | 3,845 | 15007 | | 7,982 | 60,138 | |
| Supplement water** | 3,721 | 14883 | 75 | 7,442 | 59,532 | 88 |
| Urban | 124 | 124 | 0 | 540 | 606 | 11 |
| CAFO | 0 | 0 | | 0 | 0 | |
| LA | 21,969 | 33575 | | 210,849 | 211,068 | |
| Internal Sediment Source | 21,554 | 33160 | 35 | 197,370 | 197,370 | 0 |
| Atmospheric Deposition | 108 | 108 | 0 | 11,702 | 11,702 | 0 |
| Agriculture | 60 | 60 | 0 | 330 | 371 | 11 |
| Open Forest | 178 | 178 | 0 | 505 | 567 | 11 |
| Septics | 69 | 69 | 0 | 942 | 1,058 | 11 |
| CL watershed | 2,770 | | 27,699 | | | |
| MOS | 0 | | | 0 | | |

TABLE 4

Lake Elsinore Annual Water Quality Summary
(June 1, 2009-June 30, 2010)

| Parameter | Basin Plan Objectives (Includes TMDL Targets) | Date TMDL Objective to be Attained | Number of Sampling Events | Range of Daily Averages | Annual Mean |
|---|---|---|---|---|---|
| Dissolved Oxygen (mg/L) | Not less than 5 mg/L as a depth avg. | 2015 | 21 | 0.3-8.7 | 5.3 |

TABLE 4-continued

Lake Elsinore Annual Water Quality Summary
(June 1, 2009-June 30, 2010)

| Parameter | Basin Plan Objectives (Includes TMDL Targets) | Date TMDL Objective to be Attained | Number of Sampling Events | Range of Daily Averages | Annual Mean |
|---|---|---|---|---|---|
| Total Nitrogen (mg/L) | Not less than 5 mg/L 1 meter above lake bottom | 2020 | 21 | 0.2-6.9 | 3.7 |
| Total Phosphorus (mg/L) | Annual average 0.1 mg/L | 2020 | 20 | 0.12-0.32 | 0.19 |
| Chlorophyll-a (µg/L) (April to Sept.) | Summer avg. no greater than 40 µg/L | 2015 | 12 | 44.7-161.7 | 103.5 (summer mean) |
|  | Summer avg. no greater than 25 µg/L | 2020 | 12 | 46.0-150.3 | 101.2 (summer mean) |

Materials and Methods

All satellite data used in this study is from the LANDSAT Thematic Mapper (TM) satellite sensor. This satellite sensor provides satellite images dating back to 1982 and has seven individual spectral bands: 1-3 being in the visible, 4 in the Near Infrared (NIR), 5 and 7 in the Short Wavelength Infrared (SWIR), and band 6 in the Thermal Infrared (TIR) (Vincent, 1997). These bands, except for band 6 which measures heat, measure the amount of reflected sunlight from the earth's surface and produce pixels that contain Digital Numbers (DNs) representing the amount of reflected sunlight (electromagnetic radiation) at each pixel (Vincent, 1997). Data from both LANDSAT 5 and 7 (L5 & 7) were downloaded for free from the USGS Global Visualization Viewer program (http://glovis.usgs.gov/).

The Santa Ana Watershed Project Authority (SAWPA) provided an excel file of water measurement data from Jun. 12, 2002 to Jun. 30, 2010, with 29 different lab measurements and eight different field measurements. These measurements include the four TMDL listed impairments which were targeted: chlorophyll-α, total phosphorus, total nitrogen, and dissolved oxygen. It also includes turbidity, which is another important indicator that has proven to be measureable from satellites. These measurement data were used to create, test, and analyze different satellite algorithms.

There were other small contributions of data from a few different sources involved in the water management of Lake Elsinore. Lake water levels were sent by the Elsinore Valley Municipal Water District. MWH Global, a consultant dealing with Lake Elsinore from 2006 to 2010, responded with additional requested data and answers to questions about in situ measurements.

Dr. Robert K. Vincent of Bowling Green State University contributed some of his satellite algorithms, a majority of which were created on Lake Erie water quality data, to see if they may be applicable to Lake Elsinore water quality data. These algorithms include turbidity, low and mid-range total phosphorus, and low and high bloom phycocyanin. Blue Water Satellite Inc. provided chlorophyll-α results of previous work completed on Lake Elsinore, including a working algorithm.

All work involving satellite remote sensing was completed with Intergraph Earth Resource Mapper 7.2 and ArcMap 9.3.1 software packages.

All statistical analysis was completed with Minitab 15 Statistical Software and Microsoft Excel.

Data Exploration

Water Quality measurement data was provided by SAWPA that ranged from August of 2002 to June of 2010. LANDSAT overpasses for satellites 5 and 7 occur every 16 days, but are 8 days out of phase, such that the repeat cycle, using both satellites, is every 8 days, with L5 and L7 alternating every cycle period for the same frame center. The frame center that contains Lake Elsinore is Path 40 Row 37, with the coordinate system being NAD83 UTM 11N and the datum being WRS 84. Satellite overpass dates were sought through the USGS Global Visualization Viewer from August, 2002 to June, 2010, that fell on the same days that water samples had been collected in Lake Elsinore. The images for these "correlation" dates were downloaded and natural color images were examined for problematic cloud cover using ER Mapper. In total, there were 16 overpass dates that correlated with water quality sample dates, free of any problematic cloud cover. Table 5 shows satellite overpass dates with non-problematic cloud cover that occurred on the same day as in situ data collection. Note the variation in stations over time. 11 of these satellite images were from L5, while five of them were from L7.

TABLE 5

| Dates | Satellite | Image Cloud Cover | In Situ Stations Collected |
|---|---|---|---|
| Aug. 28, 2002 | LANDSAT 5 | 0% | LE1-10 |
| Feb. 4, 2003 | LANDSAT 5 | 30% | LE1-13 |
| Apr. 19, 2004 | LANDSAT 7 | 0% | LE2, 3, 6, 8-13 |
| Jun. 14, 2004 | LANDSAT 5 | 10% | LE2, 3, 6, 8-13 |
| Aug. 9, 2004 | LANDSAT 7 | 0% | LE2, 3, 6, 8-13 |
| Oct. 4, 2004 | LANDSAT 5 | 33% | LE2, 3, 6, 8-13 |
| Feb. 9, 2005 | LANDSAT 5 | 0% | LE2, 3, 6, 8-13 |
| Jul. 27, 2005 | LANDSAT 7 | 0% | LEB3-4, LEPU |
| Apr. 25, 2006 | LANDSAT 7 | 59% | LEE1-3 |
| Jun. 20, 2006 | LANDSAT 5 | 0% | LEE1-3 |
| Jul. 6, 2006 | LANDSAT 5 | 0% | LEE1-3 |
| Mar. 5, 2008 | LANDSAT 5 | 42% | LEE1-3 |
| Mar. 21, 2008 | LANDSAT 5 | 0% | LEE1-3 |
| May 16, 2008 | LANDSAT 7 | 0% | LEE1-3 |
| Aug. 20, 2008 | LANDSAT 7 | 0% | LEE1-3 |
| Mar. 24, 2009 | LANDSAT 5 | 0% | LEE1-3 |

Each water collection date had several different stations at which the varying parameters were measured. For various dates, different stations had water sample collections, and for some stations only certain parameters were measured. For example, there may be "no data" for turbidity for a set of stations on one date, and only total phosphorus measurements. Another year might have the opposite. Also, certain stations were used in the earlier years of collection, like 2002 and 2003, that seemed to be phased out during later years of collection. For the last few years, measurements were only collected at a maximum of three stations, spatially distributed across the lake. The water quality measurements for the different parameters were retrieved from the master SAWPA TMDL database, for each sample collection date that matched with a satellite overpass date. Some measurements, such as total phosphorus, needed to be averaged, as a number of different readings for the measurement were taken. Each parameter was designated its own Microsoft Excel Spreadsheet.

Figure 4:
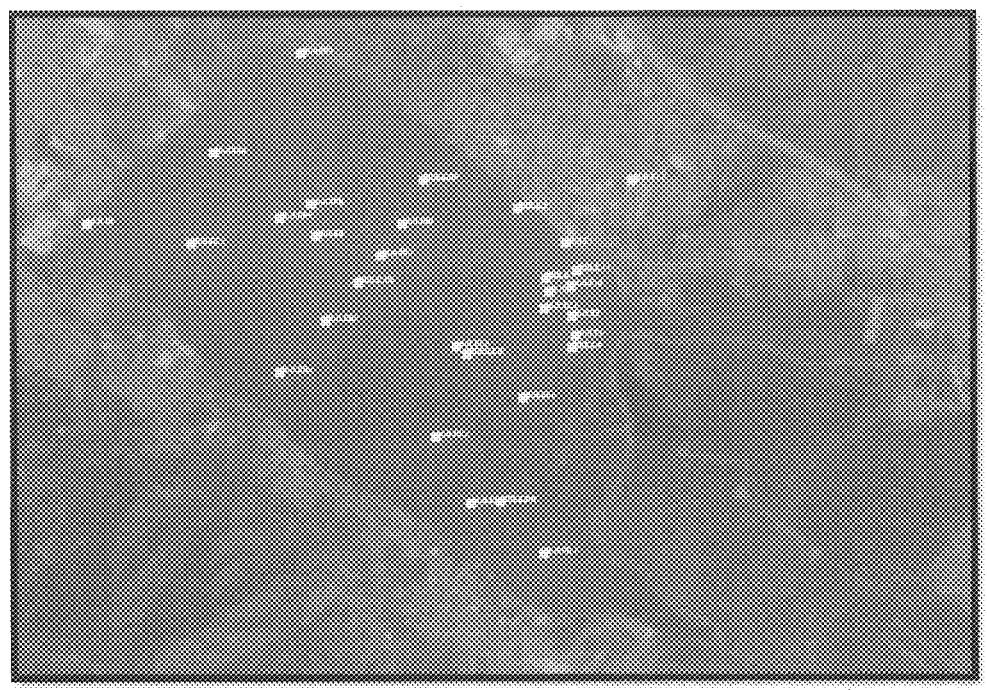
FIG. 4 shows a pseudo-color image of Lake Elsinore with designated sampling station vector file overlaid to display station distribution. Image is from L5, overpass date Feb. 9, 2005.
Figure 5:
FIG. 5 shows an example of a "cell values profile", displaying the reflectance values for each band at a chosen pixel that contains a station. Band 6, which represents thermal data, was not used.

The coordinates for each station were provided by SAWPA as an ArcMap GIS shapefile. These stations were imported into ER Mapper as a vector file and displayed under the correct coordinate system, NAD83 UTM 11N, with Datum plane WRS 84 (FIG. 4). This vector file was then overlaid onto each satellite image, so that each station around Lake Elsinore was viewable. For each image the DNs were extracted for each measured station for that collection date. This was done by viewing the frame as a pseudo color image of one spectral band, so that the DNs of all seven bands were displayed in the ERMAPPER "View Cell Values Profile" selection (FIG. 5). Each station was closely examined by using the "software zoom tool", to clearly center on the pixel containing the station under examination. The DNs for each band (except band 6, the thermal band) for this specific pixel were extracted using the "View Cell Values Profile" and recorded.

The DNs for each band, for each image now needed to be dark object corrected. The dark object is one less than the minimum DN value, which is the darkest pixel for each band within each image. By correcting each DN for the dark object differences, atmospheric haze and additive electronic offset of the satellite senor are removed (Vincent, 1997). The minimum DN values for each band are found by searching a histogram of each band, accomplished by a "calculate statistics" function within ER Mapper for a large subset each image that excludes the corners and edges of the frame, where noise pixels can masquerade as real data. Each band was dark objected corrected for each image, after the dark objects were found.

The shadow and slope effect is another factor that needs to be canceled out for each image. This factor refers to the amount of brightness and shadow from topographic differences that vary from pixel to pixel, which in the case of water are waves causing sporadic sun glint by waves from wind and water currents. By using spectral ratios, this factor is minimized, and only chemical composition (volume reflectance for water) is left as the dominating element (Vincent, 1997). Spectral ratios were calculated by dividing each band by each other lower wavelength band, until all the pairs were complete (ratio 2/1, ratio 3/1, ratio 3/2 . . . ). DNs, dark objects, dark object corrected DNs, and all possible spectral ratios were compiled into each TMDL parameter Microsoft Excel spreadsheet, containing the collection dates, LANDSAT satellite (5 or 7), collection station, and the in situ measurements for that parameter.

Preexisting Algorithm Exploration

Data analysis was first completed on preexisting algorithms, to see if these algorithms could accurately predict the in situ data for Lake Elsinore. The low range total phosphorus algorithm, which was created on L5, in the western frame of Lake Erie (Path20Row31), for Jul. 13, 2007, was constructed on a data range of measurements that was much smaller (0.010 to 0.100 ppm) than the in situ total phosphorus measurements of Lake Elsinore (Vincent, 2009). Since none of the Lake Elsinore measurements were this low, this algorithm could not be used on such a nutrient-laden lake. The mid-range total phosphorus algorithm was created on L5, in the Cleveland frame of Lake Erie (Path19Row31) for Aug. 4, 2006, on data ranging from 0.128 to 0.292 ppm (Vincent, 2009). Most of the Lake Elsinore total phosphorus data extended beyond that, also, with average measurements of 0.4 to 0.7 ppm, and a few reaching 4.0 ppm, but there was a small amount of data that did fall within this range, for the algorithm to be applied to.

A low range turbidity algorithm created on L7, in the Toledo frame of Lake Erie (Path20Row31) for Jul. 1, 2000, was originally trained on turbidity measurements that did not exceed around 15 NTU. This algorithm employs one ratio of band 3 divided by 2 (R3/2), which is used to target iron content, and in this case, turbidity containing dirt and mud (Vincent et al., 2004). Again, most turbidity measurements for Lake Elsinore were out of this data range, with a majority measuring 30 NTU and a few up to 85 NTU, but there was a small data set that did fall within this range and the algorithm was applied to this data.

Previous work completed by Blue Water Satellite Inc. (BWSI) to target chlorophyll-α and develop an algorithm was provided by the company (BWSI, 2010). The scatter plot showing the correlation results is displayed within the results section. This algorithm and provided data were also used to process images and to look for further correlations with other parameter data, especially dissolved oxygen.

The low and high bloom phycocyanin algorithms, which are extensively researched and applied under a NOAA grant at BGSU, were used to process images and view correlations with other parameters (Vincent, 2009). Unfortunately this algorithm could not be examined for correlation accuracy, because there are no phycocyanin in situ measurements from Lake Elsinore. The purpose of these algorithms is to target cyanobacteria, also called harmful algal blooms, which have been documented as being present in the lake throughout much of the year. (Lawson & Anderson, 2007). A past study revealed that cyanobacteria compromised 75.2% of the total number of phytoplankton at one site of the study, including the strain Aphanizomenon, which has been found to produce neurotoxins (Oza, 2003).

Algorithm Development

Several different algorithms were created for various Lake Elsinore TMDL parameters that are currently being monitored. These include total phosphorous, turbidity, and total nitrogen. The 15 different spectral ratios for each data point were entered as independent inputs, while the targeted in situ measurements for each data point were entered as dependent inputs. The desired amount of total data points (or cases) for algorithm building was 30, which were randomly selected from the all available data points for the targeted parameter by choosing every third point from all the data points. The left over data points were used for a withheld data set for further algorithm accuracy and robustness testing. Sometimes this desired quota could not be met, due to a limited amount of data, or data points that displayed problematic discrepancies and were not chosen to build the algorithm on.

Any data points that presented any factors that may have affected the reflectance values and designation of accurate DNs were not included in the data sets on which the algorithms were constructed. All data points in each image were examined extensively using ER Mapper for any factor that might be problematic. This includes any partial cloud cover within the pixel, data points falling on pixels within a venetian blind error (L7), or if a data point fell on a land pixel. Some of the data points within close proximity to the shore are projected as being on land pixels within some images. This error could be due to slight inaccuracies when collecting the GPS coordinates or these may be grab sample locations from land. Whether these few close to shore data points fell on a water pixel, land pixel, or a combination of both, varied from image to image. This is partially due to the water level Lake Elsinore contained for that collection and satellite overpass date, the amount of shore erosion, and simply how the scene appeared when satellite overpass was occurring. The level of reflectance varies greatly from land to water and therefore any data point containing any pixel that may contain land was excluded. These data points were not included in the data set on which the algorithms were built and applied to, but they were not thrown out completely, and were investigated further after the algorithms were created.

Linear multiple regression best subsets of the data were calculated using Minitab Statistical Software. The combinations of spectral ratios that yielded the highest $R^2$ adjusted were investigated further to reveal the accuracy of the subset. The reasoning for using $R^2$ adjusted as an indicator of an accurate best subset and not $R^2$ is because it is adjusted for the number of terms in the algorithm. $R^2$ is not adjusted and will always increase with additional predictors (spectral ratios) (MINITAB Inc., 2007-2008). Further analysis provided the algorithm for the chosen best subset and a measure of the Durbin-Watson statistic (d) to complete the Durbin-Watson test, which consists of a comparison of d with a lower ($d_l$) and upper ($d_U$) limit of the Durban-Watson statistic. This statistical test is most often used to investigate autocorrelation (correlation of input parameters) in multiple regressions of time series, but has also proven to be useful in examining autocorrelation among multiple spectral band inputs (Vincent et al., 2004). This test can be applied to any regression model that has any type of multiple inputs (Vincent et al., 2004). The algorithms being created were preferred to pass the Durbin Watson test for both positive and negative autocorrelation.

To prove that positive autocorrelation is not present within the algorithm, d must be higher than the designated upper bound statistic ($d_U$). An intermediate value of $d_L<d<d_U$ results in d being indeterminate, while d being less than $d_L$ proves that positive autocorrelation is present. To prove that negative autocorrelation is not present within the algorithm, d is subtracted by 4.0 and must still meet the previous requirements (Durbin & Watson, 1951). These upper and lower bound values depend on the amount of dependent inputs (n) and independent inputs (k) for the algorithm. The k (number of input parameters, in this case dark-object subtracted spectral ratios) and n (number of cases) varied between algorithms, depending on the best subset of ratios that worked (k), and how many data points were collected and lacked any bad factors (n). The study aimed to have around 30 n, because as the n increases, the range that d would be indeterminate narrows (Durbin & Watson, 1951).

After an algorithm was chosen for a parameter, it was then applied to the actual data from the selected data set, inputting the correct spectral ratios to view the linear relationship with the in situ measurements. The same was done for the withheld data set, which is data the algorithm was not created from. A root mean square (RMS) error was calculated for the results of the withheld data set to examine the accuracy of the algorithm. This error represents the measure of spread of the average y value (in situ parameter measurements) around the regression line, which is the line predicting the average in situ parameter measurement associated with a given x value (best subset of spectral ratios). By taking the range of the data in the withheld data set the algorithm was applied to, and dividing the RMS error by this range, a percentage of the error is calculated. Example: Total phosphorus withheld data set ranges from 0.012 mg/L to 0.60 mg/L, so the range for the data set is 0.588. mg/L. If the RMS error is 0.059 mg/L, then this error represents about 10% of the data range, which is low and would indicate the algorithm is useful because there would be about five different levels of the range that could be distinguished within ±one RMS error.

The algorithms were then applied to the entire data set composed of the selected and withheld data sets to view the $R^2$. Lastly, these algorithms were applied to all the possible data points for the corresponding TMDL parameter, including the data points containing any previous listed discrepancies. This sometimes revealed that a factor considered to possibly be problematic, like partial cloud cover, did not appreciably affect the data point's DNs to the point of inaccuracy.

TMDL Parameter Correlation

While the listed TMDL parameters total phosphorus, total nitrogen, and chlorophyll-α were investigated using satellite remote sensing, the fourth impairment, dissolved oxygen, was not expected to be measured or monitored directly by a satellite algorithm, because low dissolved oxygen zones are usually near the bottom of a lake, not the surface. Therefore, a goal of the study was to find a strong correlation between dissolved oxygen and a parameter that can be monitored by satellites. Lake Elsinore is a discontinuous, warm polymictic lake, which means it can thermally stratify for days or weeks at a time, but is in a mixing state for most of the year (Cole, 1994). These stratification events occur during the summer, and can last for a few days or several weeks (Lawson & Anderson, 2007). During these stratification events dissolved oxygen levels are depleted within the lower portion of the water column, due to microbial respiration and the decomposition of dying algal blooms that sink to the bottom. The thermal gradient that has formed prevents mixing of dissolved oxygen from the upper water column into the lower regions. In turn, these anoxic conditions near the sediments can lead to the release of nutrients from the sediments (Lawson & Anderson, 2007). Once the stratification period is over, and mixing occurs, these nutrients are mixed into the upper portion of the water column, fueling algal blooms (Lawson & Anderson, 2007). This creates a cycle of depleting the dissolved oxygen levels once again.

The idea for the correlation of dissolved oxygen was to link the measurements of it with the occurrence of algal blooms within the lake. Stratification and low dissolved oxygen impairments occur during the summer months within Lake Elsinore, therefore, data were examined for the months of June, July, and August. The dissolved oxygen measurements for a majority of the other months show that stratification is not present, and dissolved oxygen levels are mostly consistent at all depths. Also, algal blooms are reported to be the worst during the summer months, and the chlorophyll-α TMDL targets are set for the summer months only, demonstrating that these algal blooms are in part responsible for the dissolved oxygen depletion during this time period (Li, 2004). Phycocyanin is a parameter that is directly associated with algal blooms, and chlorophyll-α can be as well. Total phosphorus is the main nutrient that fuels cyanobacterial blooms and turbidity can be caused by these blooms. Therefore, these parameters were all examined for possible correlations with measurements of dissolved oxygen at different depths and dates.

Correlations were examined among other parameters as well, to view which ones may have relationships with another, lending more information to understanding the water quality of Lake Elsinore. These correlations were examined by constructing linear and multiple regressions and viewing the $R^2$ as an indicator of any possible relationships.

Image Processing

Images were processed using ER Mapper, to create a color scaled image displaying the different levels of each parameter an algorithm was created for. A land mask for each image was first developed, to only include areas of water by designating all land regions with the value "Null." Each algorithm was then applied to the image for each corresponding parameter, using the "formula editor" function within ER Mapper. Each algorithm is simply entered and each band for each ratio is replaced with "INPUT", along with the correct dark object value that is subtracted from each band.

EXAMPLE

Turbidity Algorithm=−85.3+47.7*Ratio3/1−105*Ratio4/2+157*Ratio4/3+31.4*Ratio7/5

ER Mapper Turbidity Algorithm=−85.3+47.7*(INPUT3−DO)/(INPUT1−DO)−105*(INPUT4−DO)/(INPUT2−DO)+157*(INPUT4−DO)/(INPUT3−DO)+31.4*(INPUT6−DO)/(INPUT5−DO)

INPUT1=Band 1
INPUT2=Band 2
INPUT3=Band 3
INPUT4=Band 4
INPUT5=Band 5
INPUT6=Band 7

**The reason Band 7 is replaced with "INPUT6" is because the "INPUTs" must be listed in numerical order (entering INPUT7 would result in an error message). The finalized images were desired to display parts per billion (ppb), so any parameters that were originally created on ppm data (mg/L), were converted using the "formula editor" function. By entering the command "*1000" the data is successfully converted to ppb.

The first three bands of each image were imported to create a composite natural color image within ArcMap. The algorithm images created in ER Mapper were then imported and overlaid onto these natural color images, so that the surface area of Lake Elsinore encompassed the correct algorithm image. Color scales were manually made to display the different interval measurement amounts of the targeted parameter. TMDL exceedance images were also created for various selected scenes, to show which portions of the lake are meeting the desired TMDL parameter target level, and which areas are not.

Results and Discussion: Data Exploration

After reviewing the data points at each collection station for any factors that may affect the designation of accurate reflectance values at each of these pixels, a number of data points were listed as problematic. The majority of these data points were stations that are close to shore, and therefore were captured on a land pixel when satellite overpass occurred. These close to shore data points included stations LE1, LE2, LE8, LE11, LE12, and LEE1. There were a few data points that fell within pixels affected by the venetian blind error of the L7 ETM sensor, as well as a few data points on pixels containing partial cloud cover.

There are 78 individual total phosphorus measurements for 16 different stations over the span of 2002 to 2009, which were collected during satellite overpass. Of these 78 data points, 33 were excluded from the data set on which were chosen to construct a total phosphorus algorithm. For total phosphorus, a few other data points were higher than the data range for the algorithm being created. These stations were all LE13 (4 cases), indicating there may be a discharge pipe or direct source of impairment, resulting in these abnormally high total phosphorus measurements. Only two other data points, LE2 from Apr. 19, 2004 and LEE2 from Apr. 25, 2006, were also out of the data range.

There are 62 individual turbidity measurements for 16 different stations over the span of 2002 to 2009, which were collected during satellite overpass. Of these 62 data points, 16 were excluded from the data set chosen to construct a turbidity algorithm on. Only one of these data points was left out due to being abnormally out of range with a reading of 139 NTU. This was again station LE13, on Jun. 14, 2004. A number of data points that had not been considered for the total phosphorus algorithm data set due to the data being out of range, were within the desired range for the turbidity algorithm and could now be included in the algorithm data set.

There are 86 individual total nitrogen measurements for 16 different stations over the span of 2002 to 2009, which were collected during satellite overpass. Of these 89 data points, 28 points were excluded from the data set chosen to construct a total nitrogen algorithm on. Only one of these data points was left out due to being out of the data range, with a reading of 12.72 ppm at station LE2 on Apr. 19, 2004.

There are 40 individual chlorophyll-α measurements for six different stations over the span of 2002 to 2009, which were collected during satellite overpass. Of these 40 data points, 27 points had been excluded from the data set chosen by BWSI on which to construct a chlorophyll-α algorithm. A majority of the data points BWSI dropped were the same ones excluded from algorithm construction for the other parameters in this thesis, which is most likely due to the same reasons discussed in previous sections.

Preexisting Algorithm Results

Lake Erie High Range Total Phosphorus Algorithm

Figure 6:
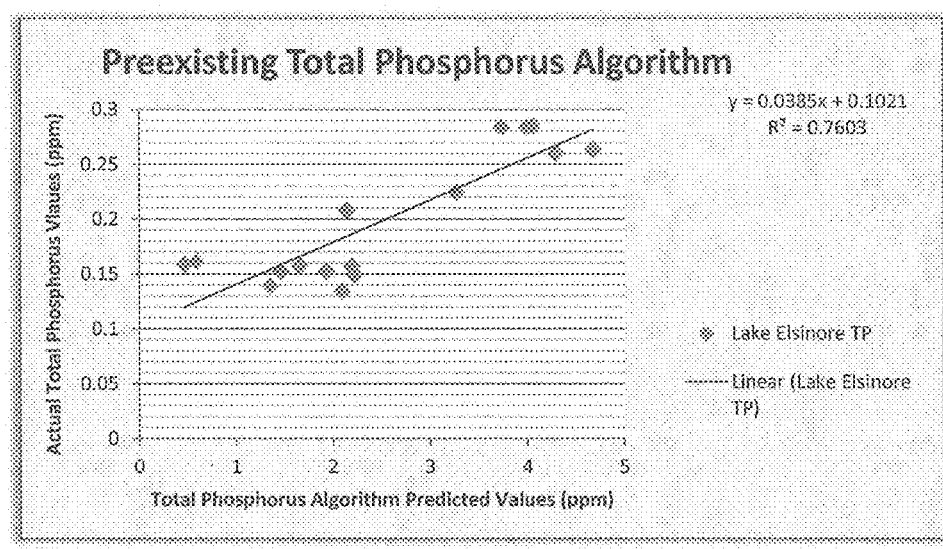
FIG. 6 shows a scatter plot displaying the correlation between in situ measurements of total phosphorus and the 4 ratio preexisting total phosphorus algorithm predicted values. This plot displays a strong correlation with an $R^2$ of 76%. There were no L7 overpass data points within this range.

The preexisting mid-range total phosphorus algorithm, which was originally trained on Lake Erie, exhibited a positive correlation with in situ Lake Elsinore water samples that fell within this algorithms data range. There are 16 data points within this data range, and the scatter plot displays an $R^2$ of 76% (FIG. 6). While there is a strong, positive correlation between the algorithm and the in situ values, the RMS error for the data set is 2.62, which shows the algorithm performed poorly in predicting the actual values. The predicted values are about 1 to 4 ppm higher for each actual value. Inputting the predicted values into the linear equation provided within the scatter plot (y=0.0385x+0.1021), completes a linear transformation, and brings the predicted values down to their correct value, decreasing the RMS error to 0.028. A withheld data set would be needed to test the robustness of using both this algorithm and the linear equation to accurately predict the actual values within Lake Elsinore. Unfortunately, there were not enough points collected within this range to provide a withheld data set.

Using the U.S. EPA system of level II ecoregions, to divide up various North American environments, one can see that the region the algorithm was constructed on (Central U.S.A. Plains), greatly differs from the region the in situ data was collected (Warm Deserts; U.S. EPA, 2011). The fact that the Lake Erie algorithm resulted in some amount of correlation may build on previous evidence that these algorithms can be moved spatially, and still measure actual total phosphorus, without being altered by other constituents.

Total Phosphorus=0.0288+7.55*Ratio5/1−0.675*Ratio5/4−1.96*Ratio7/3+0.394*Ratio7/5

Lake Erie Low Range Turbidity Algorithm

Figure 7:
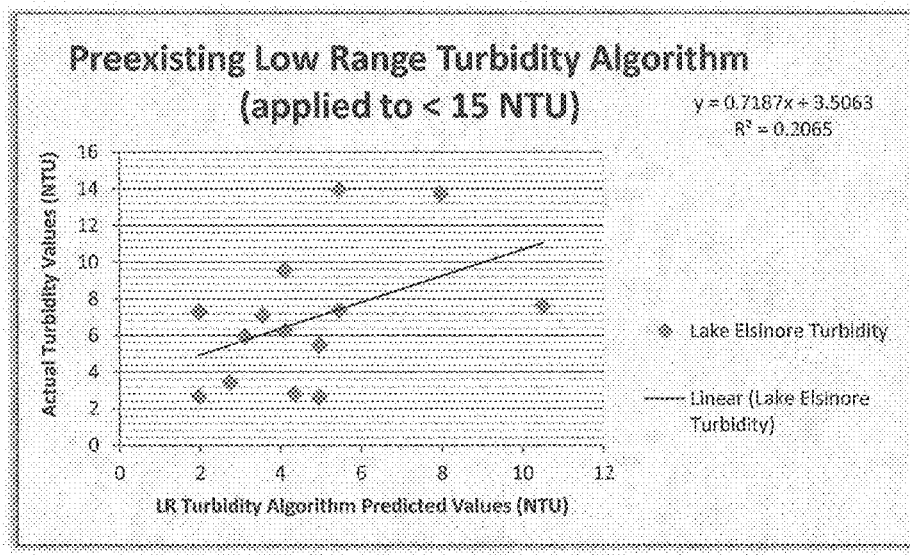
FIG. 7 shows a scatter plot displaying the correlation between in situ measurements of low range turbidity and the 2 ratio Lake Erie low range turbidity algorithm predicted values. This plot displays a weak correlation with an $R^2$ of 21%. There are nine L 5 overpass data points and five L 7 overpass data points within this range.

The preexisting low range turbidity algorithm that was originally trained on Lake Erie displayed weaker correlations with in situ Lake Elsinore water samples that fell within this algorithm's original data range. When applying the turbidity algorithm to the original data range it was trained on (not exceeding 15 NTU), the correlation was poor, with an $R^2$ of 21% (FIG. 7). There are 14 data points within this algorithms data range. The main target of the algorithm is mud and dirt containing iron that results in muddy turbid waters (Vincent et al. 2004). The algorithm may have performed poorly due to a lack of this type of turbidity within Lake Elsinore, as well as the amount of algal blooms that mask this sediment run off, and are the main culprits for the high levels of turbidity within Lake Elsinore.

$$Turbidity=-17.2+27.7*Ratio3/2$$

Lake Elsinore Chlorophyll-α Algorithm

Creating chlorophyll-α algorithms can be tricky and past attempts have displayed difficulties, due to the fact chlorophyll-α is insoluble in water. The pigment is trapped within plants, which makes this a much more difficult variable to measure. The water sample collection techniques also affect the amount of correlation with satellite remote sensing methods. The extractive method to measure the pigment is one that throws off correlation. This involves extracting the pigment from the water sample itself, and measuring the chlorophyll-α without being within the lake water (which would be in vivo; U.S. EPA, 2000). The results from this method are difficult to correlate with satellite remote sensing, due to the separation of the pigment from the lake water the satellite is measuring it in.

Figure 8:
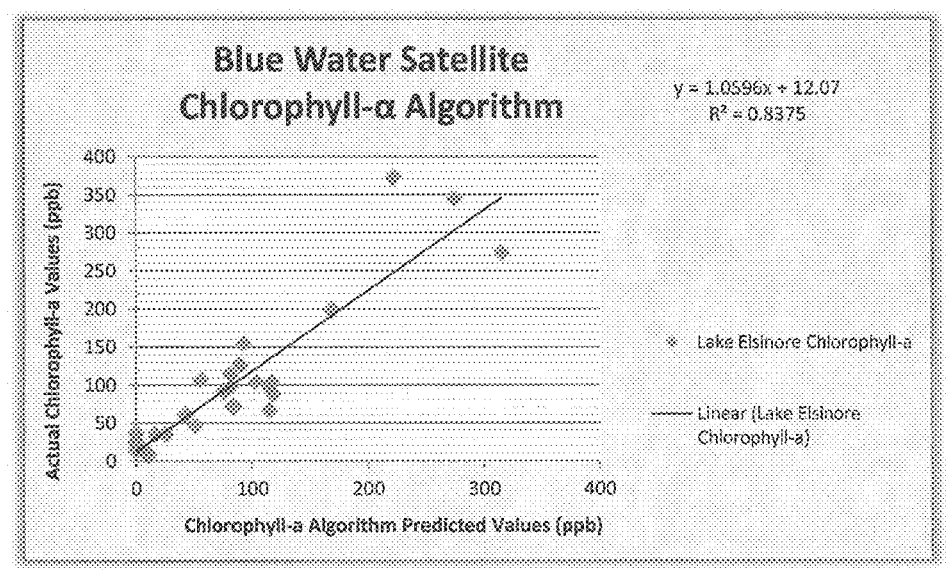
FIG. 8 shows a scatter plot displaying the correlation between in situ measurements of chlorophyll-$\alpha$ and the BWSI 6 ratio chlorophyll-$\alpha$ algorithm predicted values. This plot displays a strong correlation with an $R^2$ of 84%. This data set included 16 L5 overpass data points and 11 L7 overpass data points.

Previous work with Lake Elsinore, aimed at targeting chlorophyll-α levels within the lake, was completed by BWSI, a company based out of Bowling Green, Ohio (BWSI, 2010). The algorithm was applied to 27 data points and resulted in a strong correlation with an $R^2$ of 84% (FIG. 8). Exploration was completed to see if a better algorithm may be possible with the provided data, but the BWSI algorithm stands to be the strongest. This could be due to the reasons described above, as the method for chlorophyll-α measurements on Lake Elsinore is extractive (Li, 2004).

$$Chlorophyll-\alpha=-740-494*Ratio3/1+933*Ratio4/1+560*Ratio5/4-543*Ratio7/1-277*Ratio7/3+533*Ratio7/5$$

Low and High Bloom Phycocyanin Algorithms

Unfortunately there are no in situ measurements of phycocyanin with which to correlate the phycocyanin algorithm predicted values. The purpose of involving these two algorithms within this study is to process the images to view phycocyanin levels within the lake, and to use the predicted values to view correlations. The low bloom algorithm was trained on a data range of phycocyanin in situ values that did not surpass 18 ppb. This algorithm rendered all negative values, when applied to the data, signifying the levels of phycocyanin within the lake are most likely out of its range. Cyanobacteria has been reported as prevalent within the lake, even throughout the entire year, so the fact the levels of phycocyanin within the lake are higher than the low bloom range is not surprising. This goes along with the other high levels of parameters within the water body, representing a hypereutrophic environment (Carlson, 1996).

Attention was turned to the high bloom phycocyanin algorithm, which has a data range of around 18 to 80 ppb. The predicted values from L5 for this algorithm were under scrutiny, as a recent paper discusses problems with L5 values from the phycocyanin bloom algorithms, and that it is giving different results from L7 (Wicks, 2011). This algorithm was created on data solely from L7, and seems to be somewhat restricted to this satellite without applying corrections to L5. Reflectance values from the same pixel on almost similar dates do not match between L5 and L7 (Wicks, 2011). Correlations were created within this previous study to correct the L5 values to match the L7 values for the Lake Erie region (Wicks, 2011). While these corrections were applied to the L5 predicted values, these correlations might be restricted to the locality they were created. Correlations displayed in later sections of this thesis show that the L7 predicted values from the high bloom algorithm follow the rest of the results within this study, and when including L5 predicted values the results are completely different. This lends more evidence that these satellite corrections may not be robust. Correlations were tried using the L5 predicted values, but are not displayed due to the problematic evidence.

Algorithm Development Results

New algorithms for Lake Elsinore were created for the following parameters: total phosphorus, turbidity, and total nitrogen. While the first two of these parameters proved successful, total nitrogen proved difficult for which to create a strong algorithm.

High Range Total Phosphorus

Figure 9:
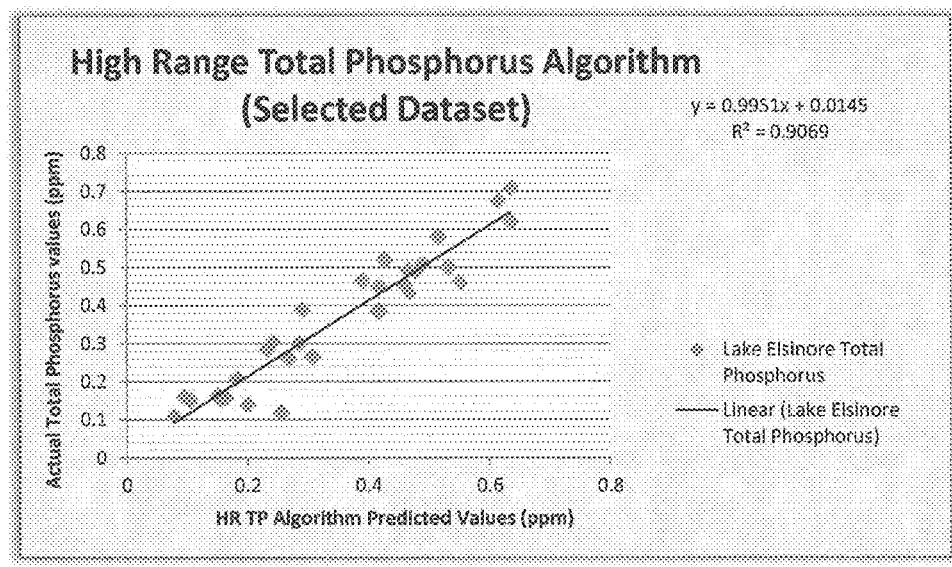
FIG. 9 shows a scatter plot displaying the correlation between the selected data set in situ measurements of total phosphorus and the 6 ratio high range total phosphorus algorithm predicted values. This plot displays a strong correlation with an $R^2$ of 91%. There are 23 L5 and only seven L7 overpass data points within this data set.
Figure 10:
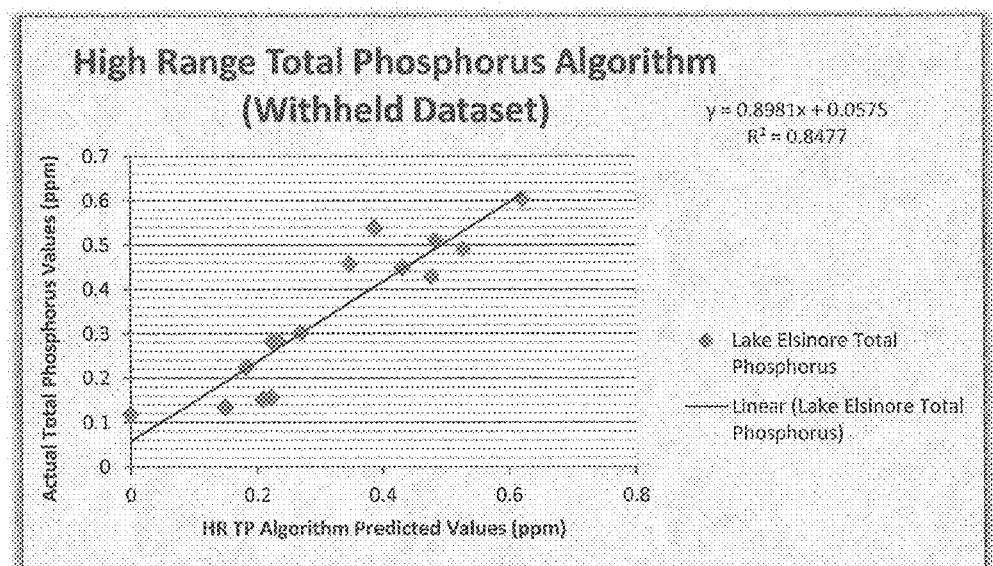
FIG. 10 shows a scatter plot displaying the correlation between the withheld data set in situ measurements of total phosphorus and the 6 ratio high range total phosphorus algorithm predicted values. This plot displays a strong correlation with an $R^2$ of 85%. There are 11 L5 and four L7 overpass data points within this data set.
Figure 12:
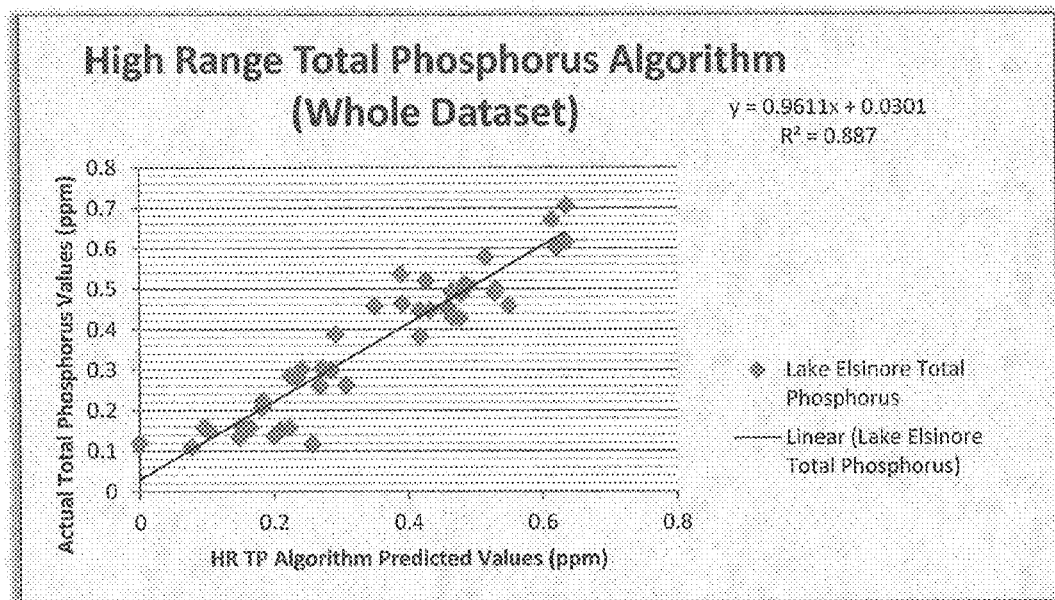
FIG. 12 shows a scatter plot displaying the correlation between the whole data set in situ measurements of total phosphorus and the 6 ratio high range total phosphorus algorithm predicted values. This plot displays a strong correlation with an $R^2$ of 89%. There are 34 L5 and 11 L7 overpass data points within this data set.

The data range for the algorithm is also a large range, and should cover most eutrophic and hypereutrophic lakes, based on trophic classification (Carlson, 1996). The algorithm passed the Durbin-Watson test for positive and negative autocorrelation. The selected data set scatter plot displays a strong correlation of $R^2$ equaling 91% (FIG. 9). The withheld data set shows a strong correlation with an $R^2$ of 85% and an RMS error of 0.068, which is about 14% of the withheld data set range (FIG. 10). For the whole data set, containing 45 data points, the $R^2$ is 89%, once again displaying a strong correlation (FIG. 12).

Figure 11:
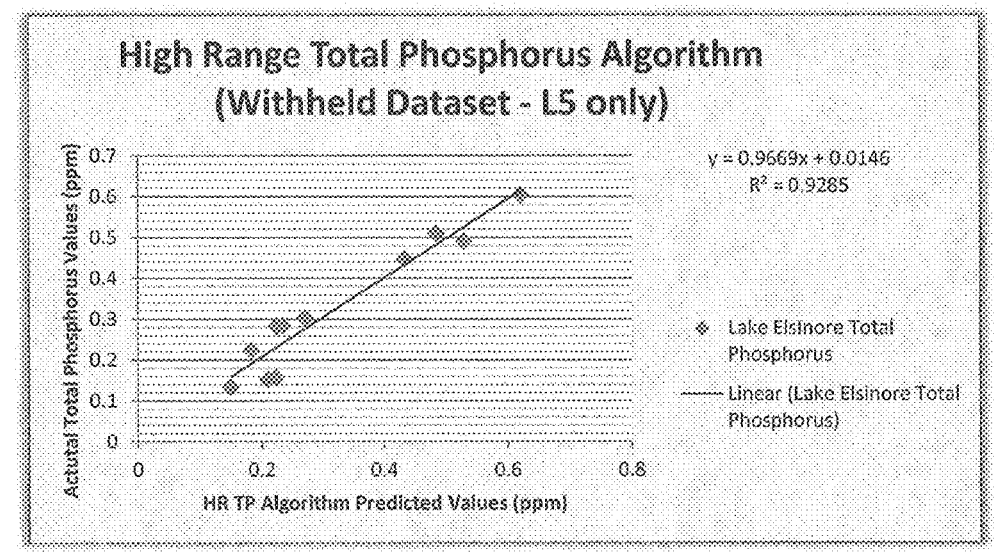
FIG. 11 shows a scatter plot displaying the correlation between the withheld data set in situ measurements of total phosphorus and the 6 ratio high range total phosphorus algorithm predicted values from L5 only. This plot displays a stronger correlation with an $R^2$ of 93% than the withheld data set containing L7 data as well.
Figure 13:
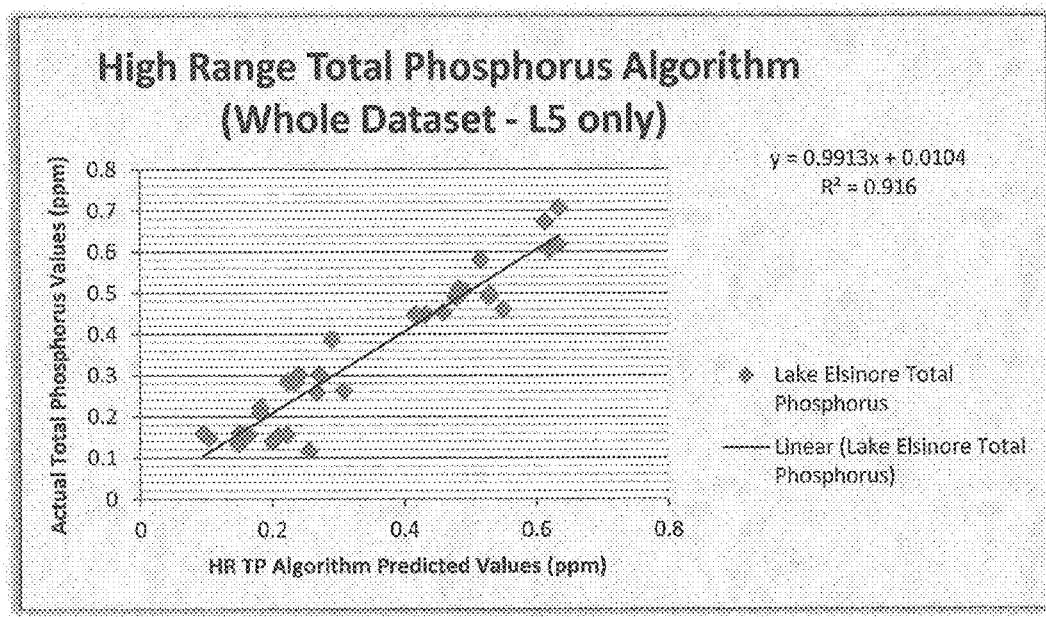
FIG. 13 shows a scatter plot displaying the correlation between the whole data set in situ measurements of total phosphorus and the 6 ratio high range total phosphorus algorithm predicted values for L5 only. This plot displays a stronger correlation with an $R^2$ of 92% than the whole data set containing L7 data as well.

An interesting factor is that LANDSAT 5 had better results than LANDSAT 7. While using only LANDSAT 5 correlations the withheld data set jumped up to 93% for the $R^2$ (8% increase), and the whole data set rose to 92% (3% increase; FIGS. 11 & 13). This could be for varying reasons, such as satellite sensor differentiations, altering the way the sensors measure the reflectance of total phosphorus within the water, or the fact that there are much more L5 data points (23) within the selected data set than L7 (seven).

Figure 14:
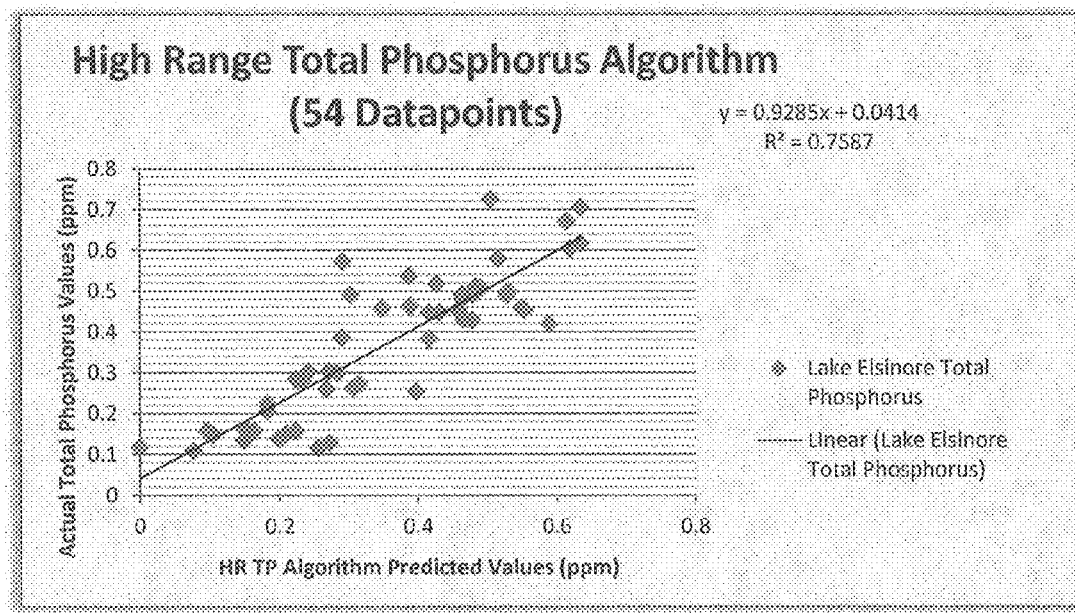
FIG. 14 shows a scatter plot displaying the correlation between a data set of in situ measurements of total phosphorus and the 6 ratio high range total phosphorus algorithm predicted values containing data points that were labeled as problematic. This plot displays a strong correlation with an $R^2$ of 76%. There are 41 L5 and 14 L7 overpass data points within this data set.

The data points displaying bad factors, and as a result were not chosen to be part of the data set from which the algorithm was constructed, were further examined for this specific algorithm, and were examined for correlations. As expected, many of the points displayed poor correlation, due to the various discrepancies affecting their reflectance values. A few points did display a good correlation, and the highest $R^2$ possible is 76%, with the most amounts of data points at 54 (FIG. 14).

$$Total\ Phosphorus=1.14+0.385*Ratio2/1-3.16*Ratio3/2+1.72*Ratio4/2+1.88*Ratio5/2-3.52*Ratio5/3+1.87*Ratio5/4$$

Minitab Statistical Analysis Results $R^2$ adjusted=88.3%

N (number of samples)=30

$d_U$=1.931

$d_L$=0.998 d=1.987 Passed for positive autocorrelation

4−d=2.02 Passed for negative autocorrelation

Data Range=0.1 to 0.703 mg/L

Data Set Correlations
   Selected Data set $R^2$=91%
   Withheld Data set (15 points) $R^2$=85%
   RMS error withheld=0.069
   L5 only (excludes 4 points) $R^2$=93%
   All 45 data points $R^2$=89%
   L5 only (excludes 11 points) $R^2$=92%
   Applied to 54 data points (pulling in 9 "bad" data points) $R^2$=76%

Turbidity

Figure 15:
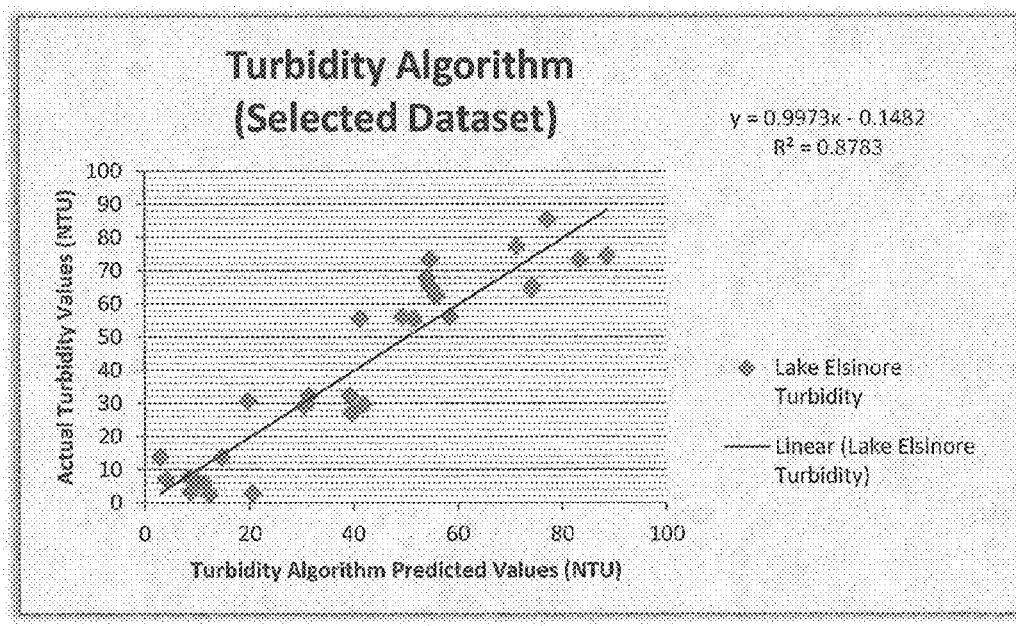
FIG. 15 shows a scatter plot displaying the correlation between the selected data set in situ measurements of turbidity and the 4 ratio turbidity algorithm predicted values. This plot displays a strong correlation with an $R^2$ of 88%. There are 21 L5 and nine L7 overpass data points within this data set.
Figure 16:
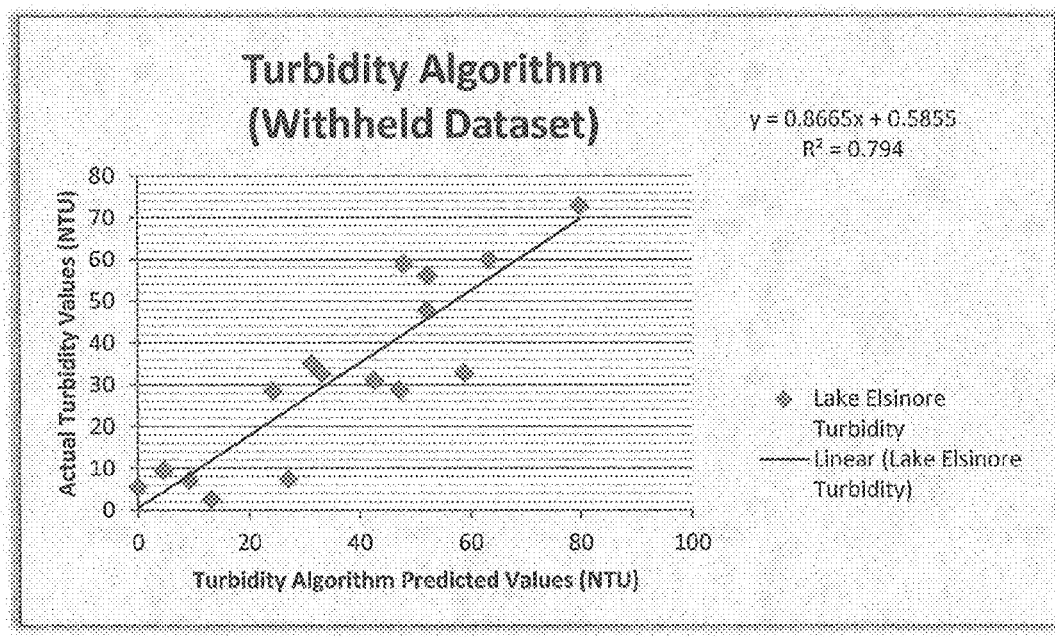
FIG. 16 shows a scatter plot displaying the correlation between the withheld data set in situ measurements of turbidity and the 4 ratio turbidity algorithm predicted values. This plot displays a strong correlation with an $R^2$ of 79%. There are 11 L5 and five L7 overpass data points within this data set.
Figure 18:
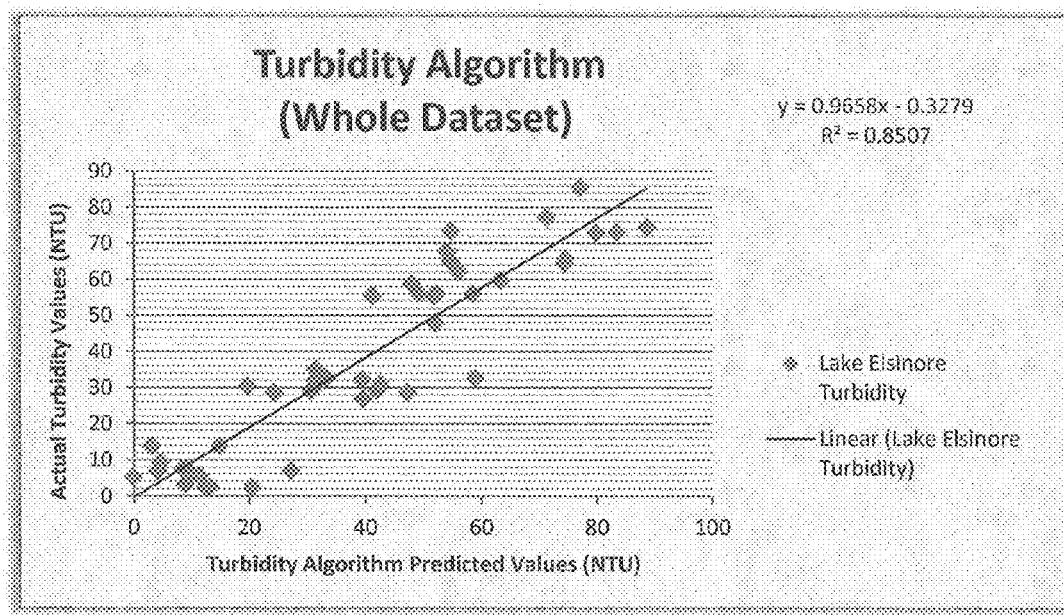
FIG. 18 shows a scatter plot displaying the correlation between the whole data set in situ measurements of turbidity and the 4 ratio turbidity algorithm predicted values. This plot displays a strong correlation with an $R^2$ of 85%. There are 32 L5 and 14 L7 overpass data points within this data set.

An algorithm to measure turbidity was successfully created, and the results are almost as strong as the total phosphorus algorithm. A large range for the algorithm of 2 to 85 NTU was achieved, and will greatly aid in the robustness of the algorithm, allowing it to be applied to a large series of water bodies. The algorithm passed the Durbin-Watson test for positive and negative autocorrelation. The selected data set scatter plot resulted with an $R^2$ of 88% displaying a strong correlation (FIG. 15). The withheld data set displayed an $R^2$ of 79%, as well as an RMS error of 11.04, which is about 16% of the withheld data set range (FIG. 16). For the whole data set, containing 46 points, the $R^2$ is 85% (FIG. 18).

Figure 17:
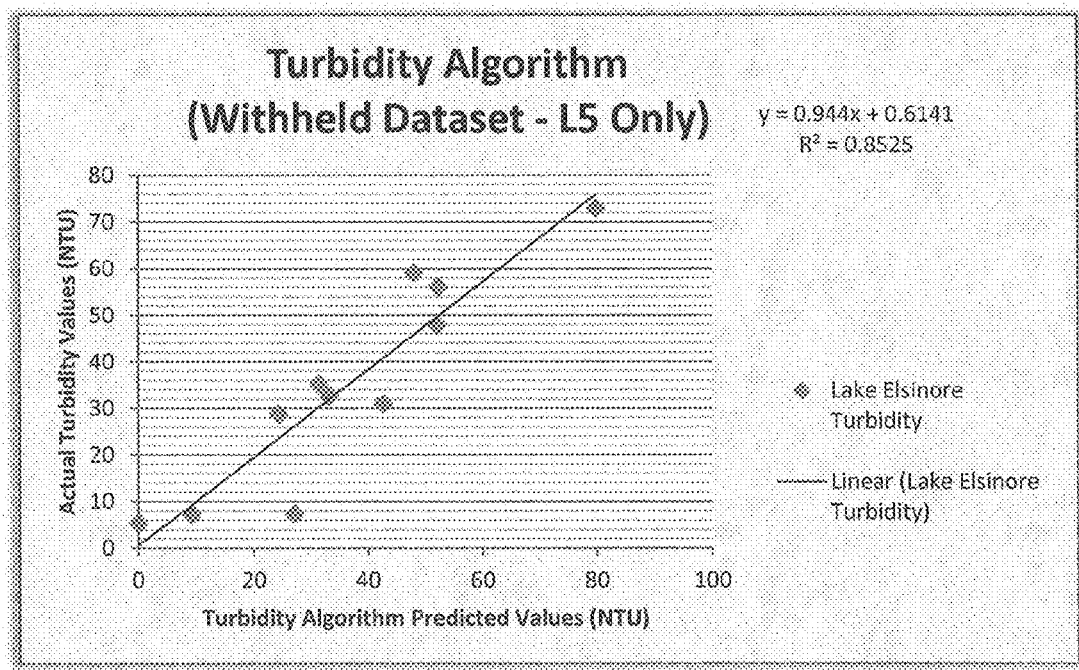
FIG. 17 shows a scatter plot displaying the correlation between the withheld data set in situ measurements of turbidity and the 4 ratio turbidity algorithm predicted values for L5 only. This plot displays a stronger correlation with an $R^2$ of 85% than the withheld data set containing L7 data as well.

Again, L5 displayed better results than L7, much like it did with the total phosphorus data. The withheld data set $R^2$ increased 6%, to 85%, when excluding L7 results, while the whole data set only increased 2% ($R^2$ of 87%; FIG. 17). These results are most likely due to the same reasons listed in the previous discussion section for total phosphorus.

Figure 19:
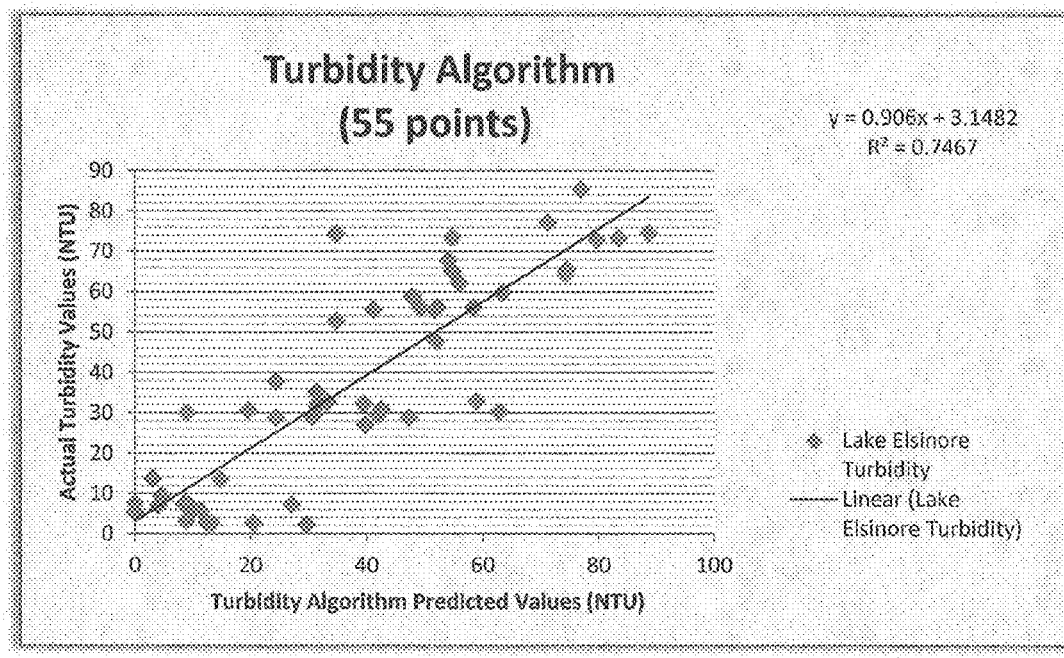
FIG. 19 shows a scatter plot displaying the correlation between a data set of in situ measurements of turbidity and the 4 ratio turbidity algorithm predicted values containing data points that were labeled as problematic. This plot displays a strong correlation with an $R^2$ of 75%. There are 40 L5 and 15 L7 overpass data points within this data set.

The data points displaying bad factors, and as a result were not chosen as part of the data set from which to construct the algorithm, were further examined for this specific algorithm, and were examined for correlations. As expected, many of the points displayed poor correlation, due to the various discrepancies affecting their reflectance values. A few points did display decent correlation, and the highest $R^2$ possible is 75%, with the most amounts of data points at 55 (FIG. 19).

$$\text{Turbidity}=-85.3+47.7*\text{Ratio3}/1-105*\text{Ratio4}/2+157*\text{Ratio4}/3+31.4*\text{Ratio7}/5$$

Minitab Statistical Analysis Results
   $R^2$ adjusted=85.9%
   N (number of samples)=30
   $d_U$=1.739
   $d_L$=1.143
   d=1.97 Passed for positive autocorrelation
   4−d=2.03 Passed for negative autocorrelation
Data Set Correlations
   Selected Data set $R^2$=88%
   Withheld Data set (16 points) $R^2$=79%
   RMS error withheld=11.04
   LANDSAT 5 only (excludes 4 points) $R^2$=85%
   All 46 data points $R^2$=85%
   Data Range=0-85 NTU Total Nitrogen Total nitrogen proved the most difficult parameter for which to obtain a strong algorithm. Efforts were first aimed at creating an algorithm on the entire range of data (0.91 to 8.56), excluding abnormally high measurements (only one of 12.72 ppm), as was successfully completed for total phosphorus. There were no algorithms worth pursuing when trying this range of data, so the ranges were split up into low and high ranges.

Figure 20:
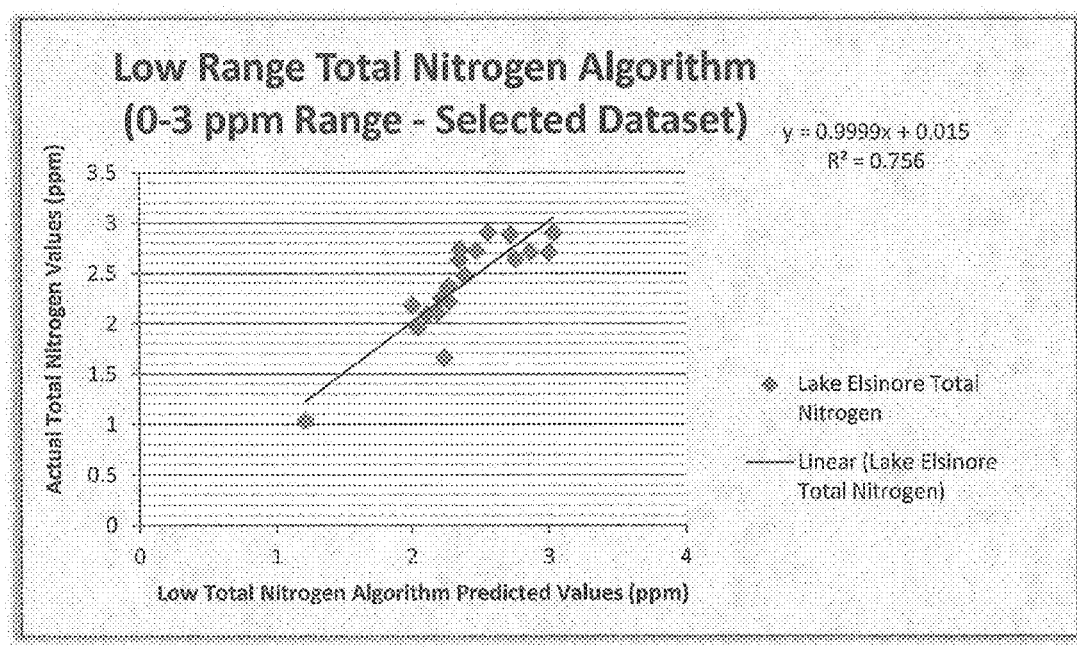
FIG. 20 shows a scatter plot displaying the correlation between the selected data set in situ measurements of low range total nitrogen and the 6 ratio turbidity algorithm predicted values. This plot displays a strong correlation with an $R^2$ of 75%. There are 14 L5 and six L7 overpass data points within this data set.
Figure 21:
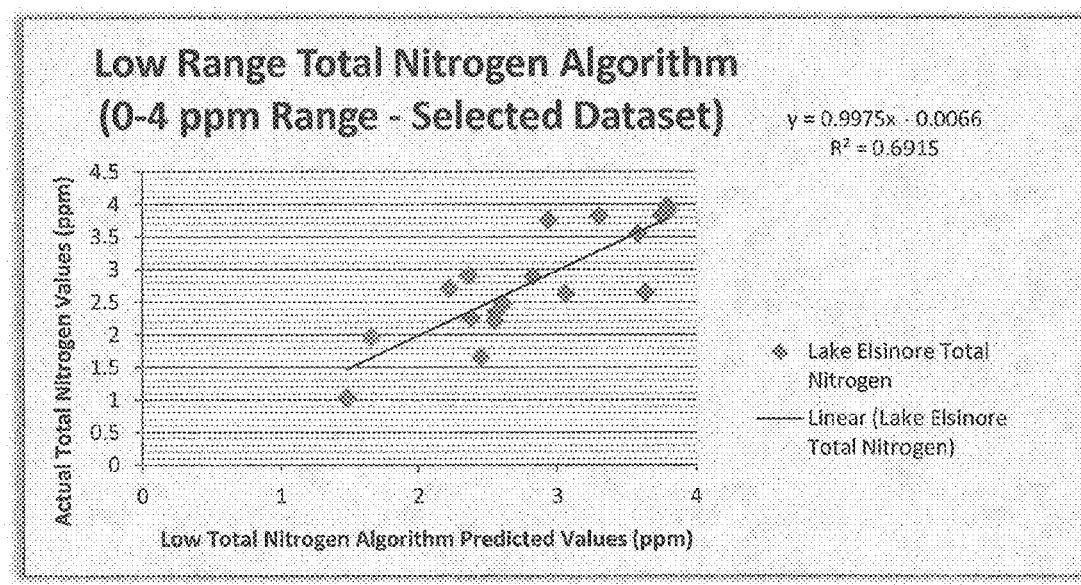
FIG. 21 shows a scatter plot displaying the correlation between the selected data set in situ measurements of low range total nitrogen and the 6 ratio turbidity algorithm predicted values. This plot displays a good correlation with an $R^2$ of 69%. There are 14 L5 and four L7 overpass data points within this data set.
Figure 22:
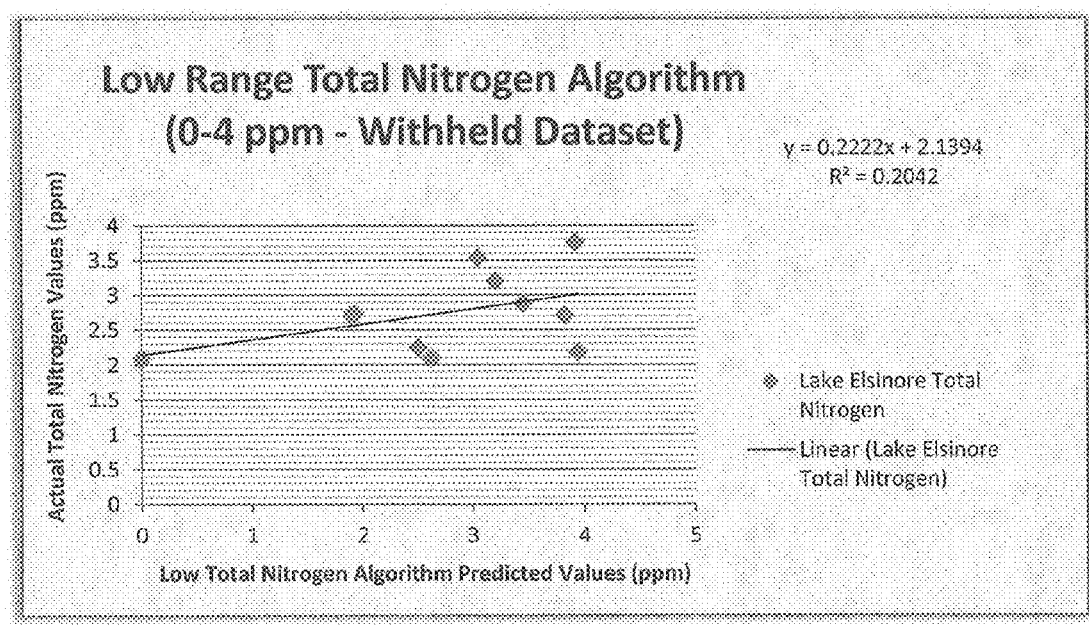
FIG. 22 shows a scatter plot displaying the correlation between the withheld data set in situ measurements of low range total nitrogen and the 6 ratio turbidity algorithm predicted values. This plot displays a weak correlation with an $R^2$ of 20%. There are nine L5 and two L7 overpass data points within this data set.
Figure 23:
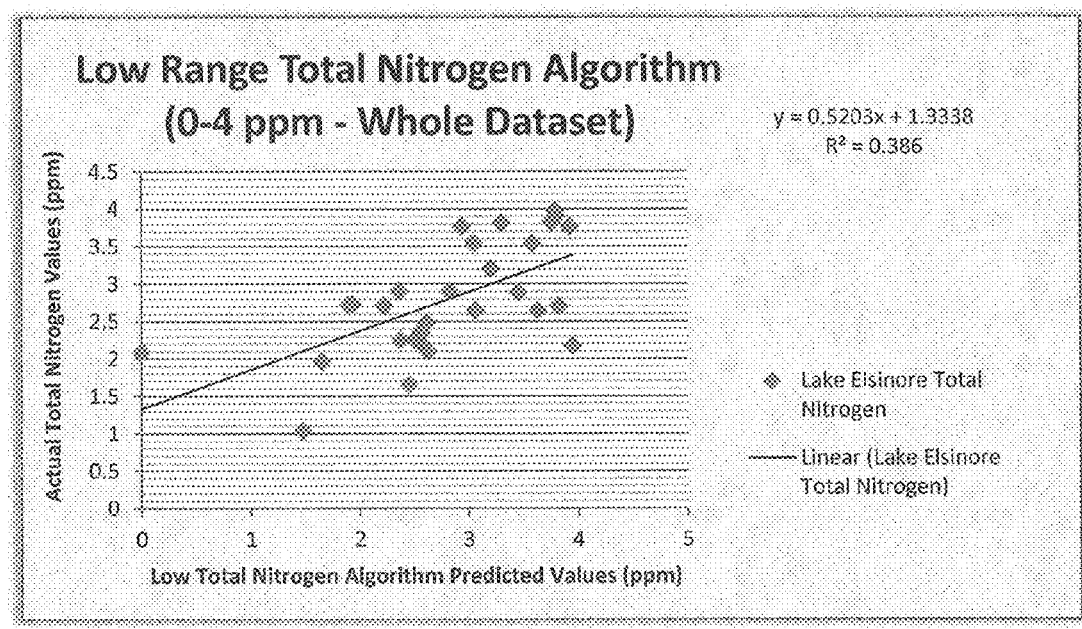
FIG. 23 shows a scatter plot displaying the correlation between the whole data set in situ measurements of low range total nitrogen and the 6 ratio turbidity algorithm predicted values. This plot displays a weak correlation with an $R^2$ of 39%. There are 23 L5 and six L7 overpass data points within this data set.

A low range algorithm created on a data range of about 0-3 ppm resulted with an $R^2$ of 76% on the selected data set, but landed in the indeterminate range of the Durbin Watson test for negative autocorrelation (FIG. 20). A major lack of credibility and validation for this algorithm is the fact there is no withheld data set to test it on, due to the limited amount of data points within this range. A second low range algorithm was created on data containing about 0-4 ppm. This resulted with an $R^2$ of 69% on the selected data set, but performed poorly on the withheld data set ($R^2$ of 20%; FIGS. 21-23). The RMS error also shows an error of 1.01, which is 60% of the withheld data set range. This algorithm fell within the indeterminate range of the Durbin Watson test for both positive and negative autocorrelation.

Figure 24:
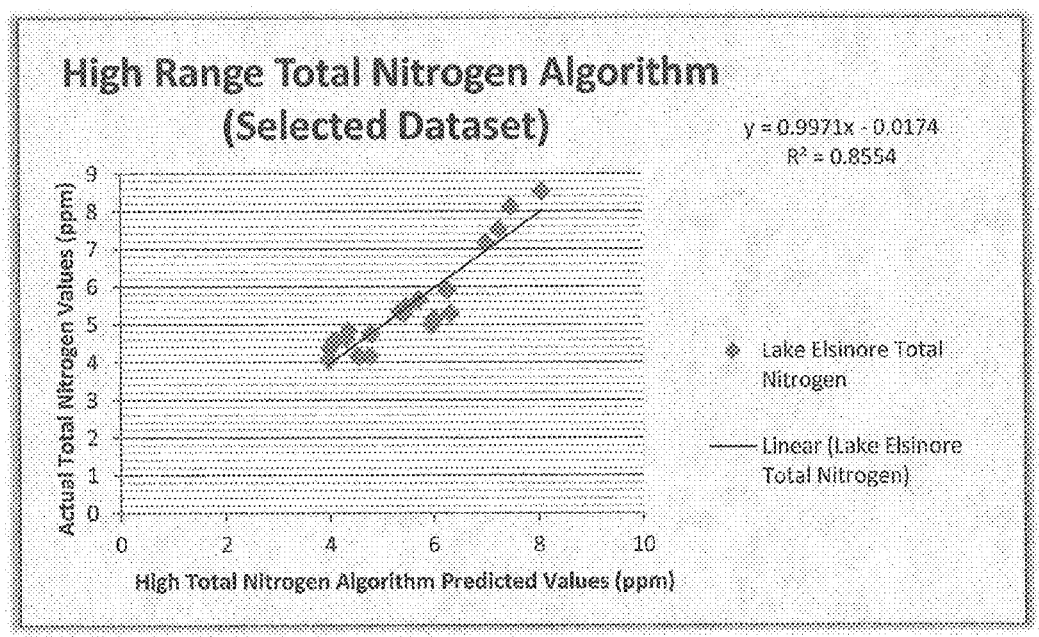
FIG. 24 shows a scatter plot displaying the correlation between the selected data set in situ measurements of high range total nitrogen and the 4 ratio turbidity algorithm predicted values. This plot displays a strong correlation with an $R^2$ of 86%. There are 15 L5 and five L7 overpass data points within this data set.
Figure 25:
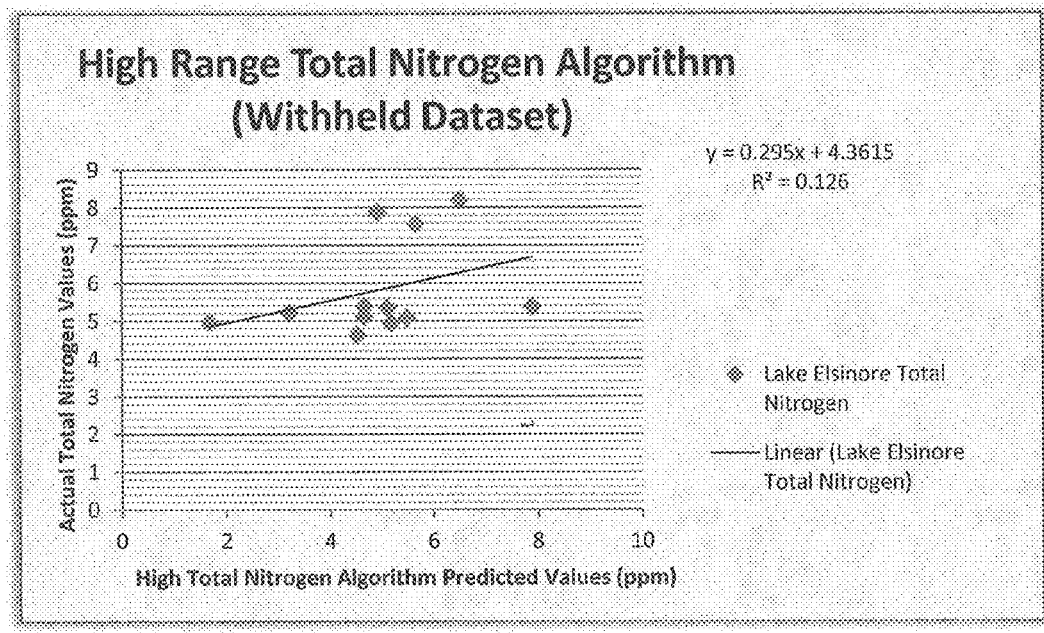
FIG. 25 shows a scatter plot displaying the correlation between the withheld data set in situ measurements of high range total nitrogen and the 4 ratio turbidity algorithm predicted values. This plot displays a very weak correlation with an $R^2$ of 13%. There are seven L5 and five L7 overpass data points within this data set.
Figure 26:
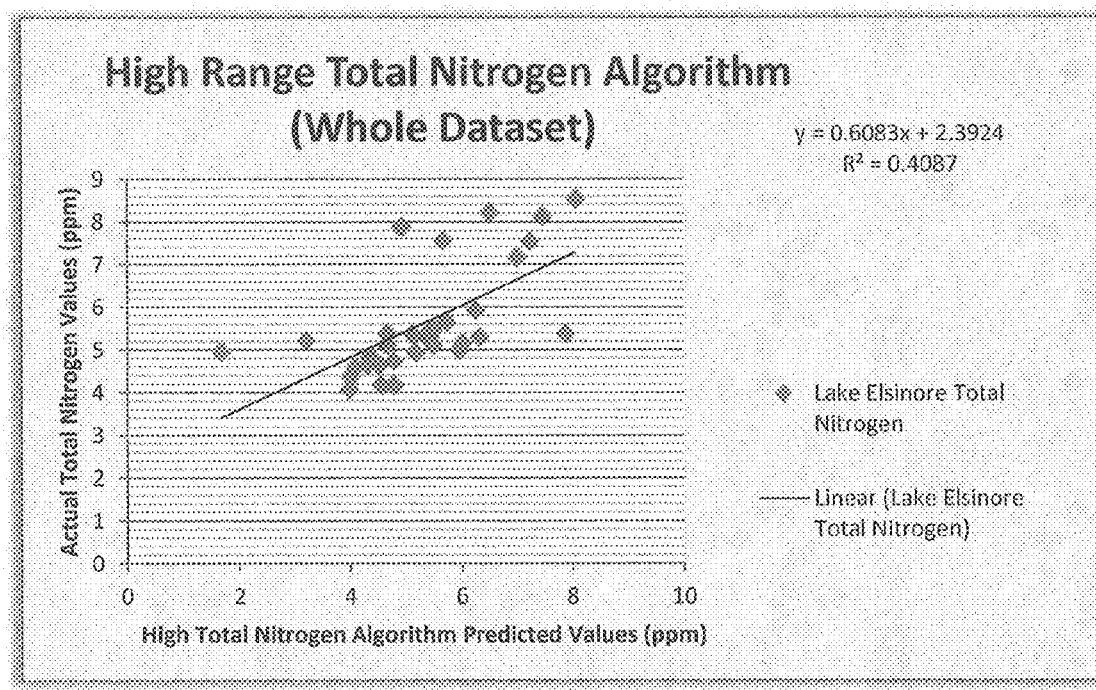
FIG. 26 shows a scatter plot displaying the correlation between the whole data set in situ measurements of high range total nitrogen and the 4 ratio turbidity algorithm predicted values. This plot displays a weak correlation with an $R^2$ of 41%. There are 22 L5 and ten L7 overpass data points within this data set.

Several different high range algorithms were investigated further, that were created on a data range of about 4-9 ppm. The algorithms displaying the best results contained three, four, and six ratios. Out of all three, none exhibited strong results and all performed around the same. The algorithm containing four ratios was slightly better, and resulted in an $R^2$ of 86% on the selected data set (FIG. 24). Both the withheld data set $R^2$ and RMS error were poor, with a 13% and 40% of the withheld data set range (FIGS. 25 & 26). While the algorithm did pass the Durbin Watson test for positive autocorrelation, it also fell within the indeterminate range for negative autocorrelation. Due to these weak results, the goal of creating an accurate and robust algorithm for predicted total nitrogen values via remote sensing is still not finalized.

While various studies have examined measuring total nitrogen values within soil and vegetation from satellites, there are virtually zero studies on the reflectance properties of total nitrogen within water. Therefore, the reasons why total nitrogen failed to render a solid algorithm are only speculation. This parameter may simply not have a distinctive spectral signature or band within the LANDSAT TM spectral range.

$$\text{Low Range Total Nitrogen}=26.0-6.36*\text{Ratio2}/1-19.4*\text{Ratio3}/2+17.9*\text{Ratio4}/2-14.6*\text{Ratio4}/3+6.08*\text{Ratio5}/1-7.98*\text{Ratio5}/3$$

Minitab Statistical Analysis Results
   $R^2$ adjusted=64.4%
   N (number of samples)=20
   $d_U$=2.162
   $d_L$=0.691
Data Set Correlations
   Selected Data set $R^2$=76%
   No Withheld Data set d=2.57 Passed for positive autocorrelation
   4−d=1.43 Indeterminate for negative autocorrelation
   Data Range=0-3 mg/L $$\text{Low Range Total Nitrogen}=11.8-17.0*\text{Ratio4}/1+3.85*\text{Ratio4}/2+10.2*\text{Ratio5}/3-10.1*\text{Ratio5}/4+16.2*\text{Ratio7}/1-10.9*\text{Ratio7}/3$$

Minitab Statistical Analysis Results
   $R^2$ adjusted=52.3%
   N (number of samples)=18
   $d_U$=2.258
   $d_L$=0.603
   d=1.78 Indeterminate for positive autocorrelation
Data Set Correlations
   Selected Data set $R^2$=69%
   Withheld Data set (11 points) $R^2$=20%
      RMS error withheld=1.01
   All 29 data points $R^2$=38%
   4−d=2.22 Indeterminate for negative autocorrelation
   Data Range=0-4 mg/L $$\text{High Range Total Nitrogen}=10.9+11.0*\text{Ratio2}/1-13.8*\text{Ratio3}/1+1.77*\text{Ratio4}/1-8.77*\text{Ratio7}/5$$

Minitab Statistical Analysis Results
    $R^2$ adjusted=81.7%
    N (number of samples)=20
    $d_U$=1.828
    $d_L$=0.894
    d=2.76 Passed for positive autocorrelation
Data Set Correlations
    Selected Data set $R^2$=86%
    Withheld Data set (12 points) $R^2$=13%
        RMS error withheld=1.55
    All 32 data points $R^2$=41%
    4−d=1.24 Indeterminate for negative autocorrelation
    Data Range=4.08-8.557 mg/L
TMDL Parameter Correlation
Dissolved Oxygen As discussed in the methodology chapter, the main target is to find a satellite measureable surrogate for dissolved oxygen. Low dissolved oxygen levels are the fourth impairment listed on the TMDL and is the fourth parameter that requires monitoring. The parameters attempted to correlate with dissolved oxygen were phycocyanin and chlorophyll-α, followed by total phosphorus and turbidity. Several different scenarios were tested.

Figure 27:
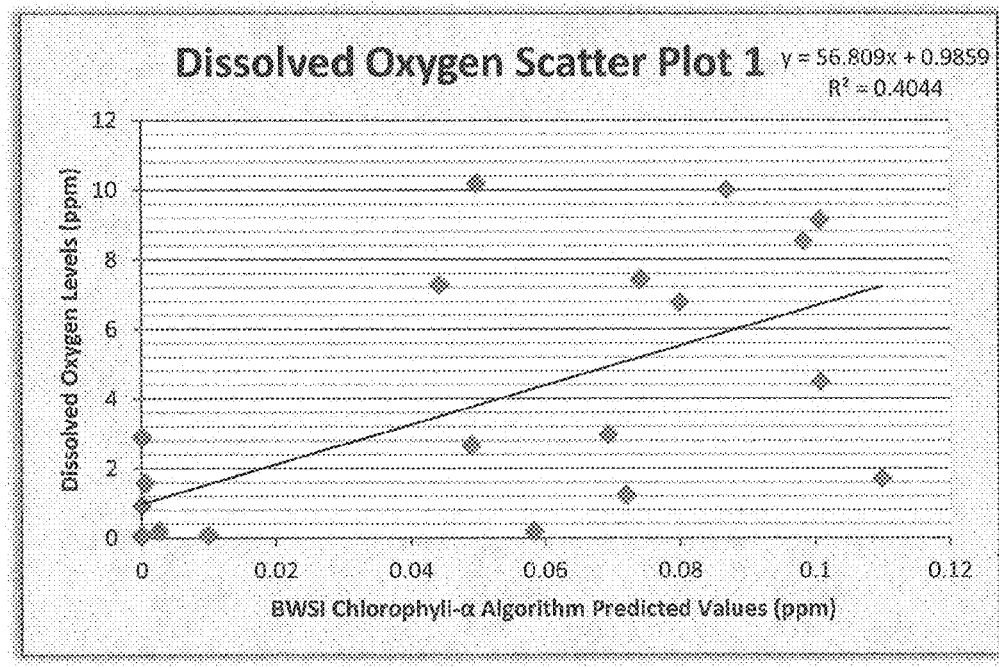
FIG. 27 shows a scatter plot displaying the correlation between BWSI chlorophyll-α algorithm predicted values and the dissolved oxygen measurements collected at the lowest depth, for that same day.
Figure 28:
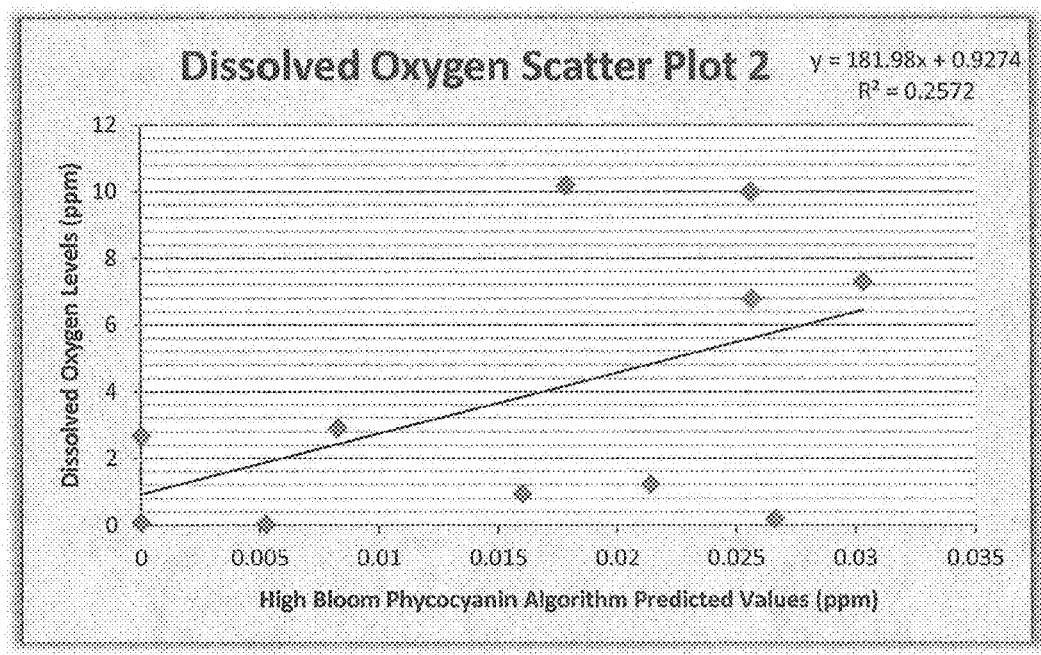
FIG. 28 shows a scatter plot displaying the correlation between high bloom phycocyanin algorithm predicted values and the dissolved oxygen measurements collected at the lowest depth, for that same day.

The first set of scatter plots are taking the dissolved oxygen measurements collected during the same day as the predicted values from the BWSI chlorophyll-α and high bloom phycocyanin algorithm. These scatter plot displays the dissolved oxygen level collected at the lowest depth for that station. The purpose of these scatter plots is to see if when an algal bloom was high (high chlorophyll-α and phycocyanin predicted measurements), if the dissolved oxygen was also high for this day, and vice versa. This would show a positive correlation, meaning that the algal blooms first created super saturated conditions within the water column, and increased the dissolved oxygen. The other result expected may have been a negative correlation, meaning that it does not take long for the algal blooms to die off, decompose, and deplete the dissolved oxygen levels. The scatter plot results for the BWSI chlorophyll-α algorithm displays a positive correlation that is weak, with an $R^2$ of 40% (FIG. 27). A correlation for the high bloom phycocyanin algorithm L7 predicted values is even weaker, with an $R^2$ of 26% (FIG. 28).

Figure 29:
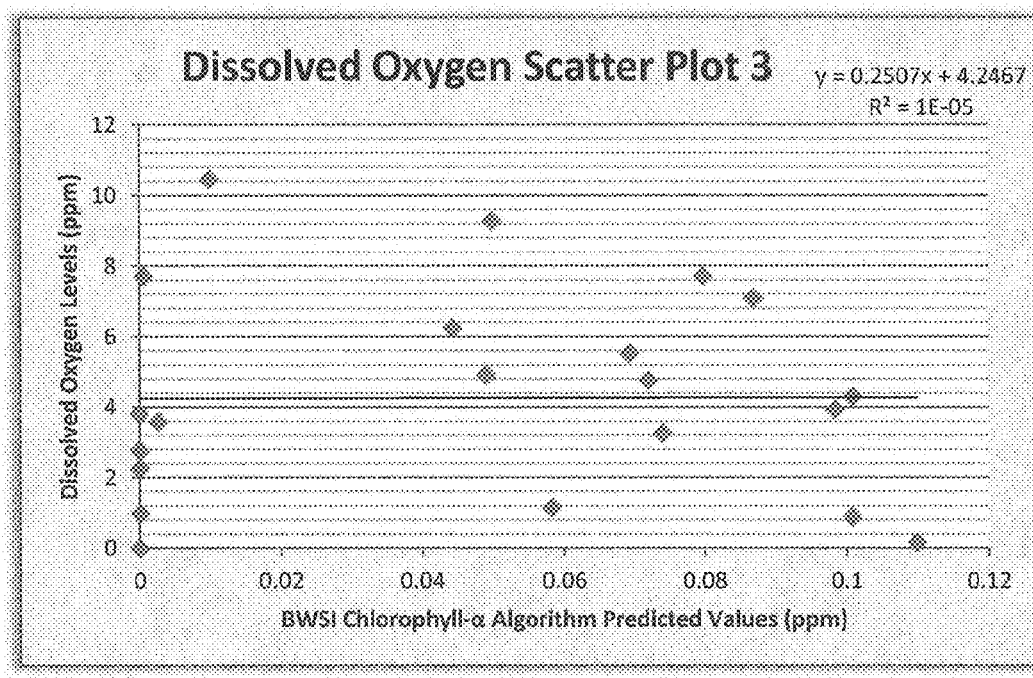
FIG. 29 shows a scatter plot displaying the correlation between BWSI chlorophyll-α algorithm predicted values and the dissolved oxygen measurements collected at the lowest depth, for the next available collection date.
Figure 30:
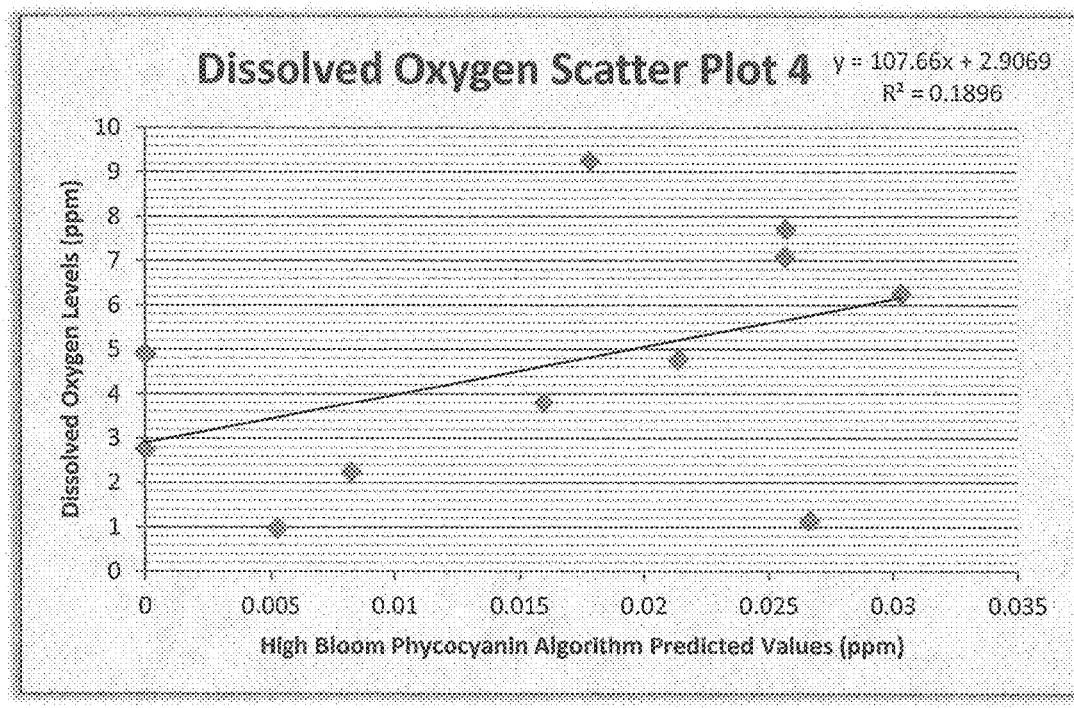
FIG. 30 shows a scatter plot displaying the correlation between the high bloom phycocyanin algorithm predicted values and the dissolved oxygen measurements collected at the lowest depth, for the next available collection date.

The second set of scatter plots take the BWSI chlorophyll-α and high bloom phycocyanin algorithm predicted values from a collection date, and examine correlations with the dissolved oxygen measurements collected at the lowest depth for the next available collection date. The purpose was to prove a correlation between the amount of algal blooms at a previous date and the dissolved oxygen levels within a few weeks; either depleting or raising these levels. The BWSI chlorophyll-α algorithm correlation results are very poor, showing complete variation and zero correlation results (FIG. 29). There is a weak positive correlation with the high bloom phycocyanin L7 predicted values, with an $R^2$ of 19% (FIG. 30).

Figure 31:
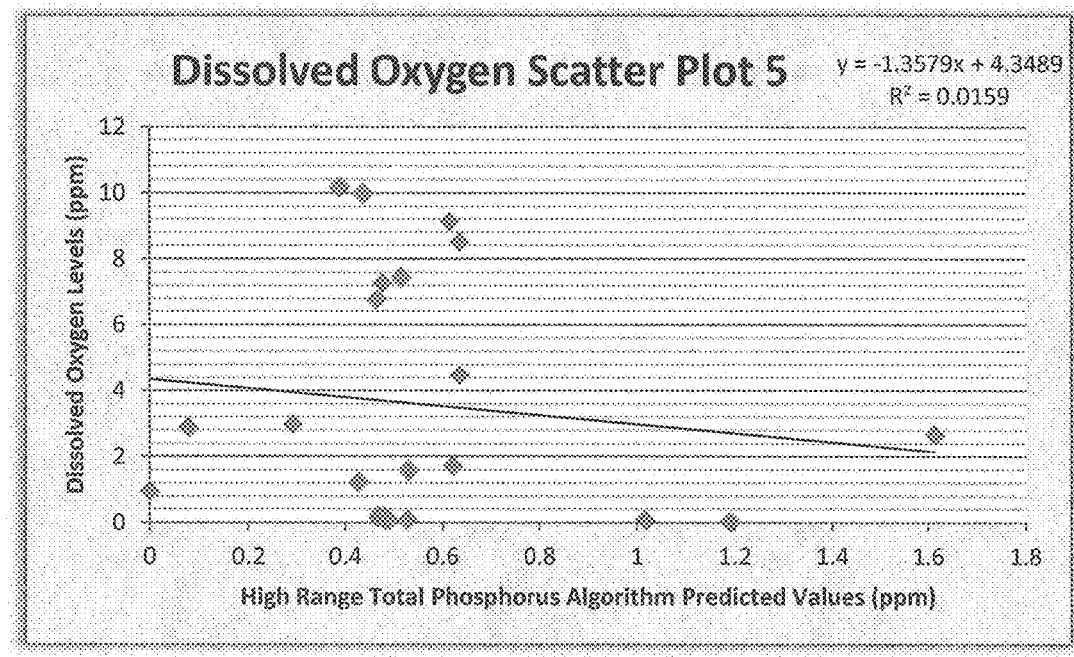
FIG. 31 shows a scatter plot displaying the correlation between the high range total phosphorus algorithm predicted values and the dissolved oxygen measurements collected at the lowest depth, for that same day.
Figure 32:
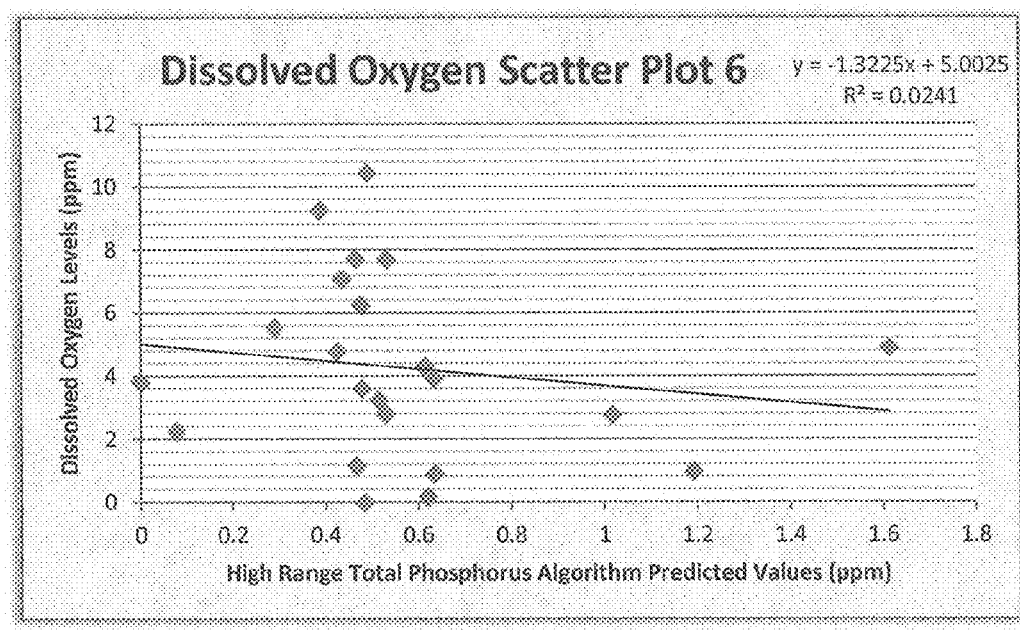
FIG. 32 shows a scatter plot displaying the correlation between the high range total phosphorus algorithm predicted values and the dissolved oxygen measurements collected at the lowest depth, for the next collection date.

The third set of scatter plots take the algorithm predicted values for total phosphorus from a collection date, and examine correlations with the dissolved oxygen measurements collected at the lowest depth for the same and next available collection dates. Again, the idea is to link the algal blooms to the levels of oxygen, because total phosphorus is a nutrient that algal blooms need to flourish. There were no correlations found with either scatter plot, as the $R^2$ results were both very weak (FIGS. 31 & 32).

Figure 33:
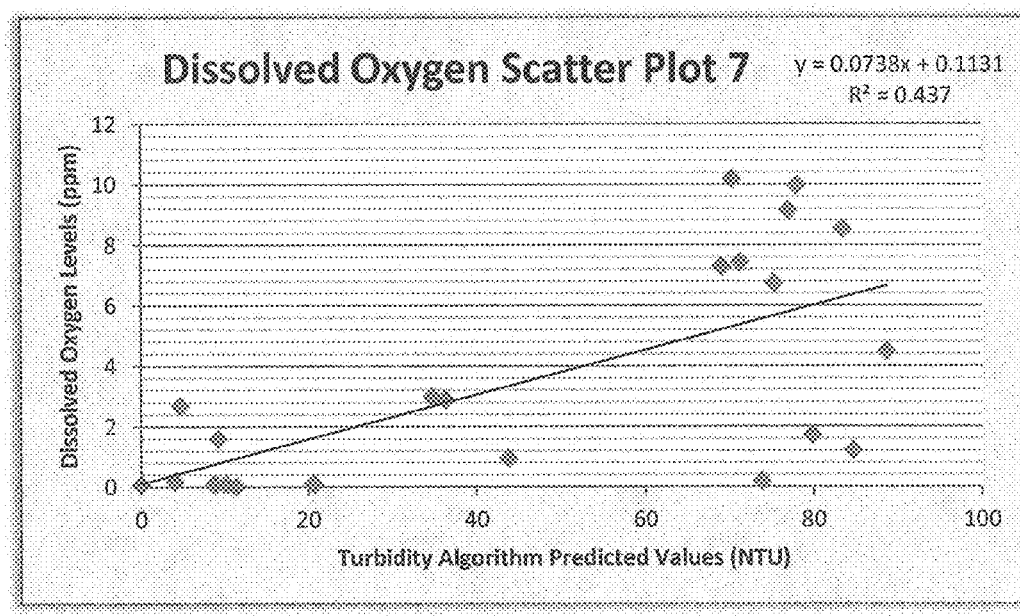
FIG. 33 shows a scatter plot displaying the correlation between the turbidity algorithm predicted values and the dissolved oxygen measurements collected at the lowest depth, for that same day.
Figure 34:
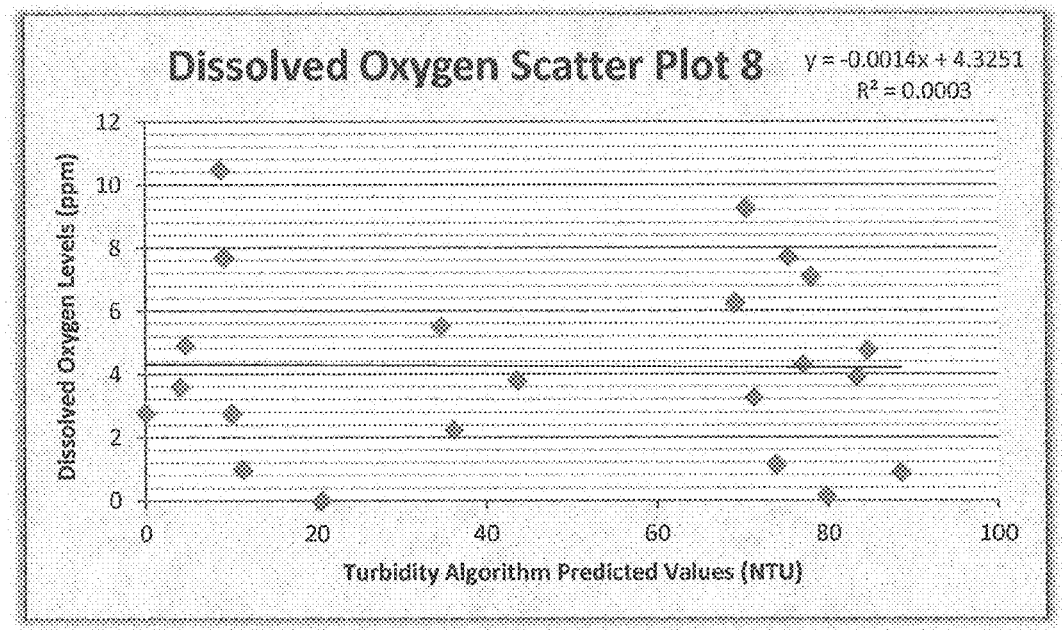
FIG. 34 shows a scatter plot displaying the correlation between the turbidity algorithm predicted values and the dissolved oxygen measurements collected at the lowest depth, for the next collection date.

The fourth set of scatter plots take the algorithm predicted values for turbidity from a collection date, and examine correlations with the dissolved oxygen measurements collected at the lowest depth for the same and next available collection dates. Again, the idea is to link the algal blooms to the levels of oxygen, because algal blooms cause turbidity levels within a water body. There was a positive correlation between the predicted values and dissolved oxygen measurements collected the same day, though it was weak with an $R^2$ of 44% (FIG. 33). The scatter plot for the next collection date data shows no correlation (FIG. 34).

Figure 35:
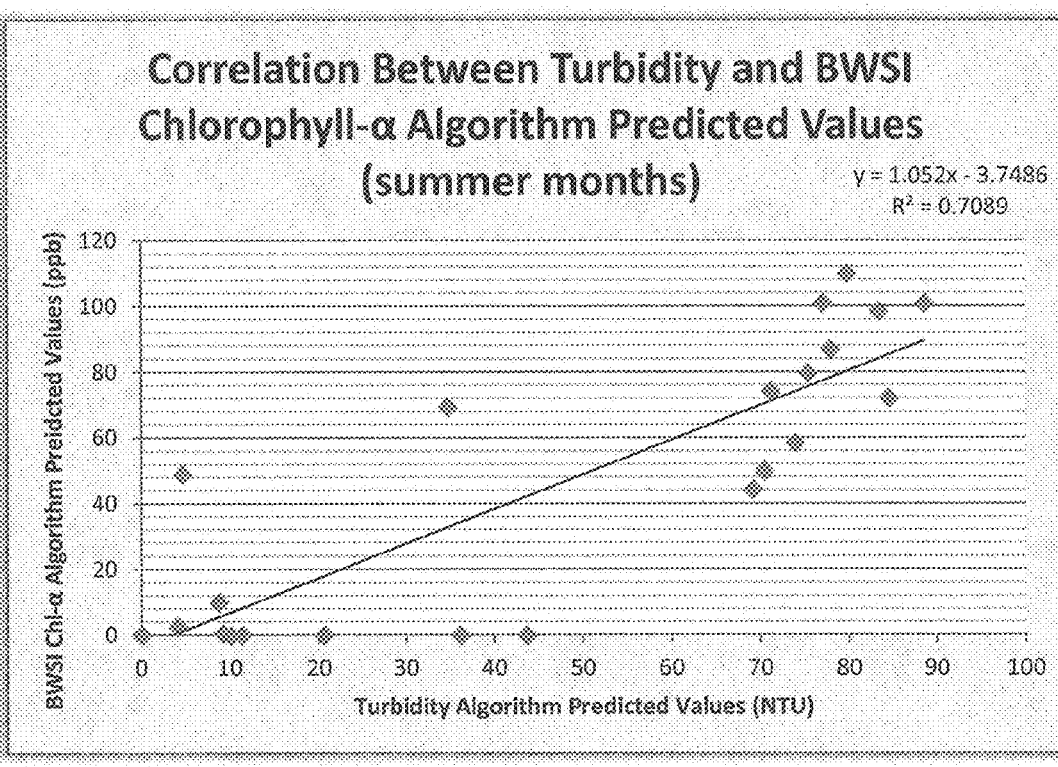
FIG. 35 shows a scatter plot displaying a strong linear relationship between turbidity and BWSI Chlorophyll-α algorithm predicted values for the summer months within Lake Elsinore. The summer months are when algal blooms are the worst, and the turbidity that this algorithm is measuring appears to be these blooms.

Overall, the goal of finding a strong correlation with a parameter that can be measured by satellite was unsuccessful. While it has been proven that algal blooms and stratification are the main cause of dissolved oxygen depletion at lower levels during the summer, a strong correlation was not found. Finding a surrogate for dissolved oxygen in a complex water body that stratifies and mixes irregularly is complicated and involves many factors. A more controlled study would need to be completed to render successful results. These correlations were tried on dates where it was not known if algal blooms were in full bloom, and if they were, if they had just occurred or were starting to die out. Constant and consistent data is missing as well, as some collection date gaps range from two to five weeks. A more predictable water body that has repetitive mixing regimes and seasons would be an easier target for such correlations.
Other Parameters Positive correlations between the other parameters are displayed in scatter plots below. The highest relationships between any parameters are between turbidity and the parameters representing algal blooms. In the previous section the correlations between chlorophyll-α and turbidity with dissolved oxygen look very similar. When these two parameters (chlorophyll-α and turbidity) are directly correlating, they display a positive correlation with an $R^2$ of 71% (FIG. 35). These summer algal blooms are the main cause of turbidity during the summer months, and these results display that the turbidity algorithm is mainly measuring this type of turbidity within the lake during these months. While correlating these two parameters including months other than summer, there is not a strong correlation.

Figure 36:
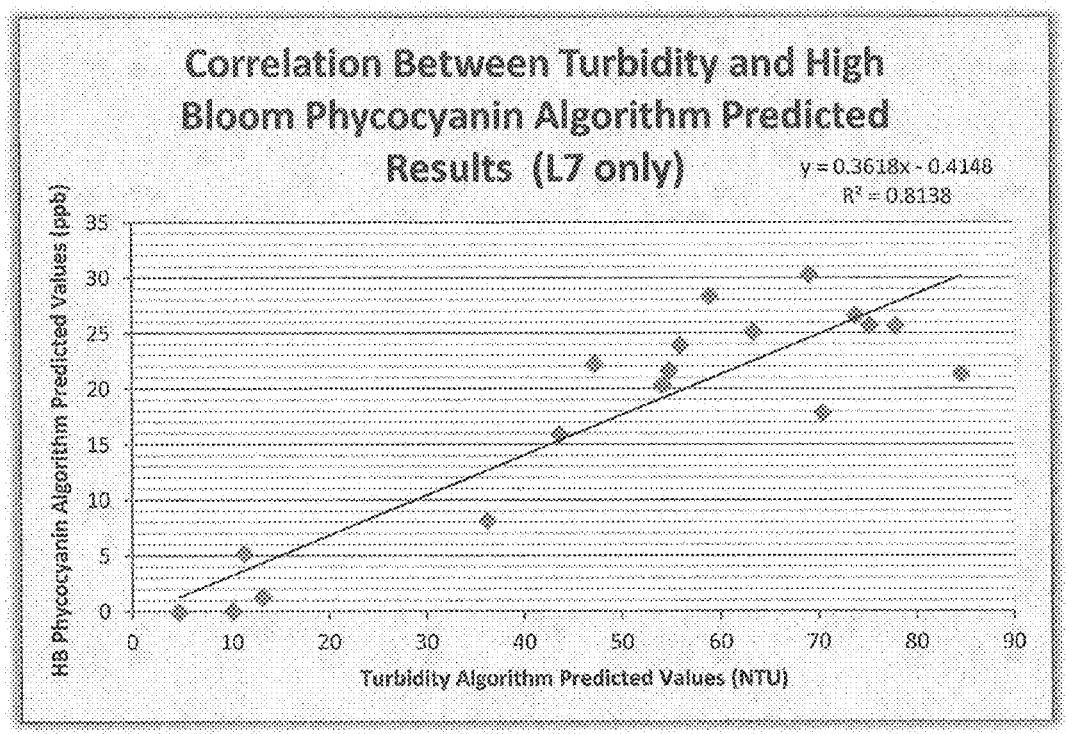
FIG. 36 shows a scatter plot displaying a strong linear relationship between turbidity and HB phycocyanin algorithm predicted values for L7 only for all months within Lake Elsinore. Cyanobacteria blooms have been recorded as present within the lake for most of the year, and the turbidity algorithm appears to be measuring these blooms.

Algal blooms containing cyanobacteria have been recorded as being present within the lake throughout most of the year. A correlation between the high bloom phycocyanin predicted values for L5 and 7 and the Loew turbidity algorithm predicted values reveal a very weak correlation. But when this correlation is restricted to L7 values only, the correlation is strong with an $R^2$ of 81% (FIG. 36). As stated earlier, the fact the L7 predicted values from the high bloom algorithm follow the rest of the results within this study, and show a strong correlation with turbidity as expected, lends more evidence that the L5 satellite corrections may not be robust.

Figure 37:
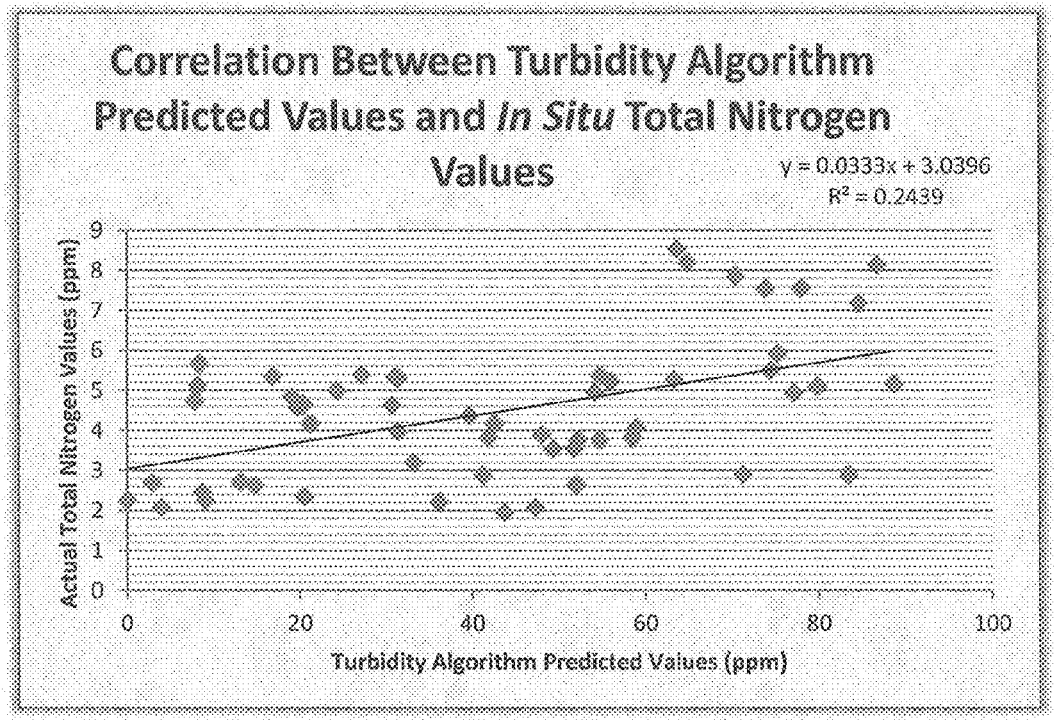
FIG. 37 shows a scatter plot between turbidity predicted total nitrogen values and in situ total nitrogen values, displaying a weak positive linear relationship.

A strong algorithm could not be created for total nitrogen and it was hoped a satellite measureable parameter may reveal a strong correlation with the in situ total nitrogen values. The turbidity algorithm predicted values revealed a weak positive correlation with the total nitrogen actual values, displaying an $R^2$ of 24% (FIG. 37).

Figure 38:
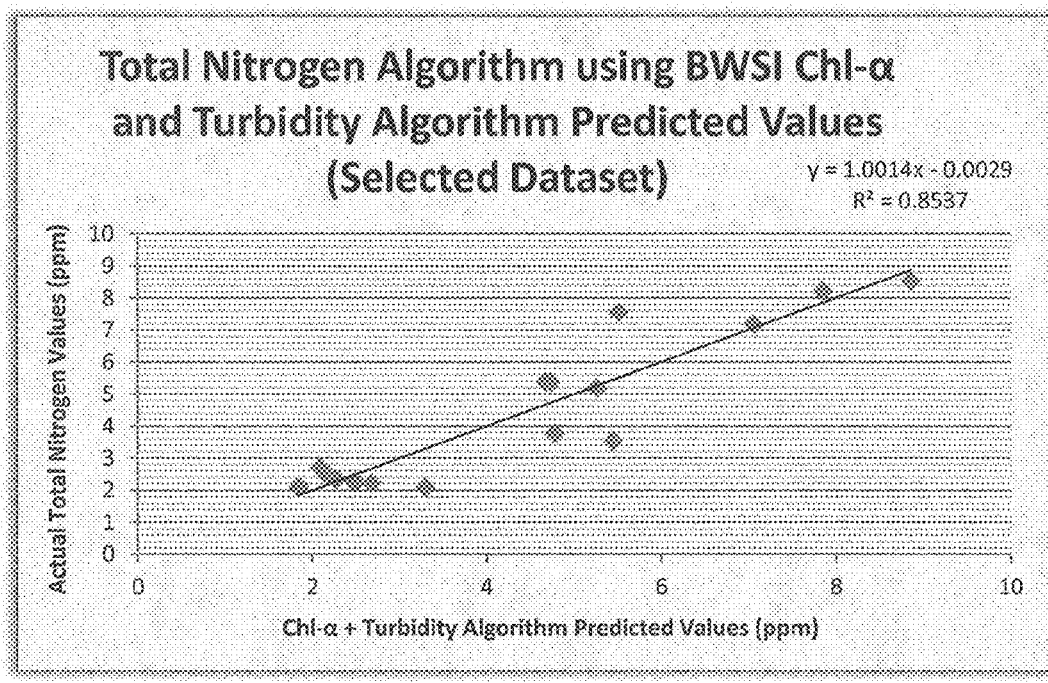
FIG. 38 shows a scatter plot displaying the correlation between a multiple regression algorithm containing the predicted values from the Loew turbidity algorithm and BWSI Chlorophyll-α algorithm, and the actual total nitrogen values for the selected data set. The $R^2$ shows a strong linear relationship of 85%. There are 10 L5 and six L7 overpass data points within this data set.
Figure 39:
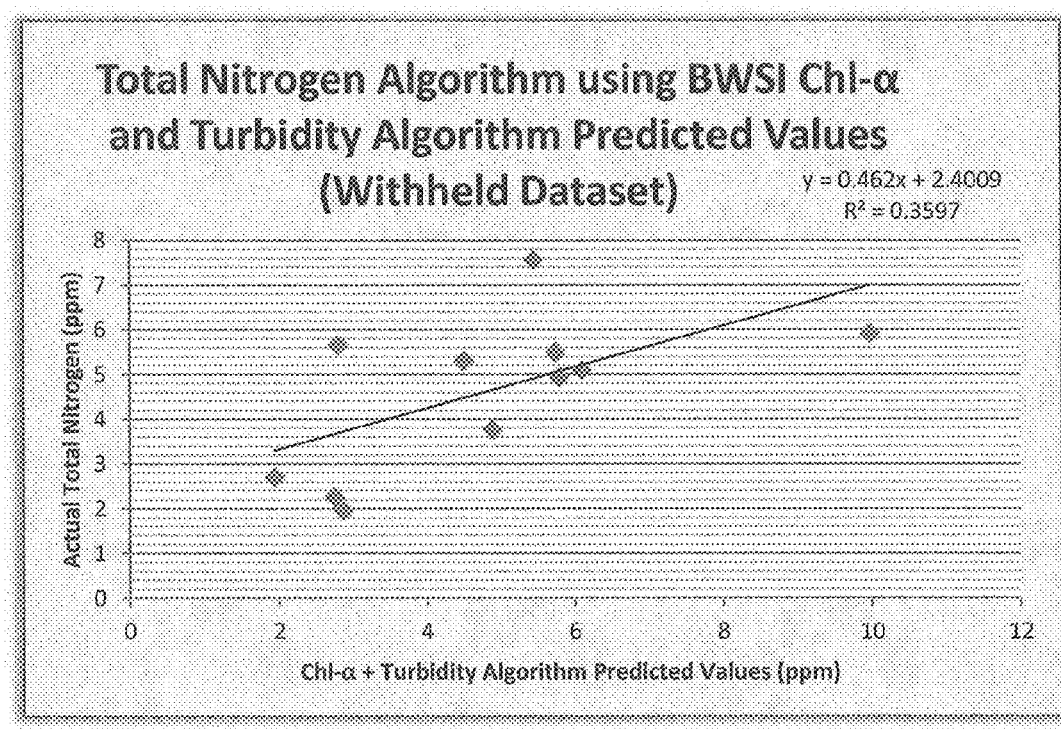
FIG. 39 shows a scatter plot displaying the correlation between a multiple regression algorithm containing the predicted values from the Loew turbidity algorithm and BWSI Chlorophyll-α algorithm, and the actual total nitrogen values for the withheld data set. The $R^2$ shows a weak linear relationship of 36%. There are six L5 and five L7 overpass data points within this data set.

A multiple regression using several different parameters as independent variables revealed an algorithm using the predicted values from the BWSI chlorophyll-α and turbidity algorithm. When this algorithm was applied to the data, the selected data resulted in a strong correlation with an $R^2$ of 85% (FIG. 38). The withheld data set showed a weak correlation, with an $R^2$ of 36%, though these results are still the best found within this study for measuring total nitrogen from satellites (FIG. 39). The range of data for this algorithm was also not split up, and ranges from 2.0 to 8.5 ppm. This algorithm did fail the Durbin Watson test for positive autocorrelation, though it was close and only by 0.01. The two independent variables, chlorophyll-α and turbidity, are obviously correlated with each other as demonstrated previously. The predicted values from the high range total phosphorus algorithm were tried with various multiple regressions, including the turbidity and chlorophyll-α algorithms, but the algorithms created were never stronger than the one below.

Figure 40:
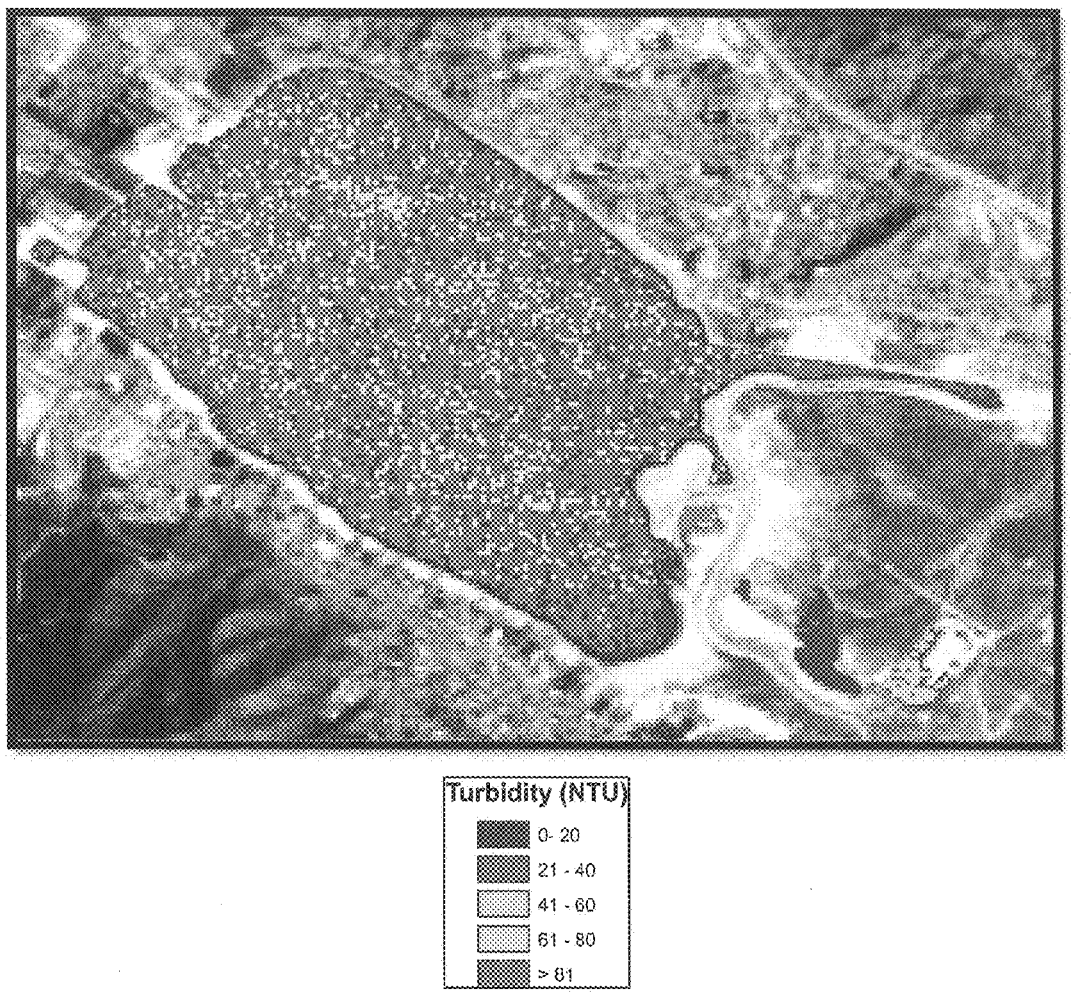
FIG. 40 shows an image created to highlight the amount of turbidity within Lake Elsinore for Aug. 28, 2002. The color scale shows the amount of turbidity increasing from cool colors to warm, or blue to red. The arrow is identifying the small channel designated a fishing area, that does not mix with the rest of the lake when the levels are low.

Total Nitrogen=1.74+0.0199*BWSI Chlorophyll-α Algorithm+0.0260*Turbidity Algorithm Minitab Statistical Analysis Results
  $R^2$ adjusted=83.1%
  N (number of samples)=16
  $d_U$=1.539
  $d_L$=0.982
Data Set Correlations
  Selected Data set $R^2$=85%
  Withheld Data set (11 points) $R^2$=35%
  RMS error withheld=1.77
  d=1.53 Failed for positive autocorrelation (very close)
  4−d=2.47 Passed for negative autocorrelation
  Data Range=2.0-8.5 mg/L
Image Processing The image processing results aid in viewing the levels of each parameter throughout the entire surface area of the Lake Elsinore, and help assess the overall health of the lake throughout time (Appendix A). Color scaled legends that exhibit different categories of levels for the parameter are created to easily view the quality water body (FIG. 40). These legends can also be manipulated to display which regions of the lake are meeting the TMDL requirements. A few of these images show Lake Elsinore in complete exceedance, while other images show a healthier lake (FIG. 41). In summary, the lake generally appears to have gotten healthy as the years progressed, with a few exceptional dates.

Figure 42:
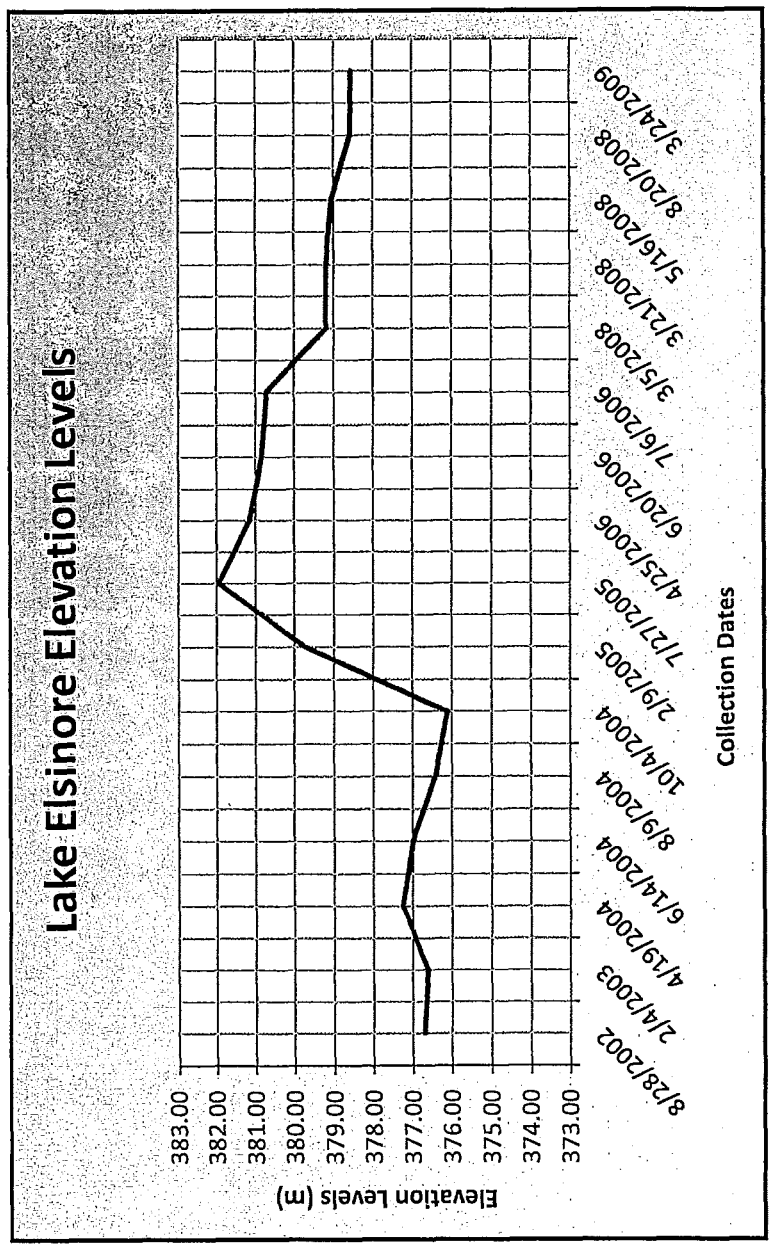
FIG. 42 shows a trend line showing the change in Lake Elsinore water levels for the time span the thesis study covered. The levels dropped dangerously low during 2004, and substantially increased in 2005 due to record rain fall. The water levels have been kept at an optimum level since, with recycled water inputs.
Figure 43:
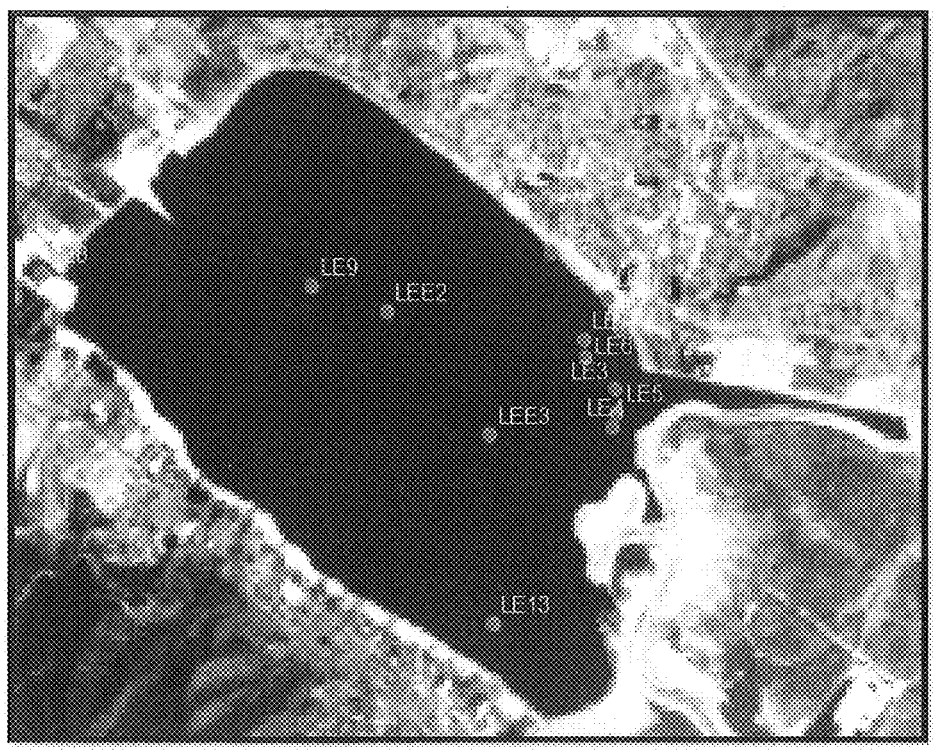
FIG. 43 in Appendix A shows a natural color image of Lake Elsinore with stations for reference.
Figure 44:
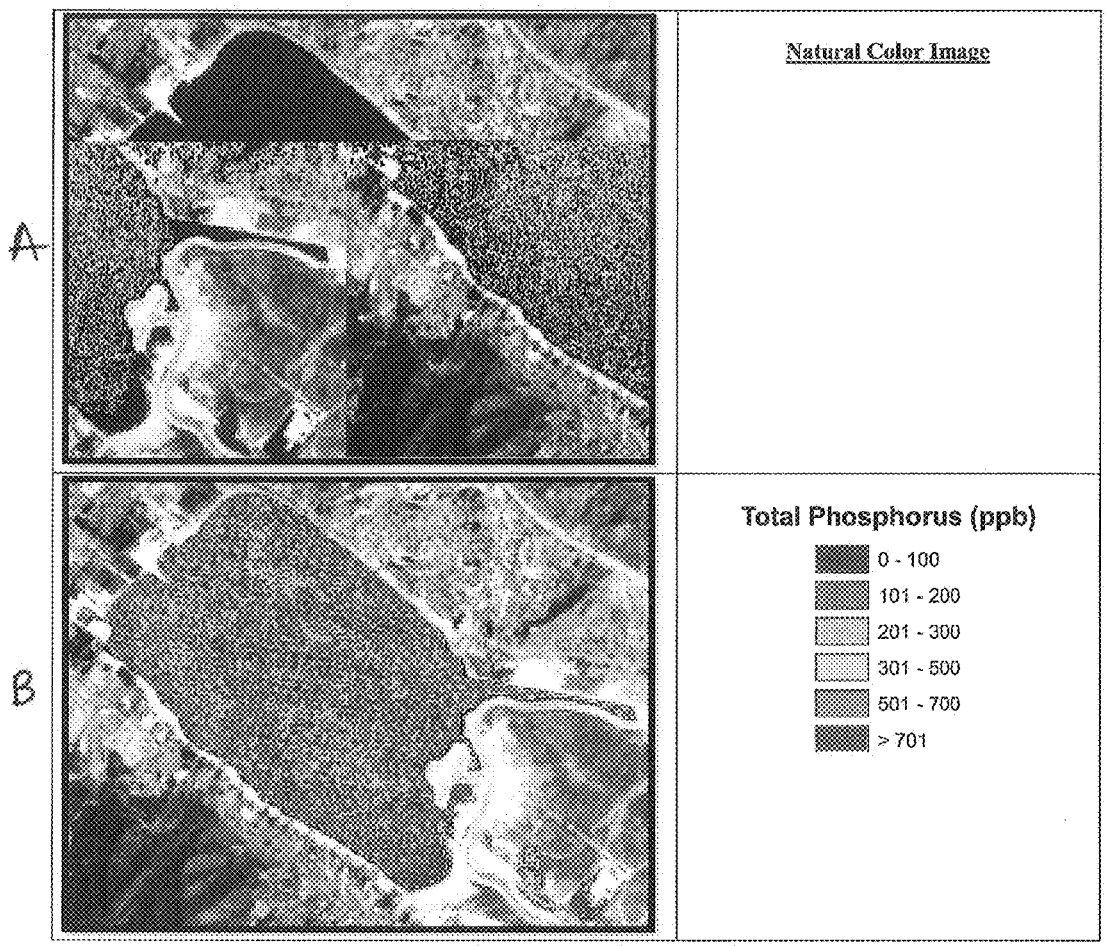
FIG. 44 in Appendix A shows data from a satellite passover on Aug. 28, 2002. Panel A is a natural color image. Panel B is the total phosphorus. Panel C is turbidity. Panel D is the TMDL exceedance for total phosphorus.
Figure 44:
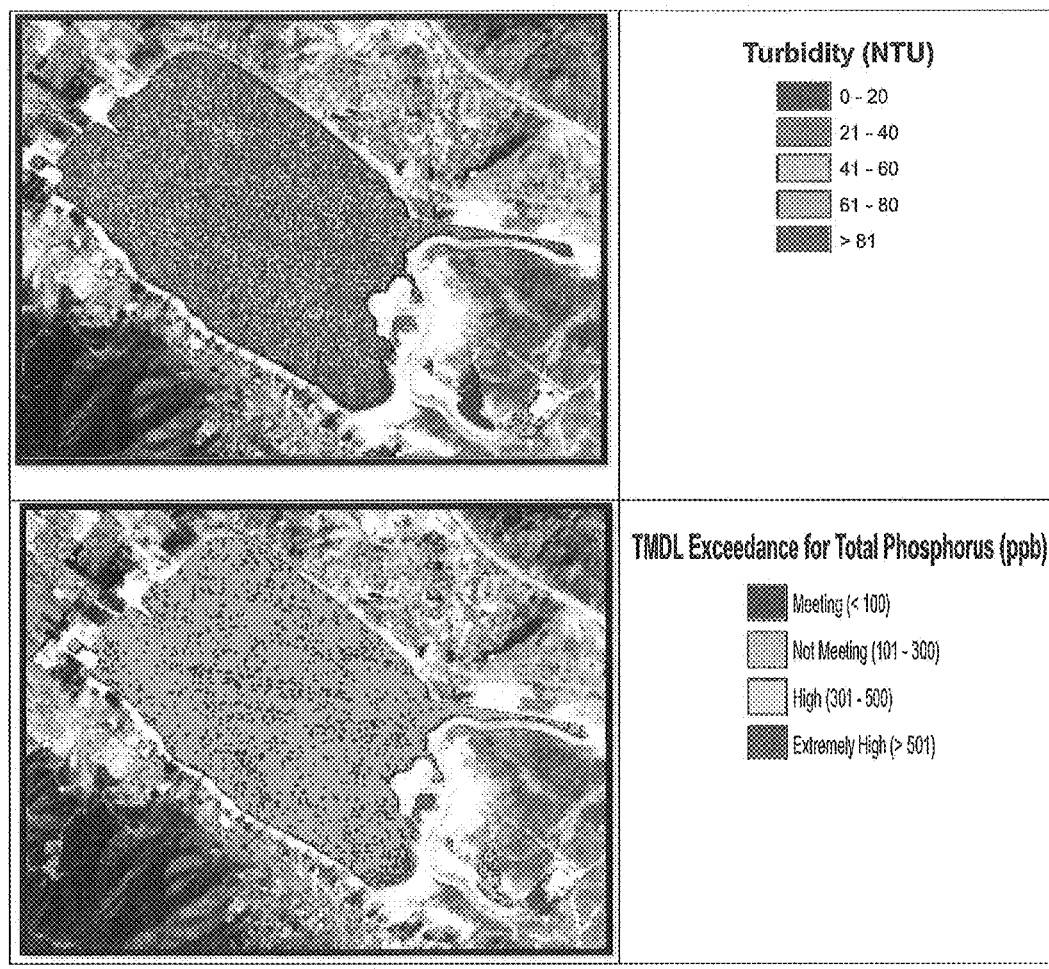
Figure 45:
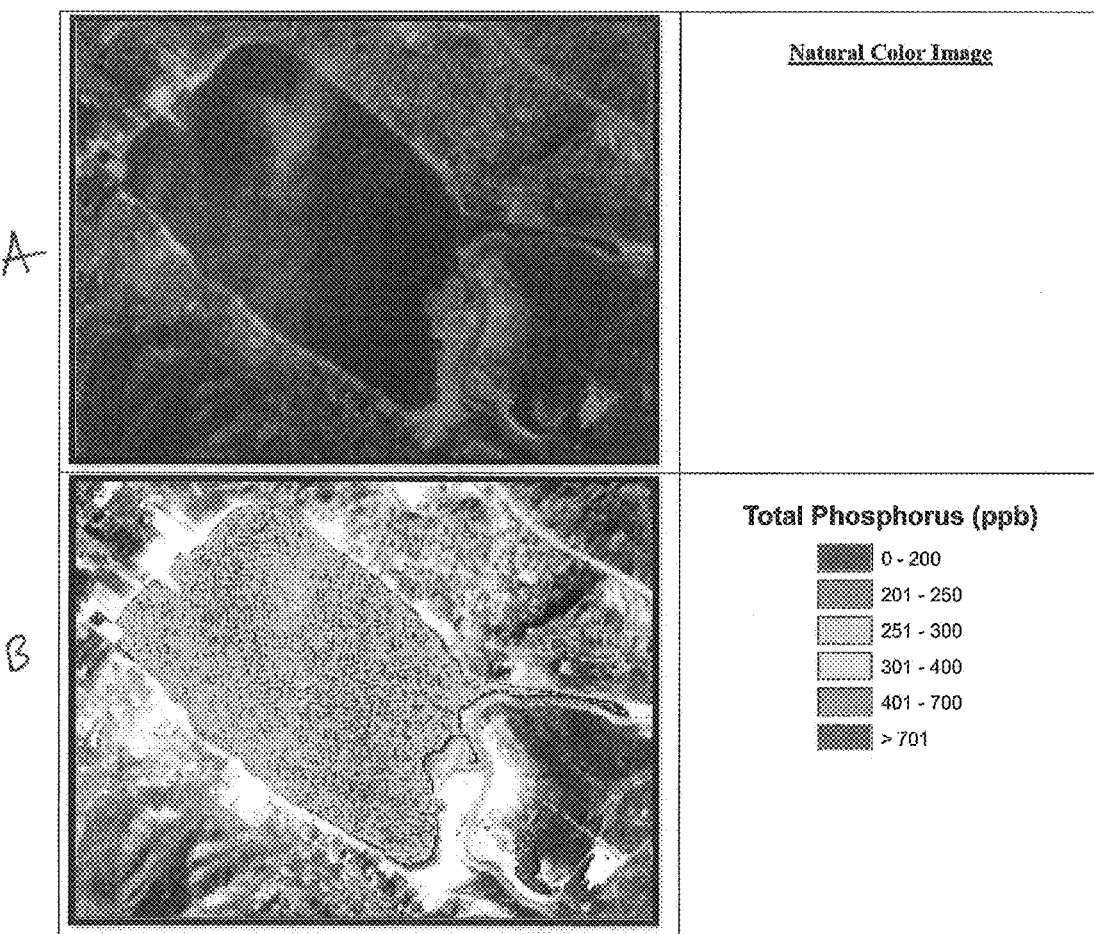
FIG. 45 in Appendix A shows data from a satellite passover on Feb. 3, 2003. Panel A is a natural color image. Panel B is the total phosphorus. Panel C is turbidity.
Figure 45:
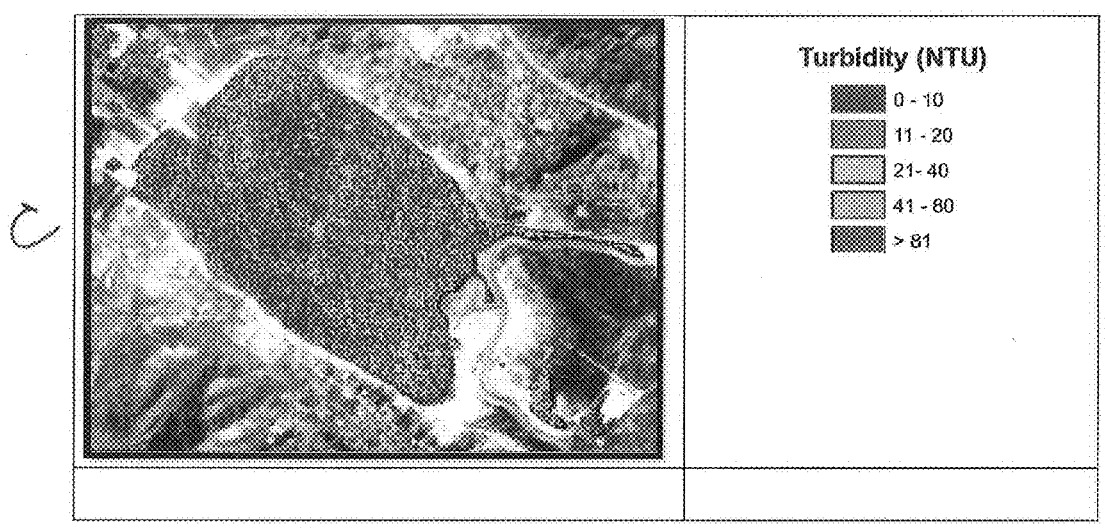
Figure 46:
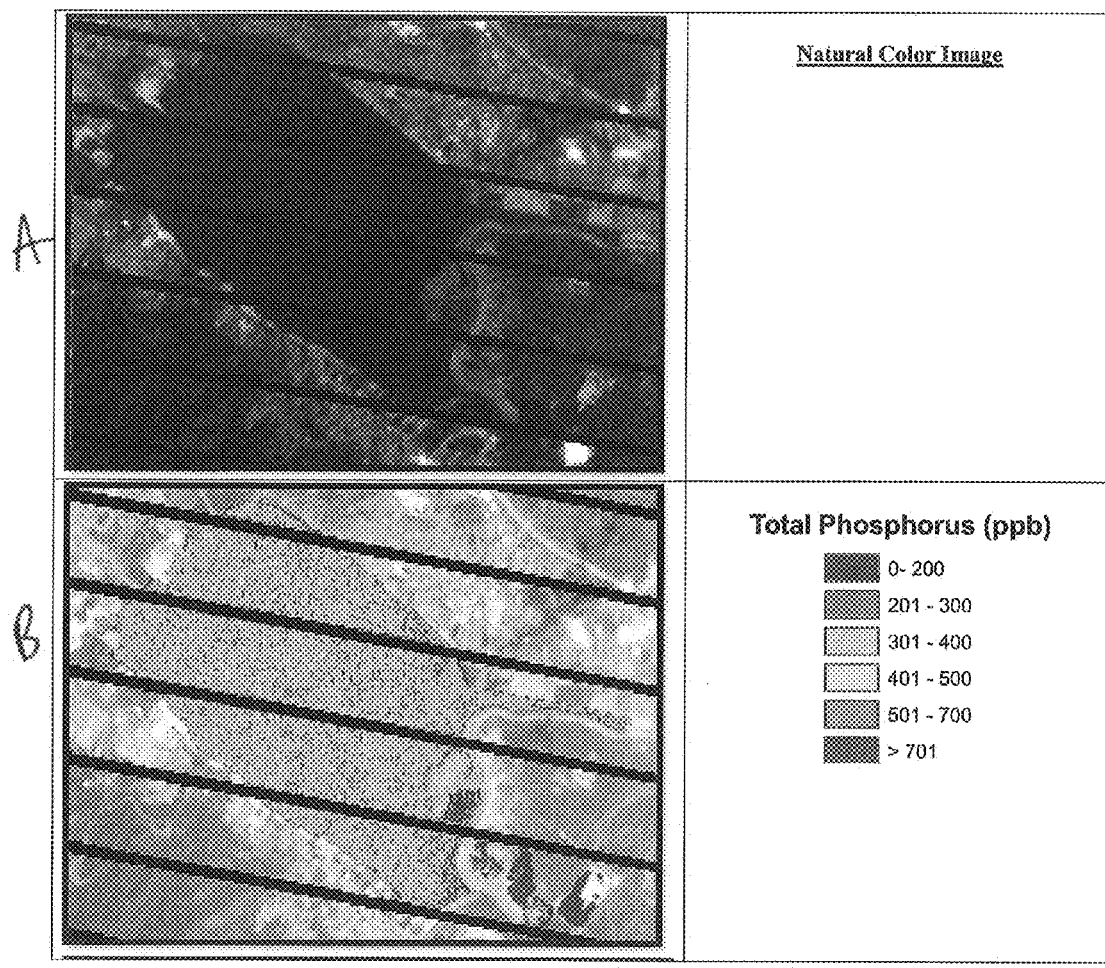
FIG. 46 in Appendix A shows data from a satellite passover on Apr. 19, 2004. Panel A is a natural color image. Panel B is the total phosphorus. Panel C is turbidity. Panel D is chlorophyll-α. Panel E is Phycocyanin.
Figure 46:
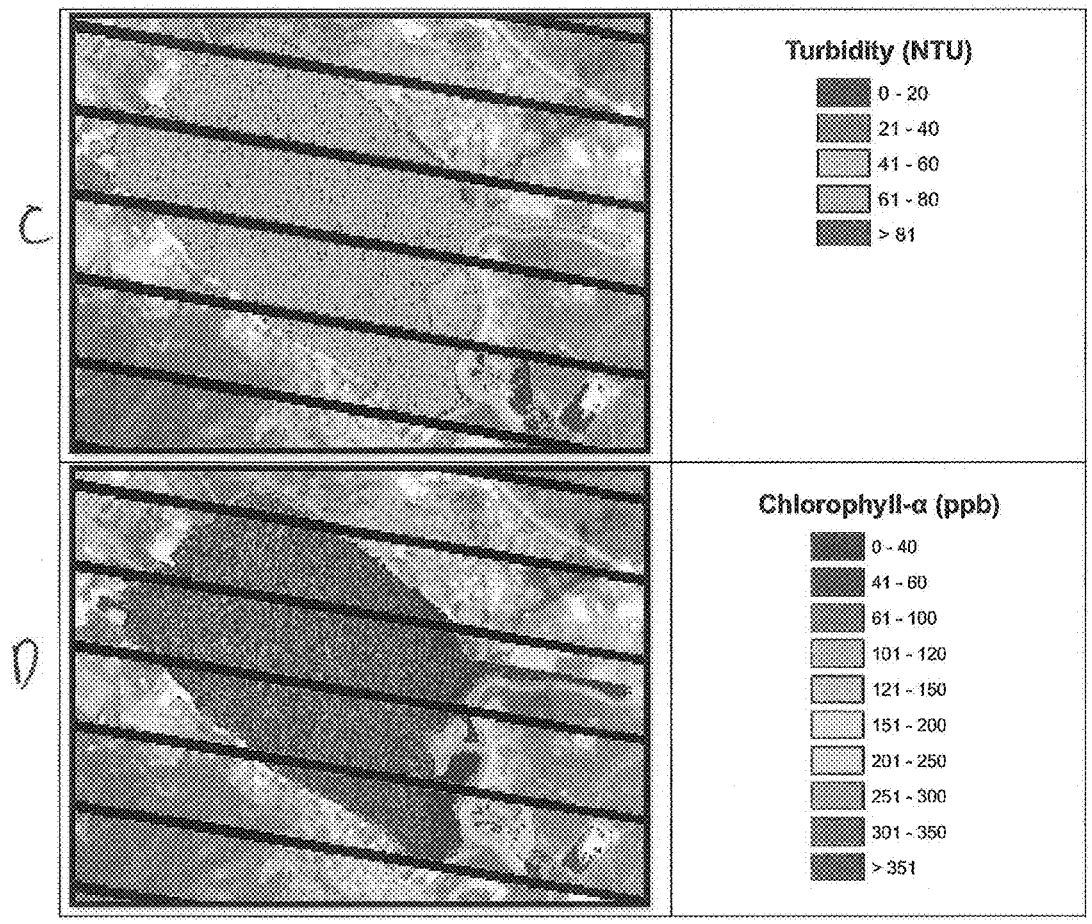
Figure 46:
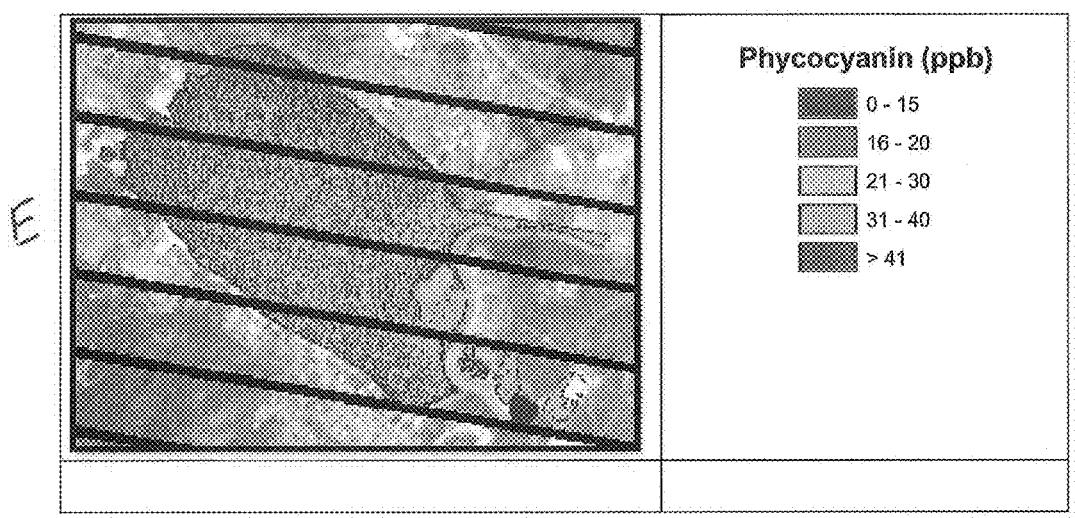
Figure 47:
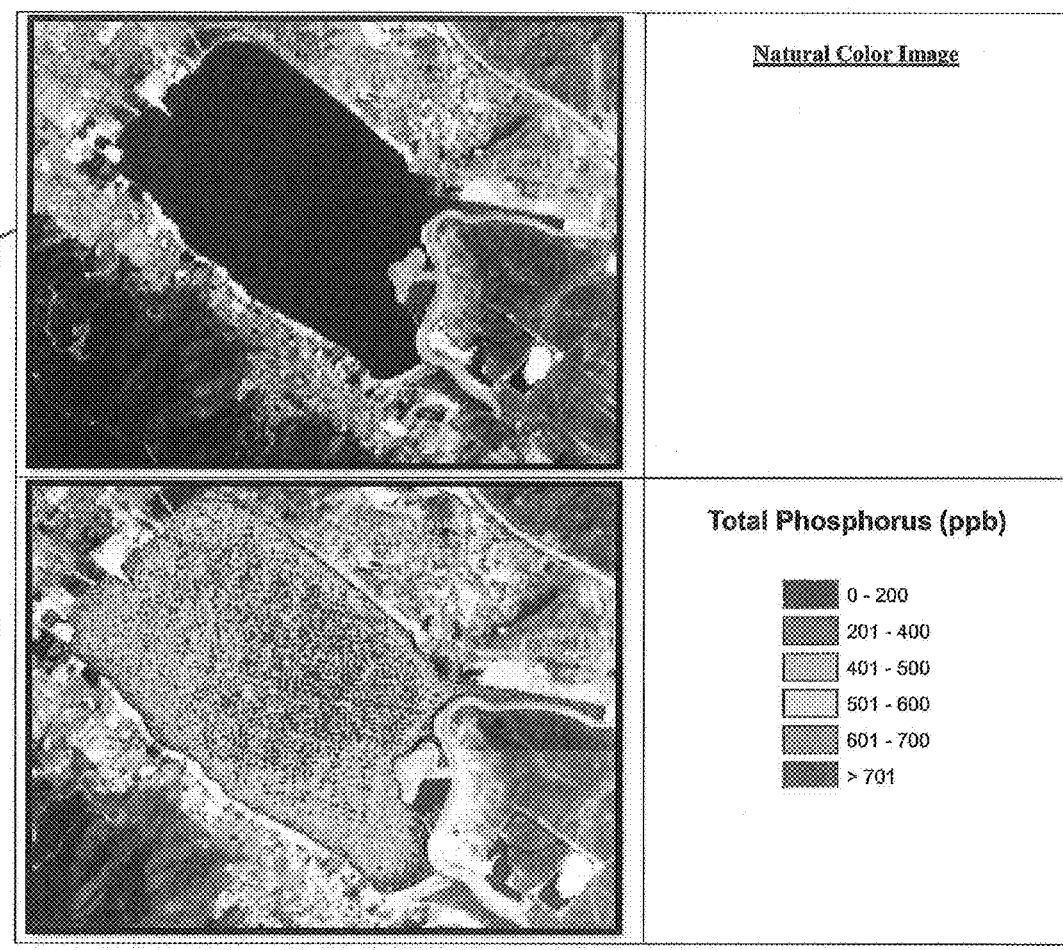
FIG. 47 in Appendix A shows data from a satellite passover on Jun. 14, 2004. Panel A is a natural color image. Panel B is the total phosphorus. Panel C is turbidity. Panel D is chlorophyll-α. Panel E is the TMDL exceedance for total phosphorus. Panel F is the TMDL exceedance chart for chlorophyll-α.
Figure 47:
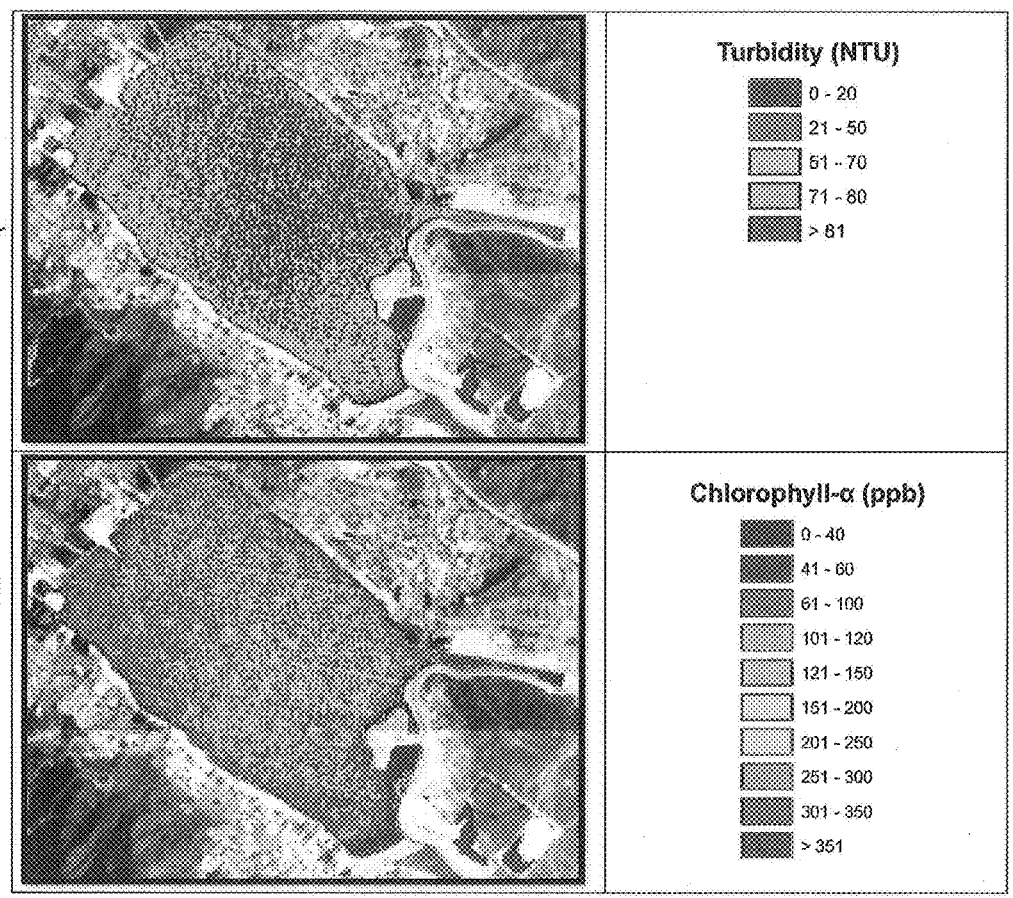
Figure 47:
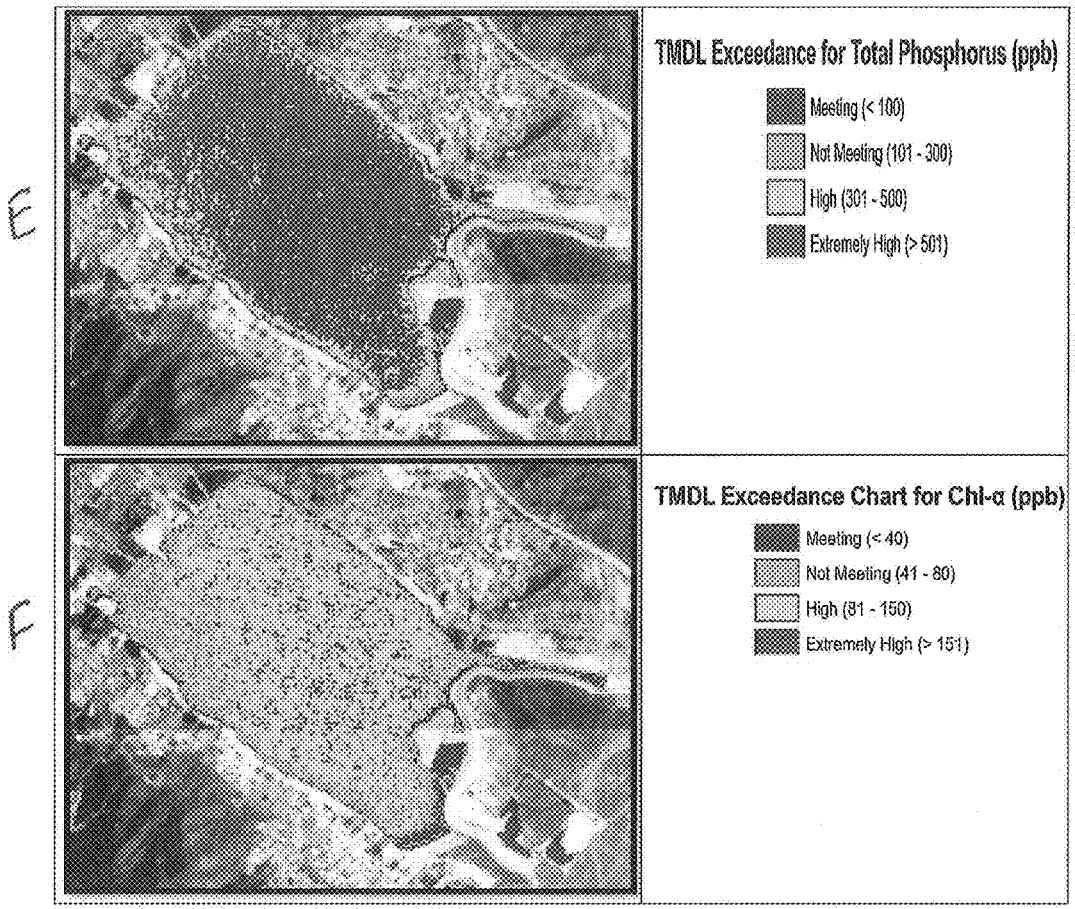
Figure 48:
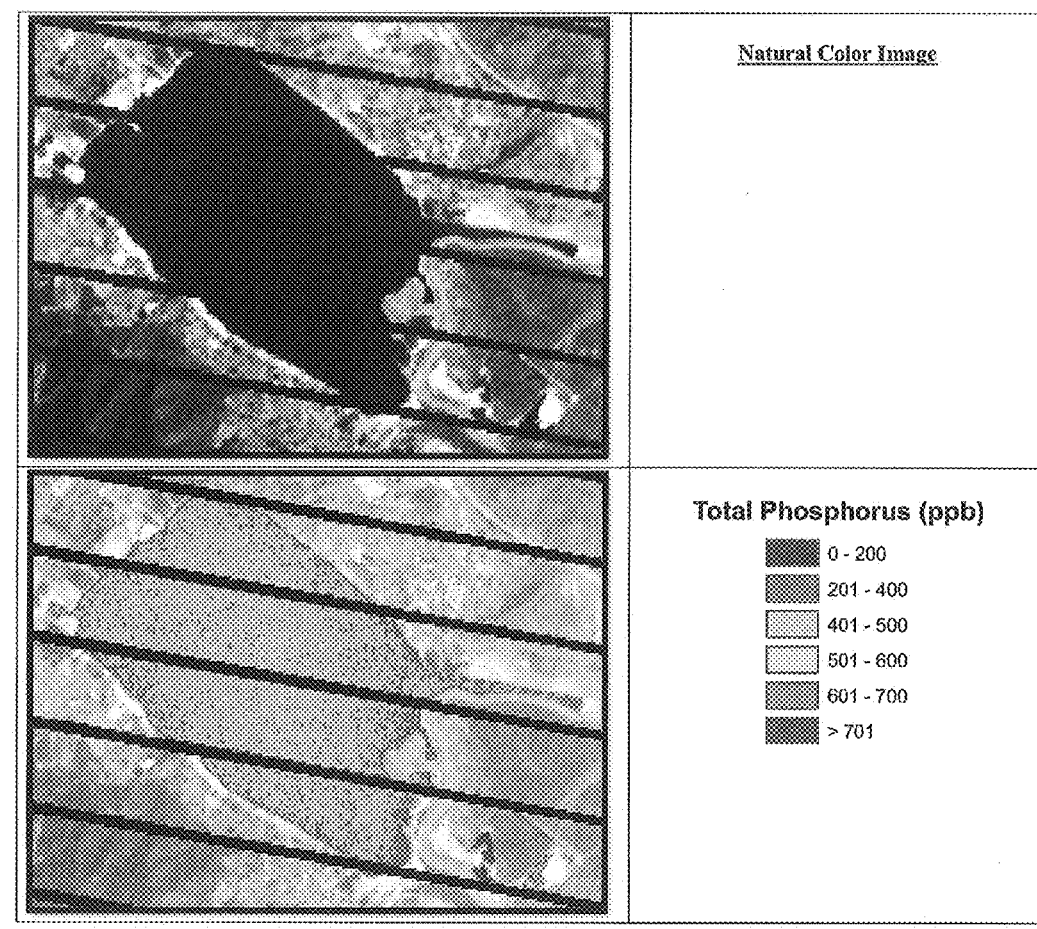
FIG. 48 in Appendix A shows data from a satellite passover on Aug. 9, 2004. Panel A is a natural color image. Panel B is the total phosphorus. Panel C is turbidity. Panel D is chlorophyll-α. Panel E is Phycocyanin.
Figure 48:
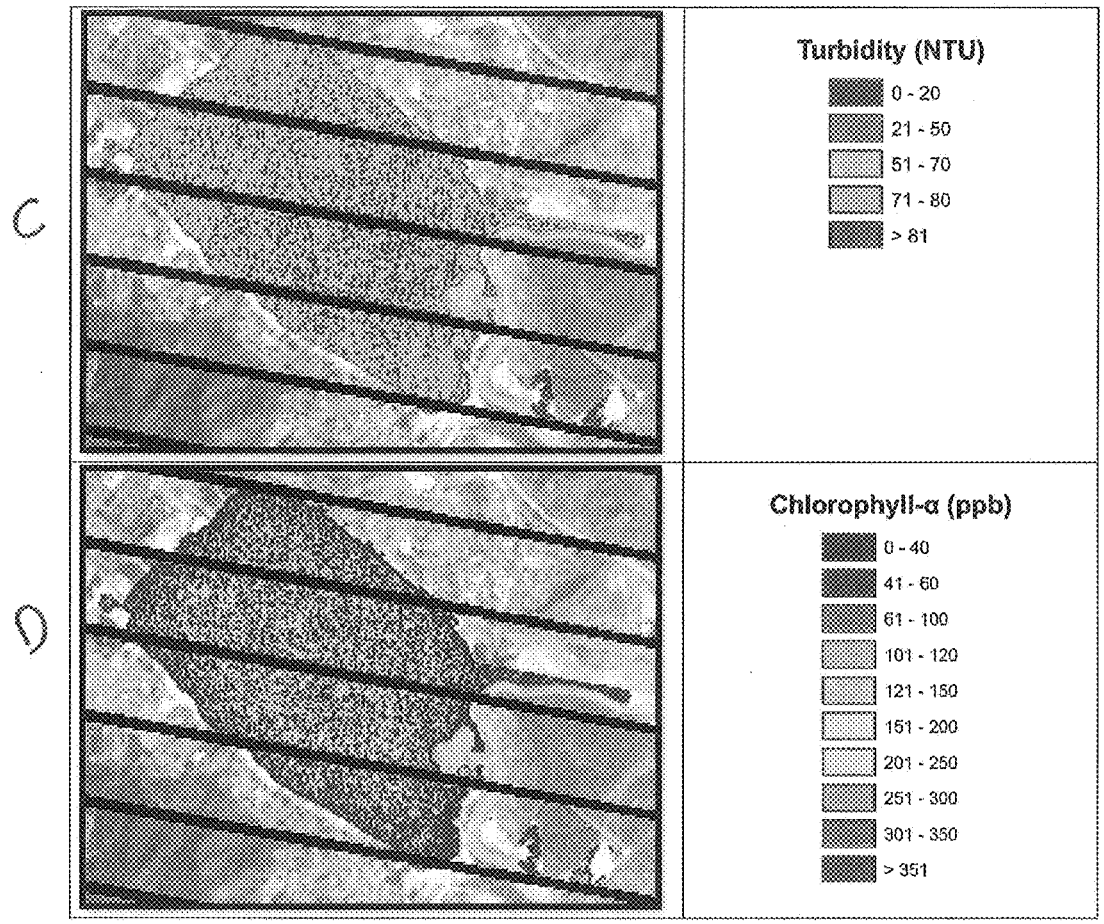
Figure 49:
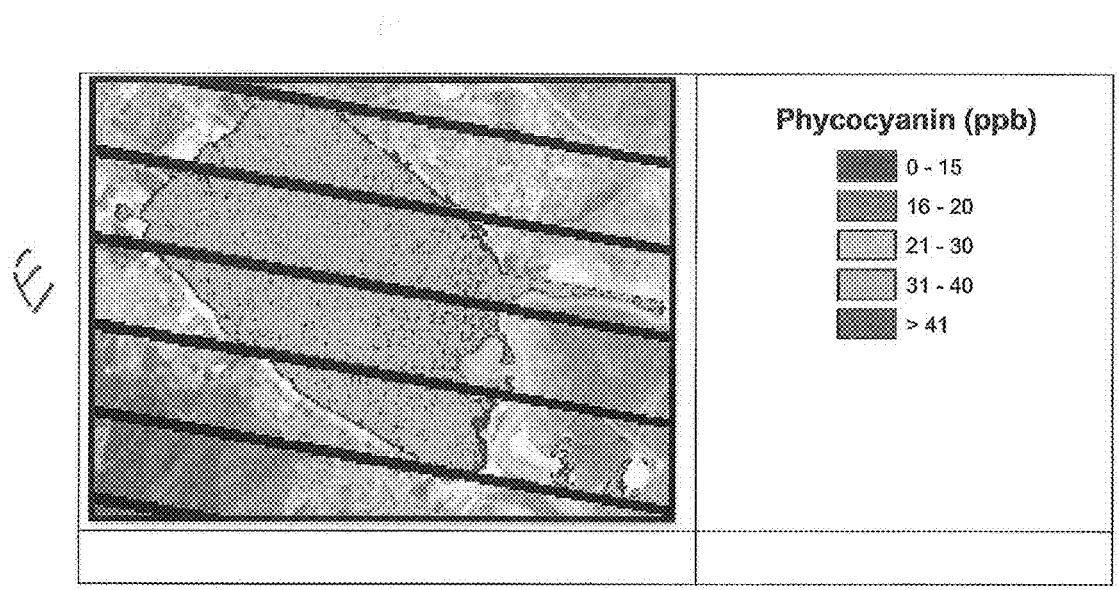
FIG. 49 in Appendix A shows data from a satellite passover on Oct. 4, 2004. Panel A is a natural color image. Panel B is the total phosphorus. Panel C is turbidity. Panel D is chlorophyll-α.
Figure 49:
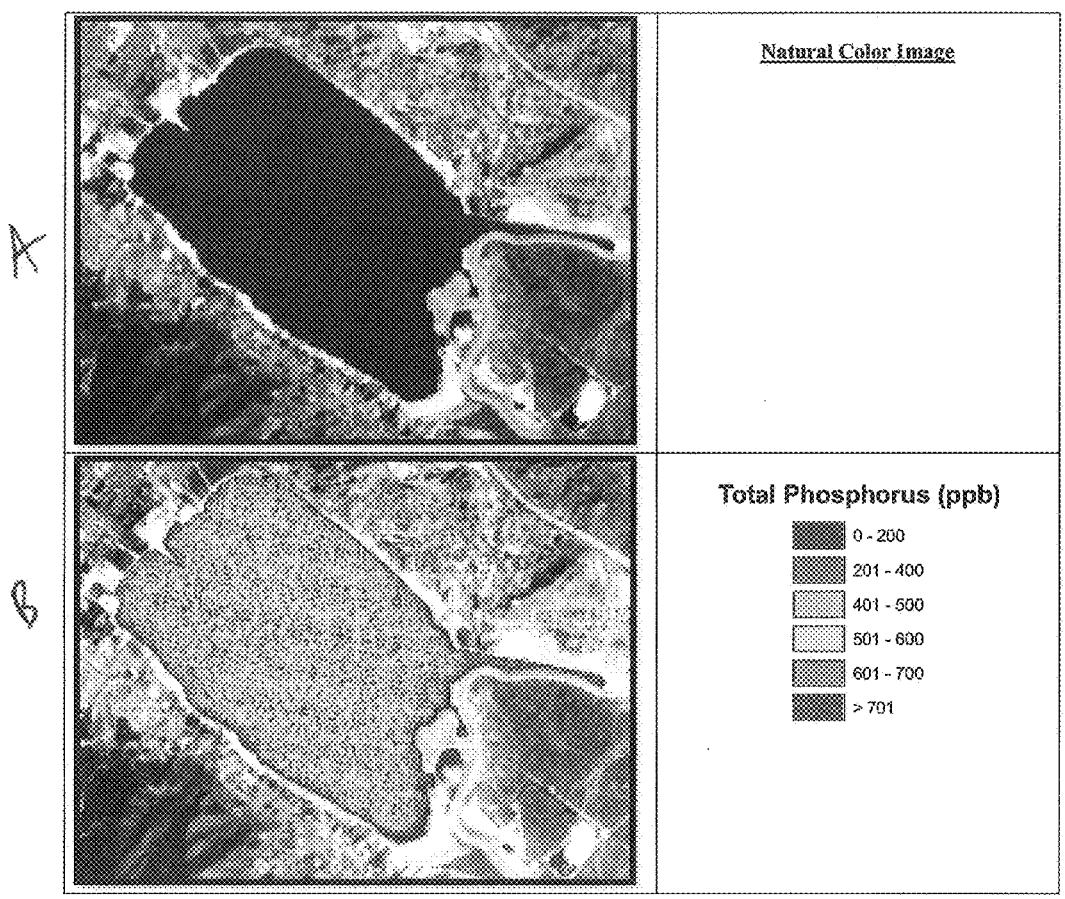
Figure 49:
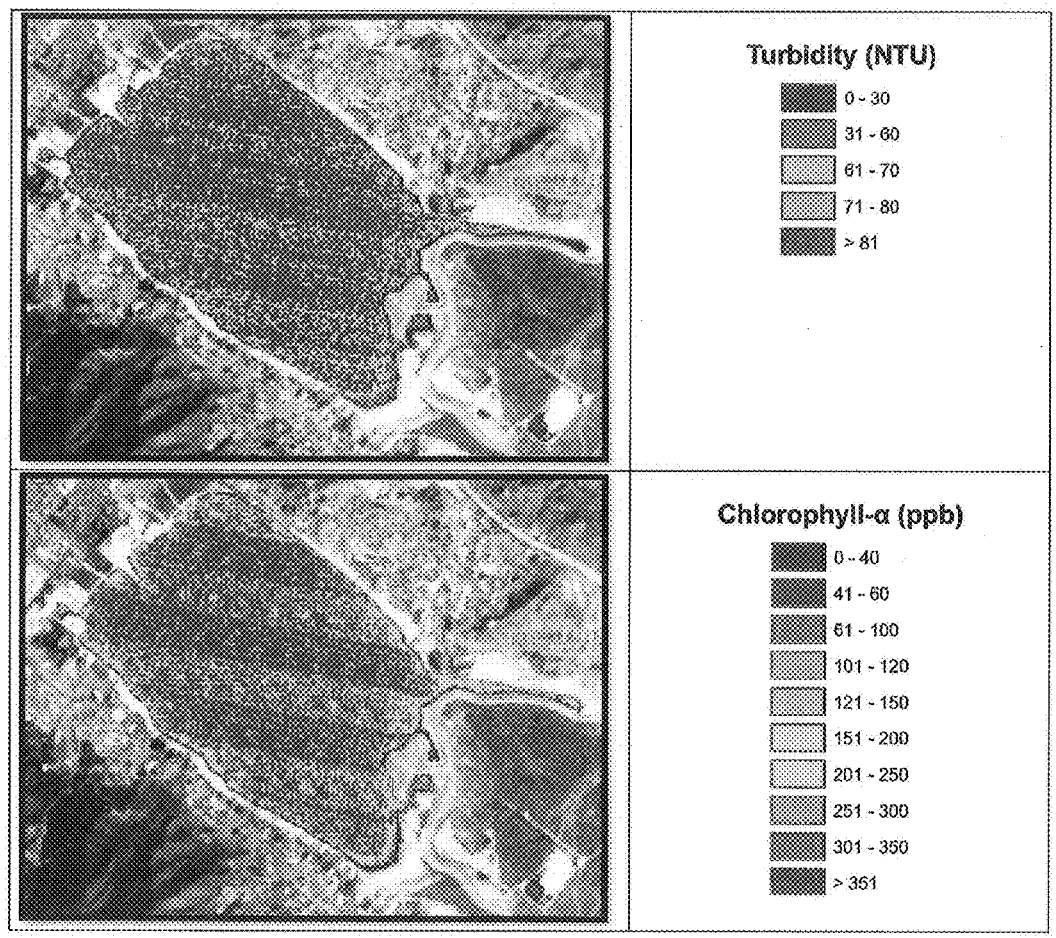
Figure 50:
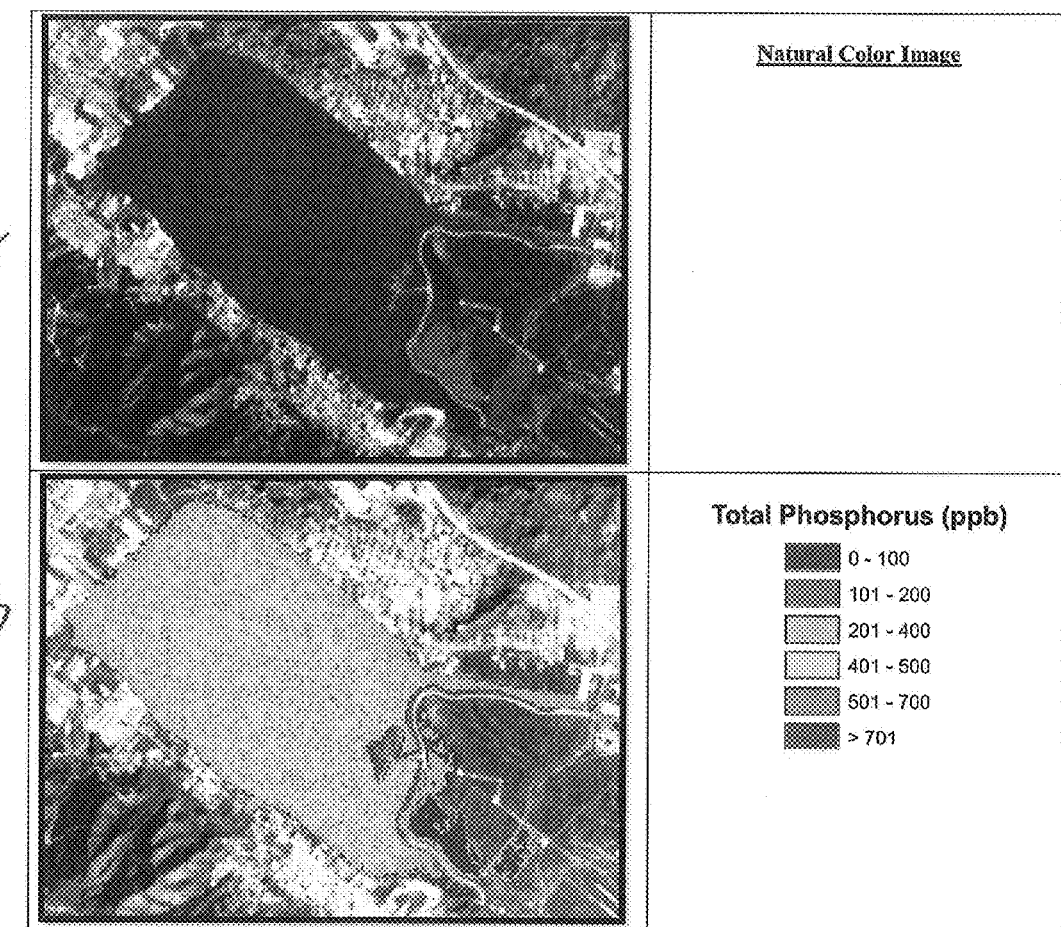
FIG. 50 in Appendix A shows data from a satellite passover on Feb. 9, 2005. Panel A is a natural color image. Panel B is the total phosphorus. Panel C is turbidity. Panel D is chlorophyll-α. Panel E is the TMDL exceedance for total phosphorus. Panel F is the TMDL exceedance chart for chlorophyll-α.
Figure 56:
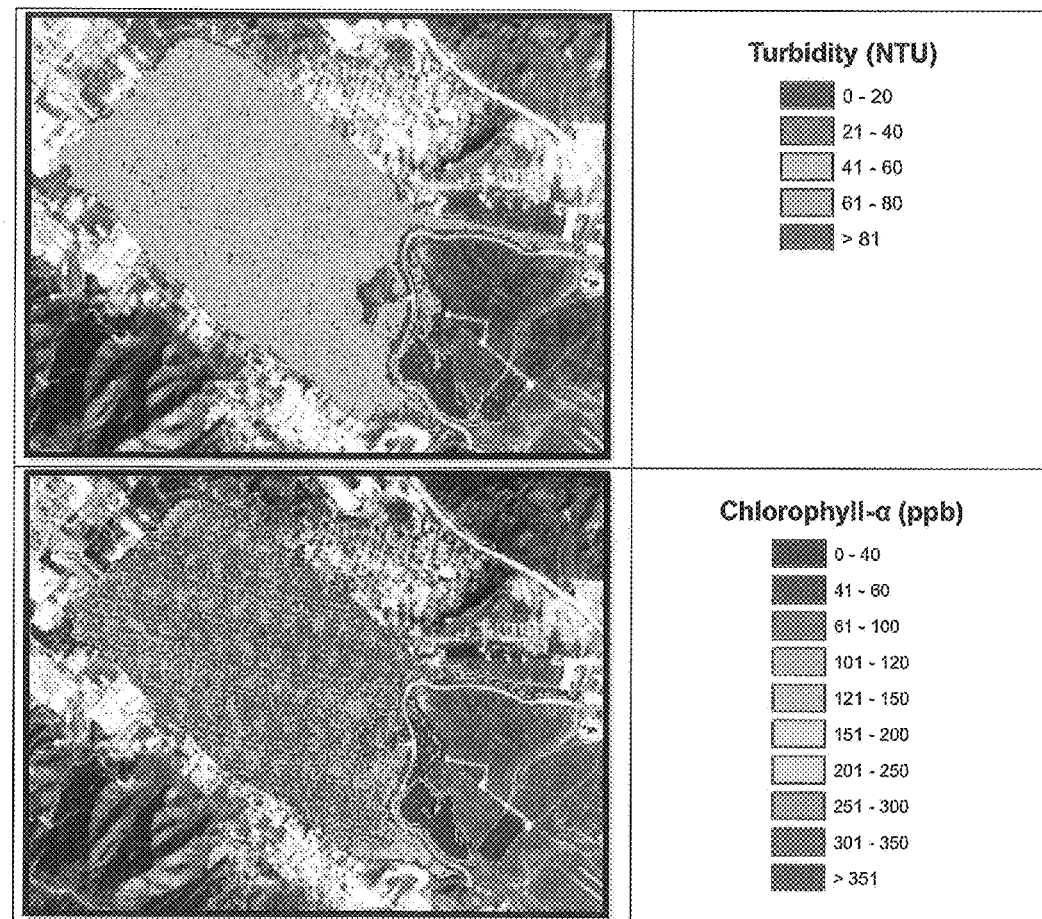
FIG. 56 in Appendix A shows data from a satellite passover on Mar. 21, 2008. Panel A is a natural color image. Panel B is the total phosphorus. Panel C is turbidity. Panel D is the TMDL exceedance for total phosphorus.
Figure 50:
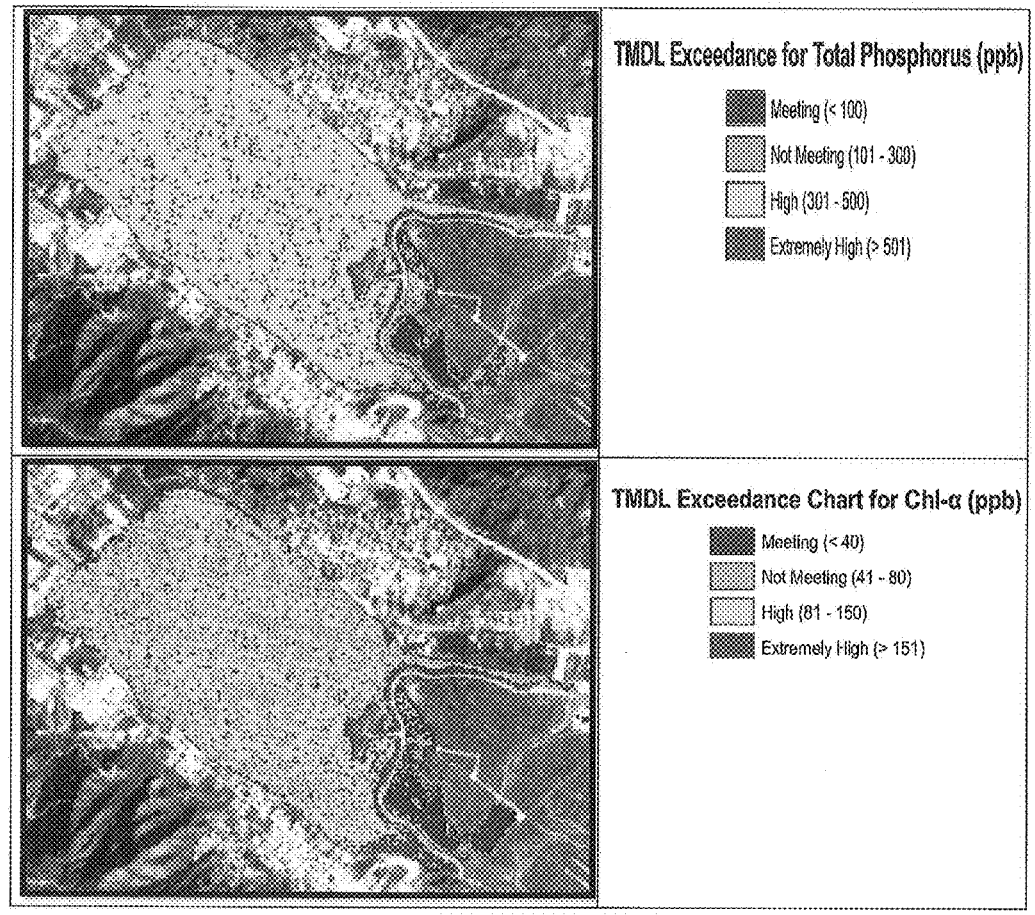
Figure 51:
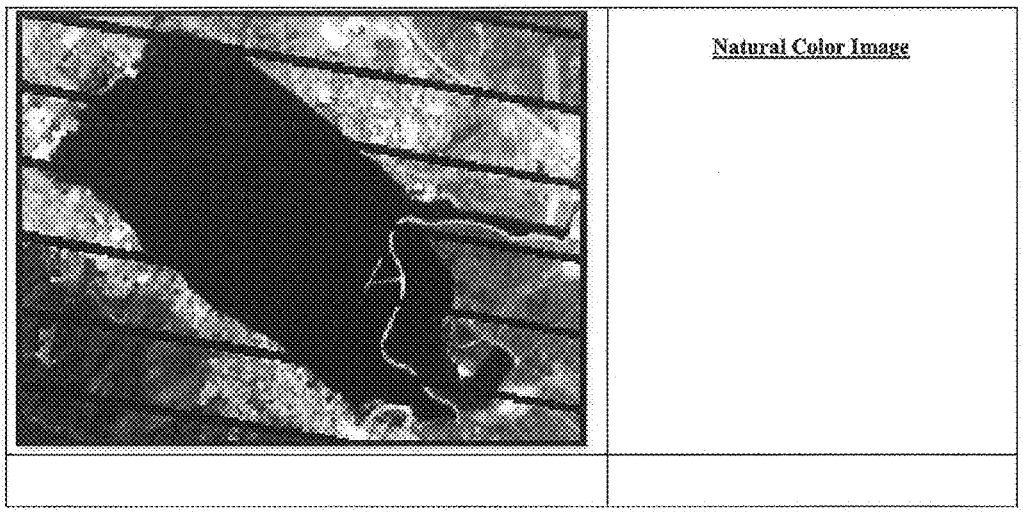
FIG. 51 in Appendix A shows data from a satellite passover on Jul. 27, 2005. Panel A is a natural color image. Panel B is turbidity. Panel C is phycocyanin.
Figure 51:
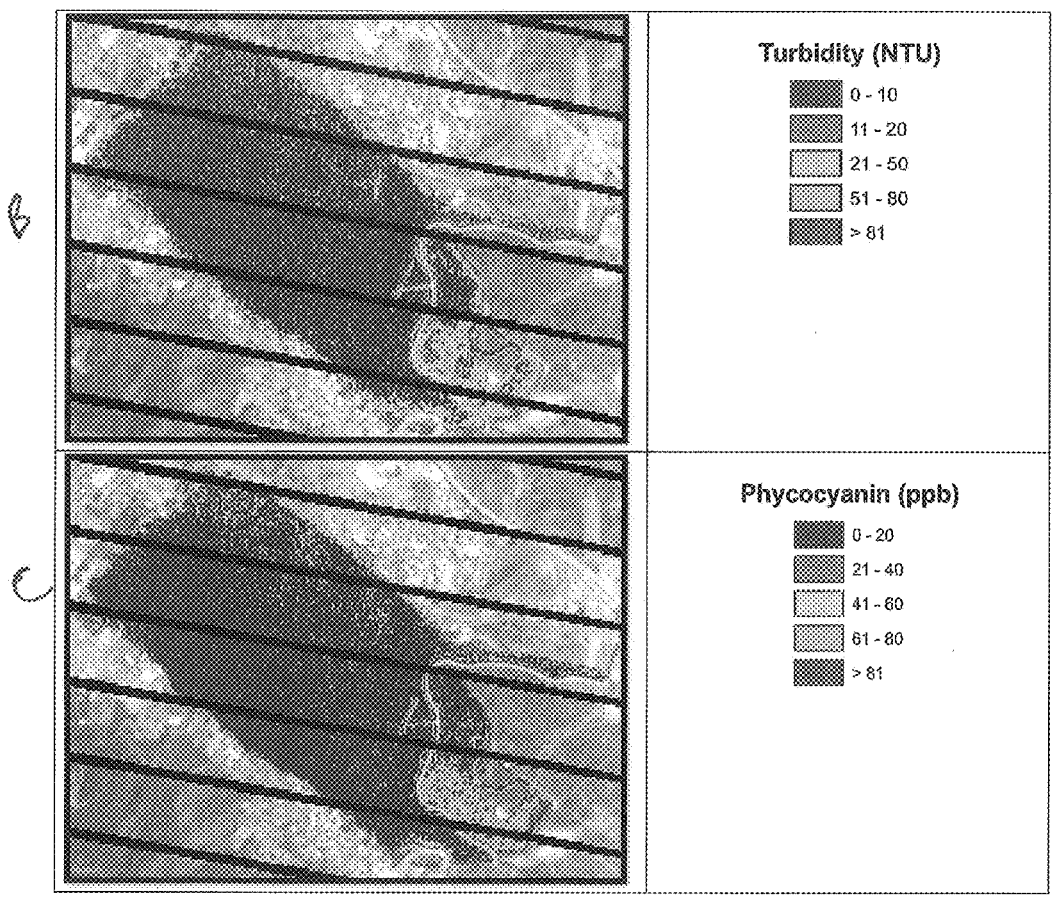
Figure 52:
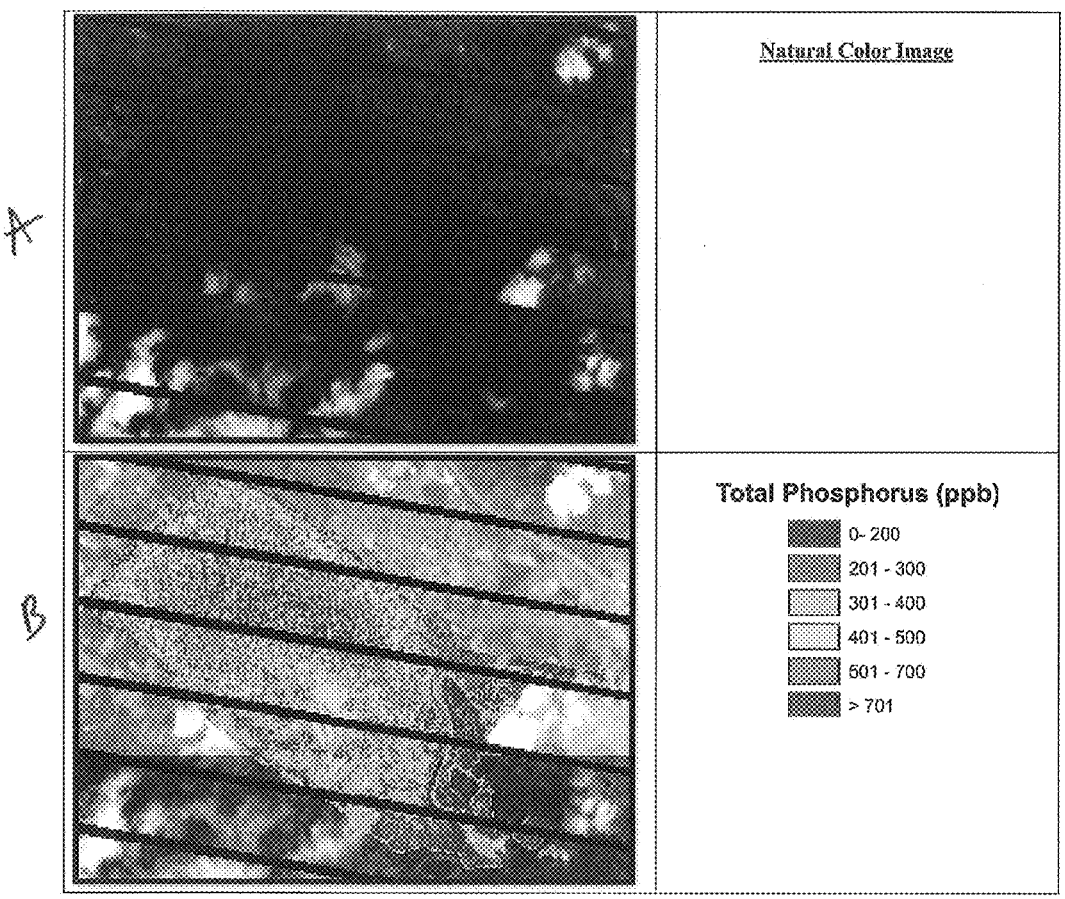
FIG. 52 in Appendix A shows data from a satellite passover on Apr. 25, 2006. Panel A is a natural color image. Panel B is the total phosphorus. Panel C is turbidity. Panel D is chlorophyll-α. Panel E is phycocyanin.
Figure 52:
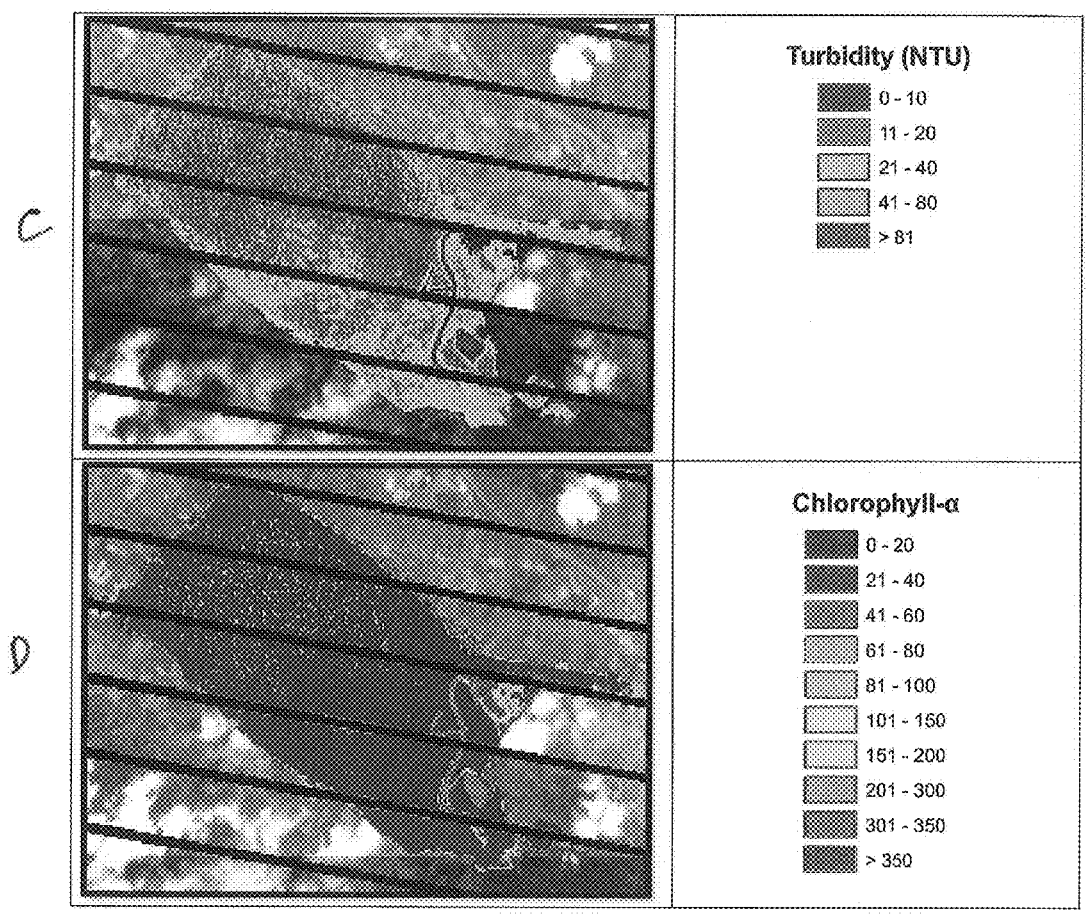
Figure 52:
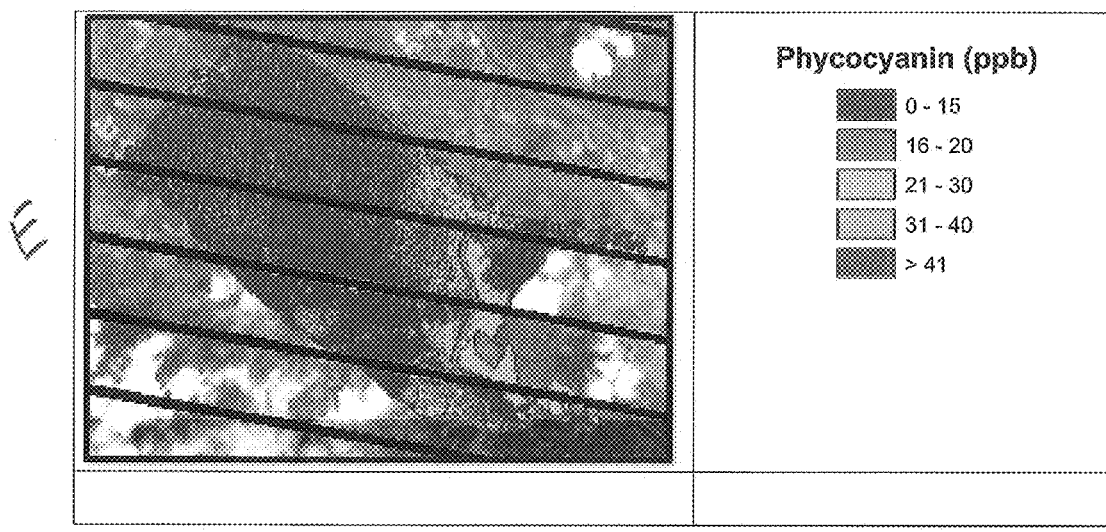
Figure 53:
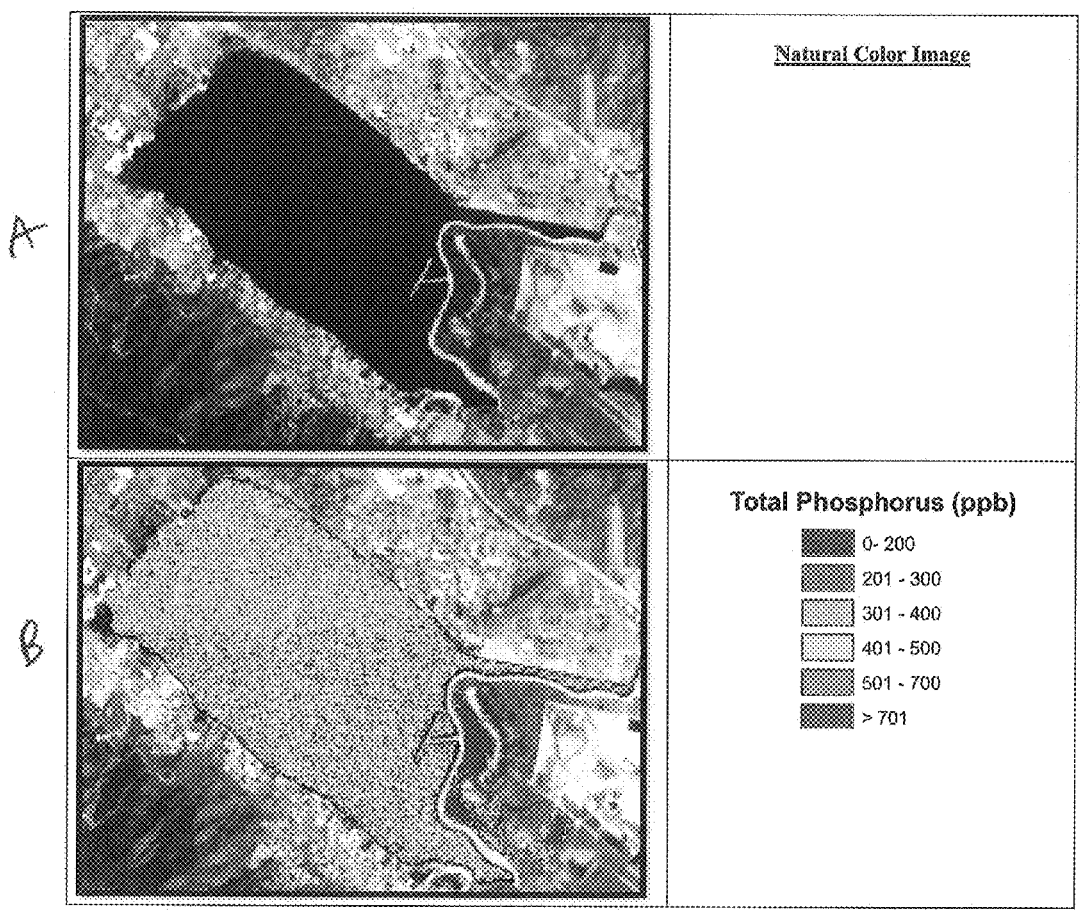
FIG. 53 in Appendix A shows data from a satellite passover on Jun. 6, 2006. Panel A is a natural color image. Panel B is the total phosphorus. Panel C is turbidity. Panel D is chlorophyll-α. Panel E is the TMDL exceedance for total phosphorus. Panel F is the TMDL exceedance chart for chlorophyll-α.
Figure 53:
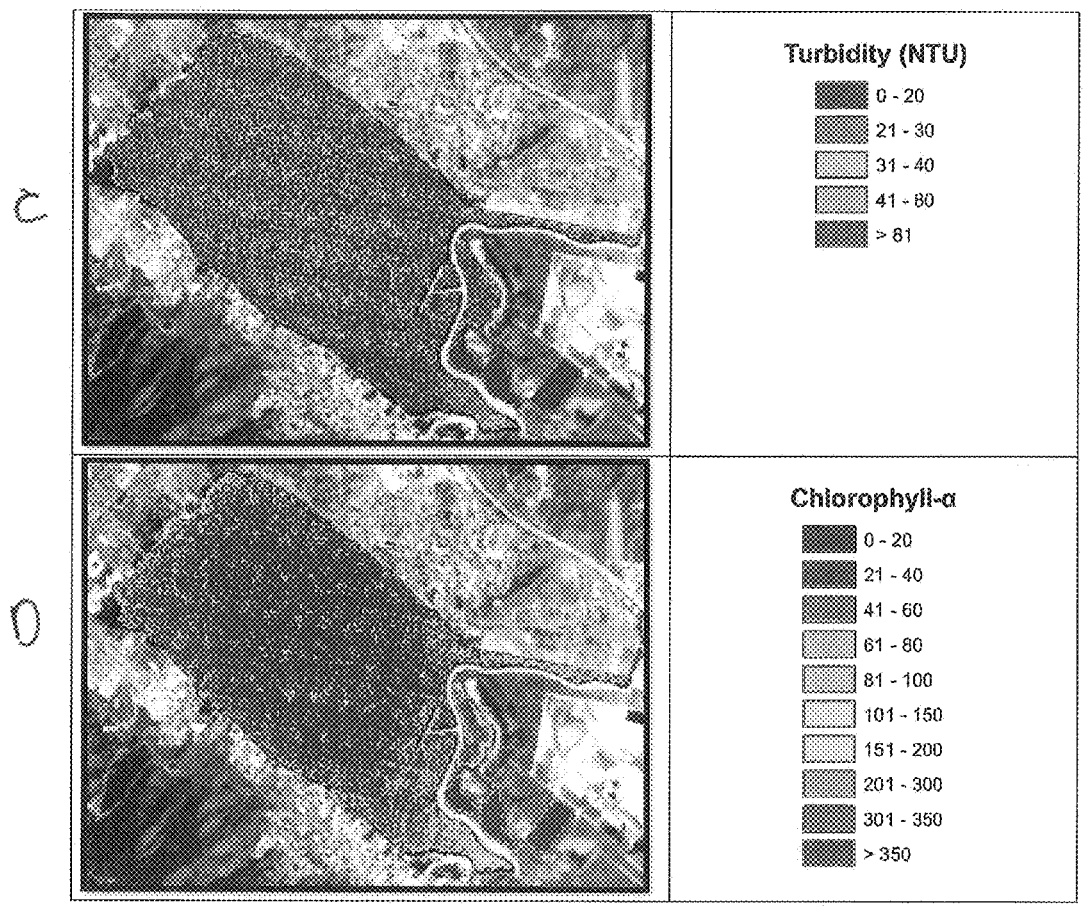
Figure 53:
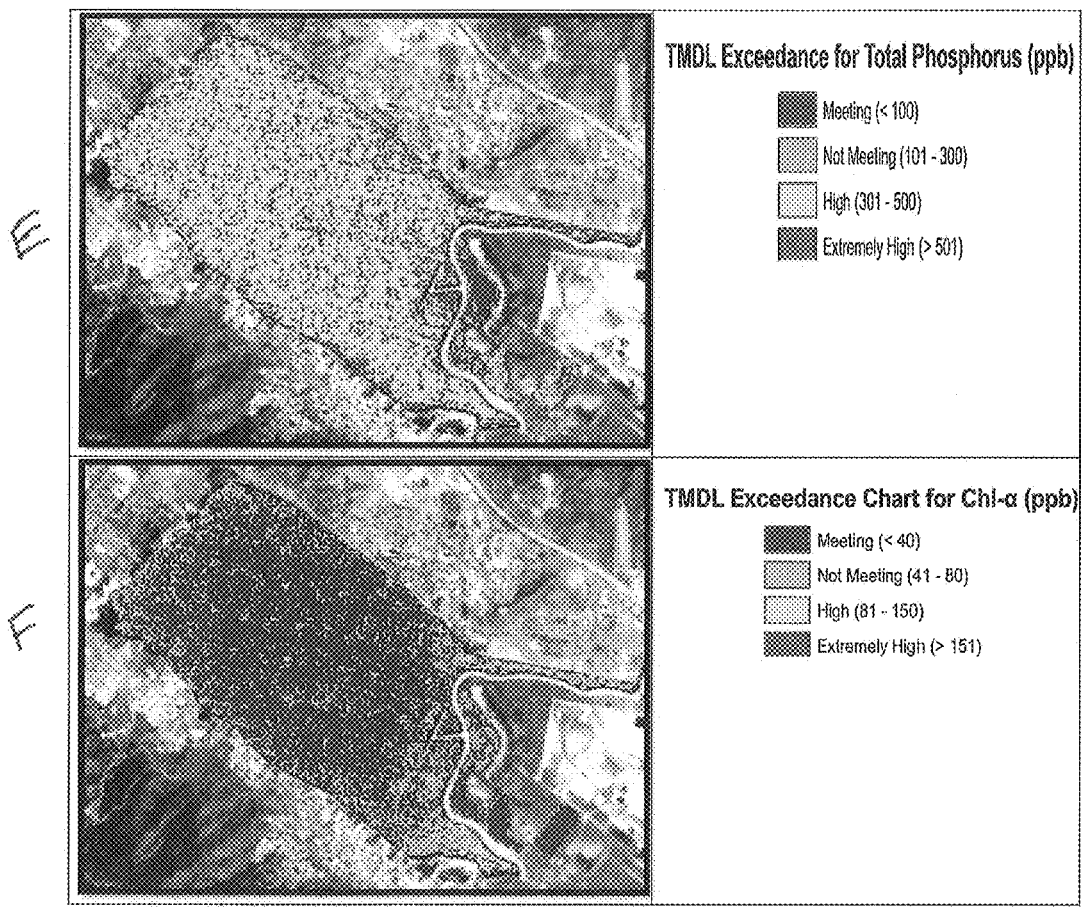
Figure 54:
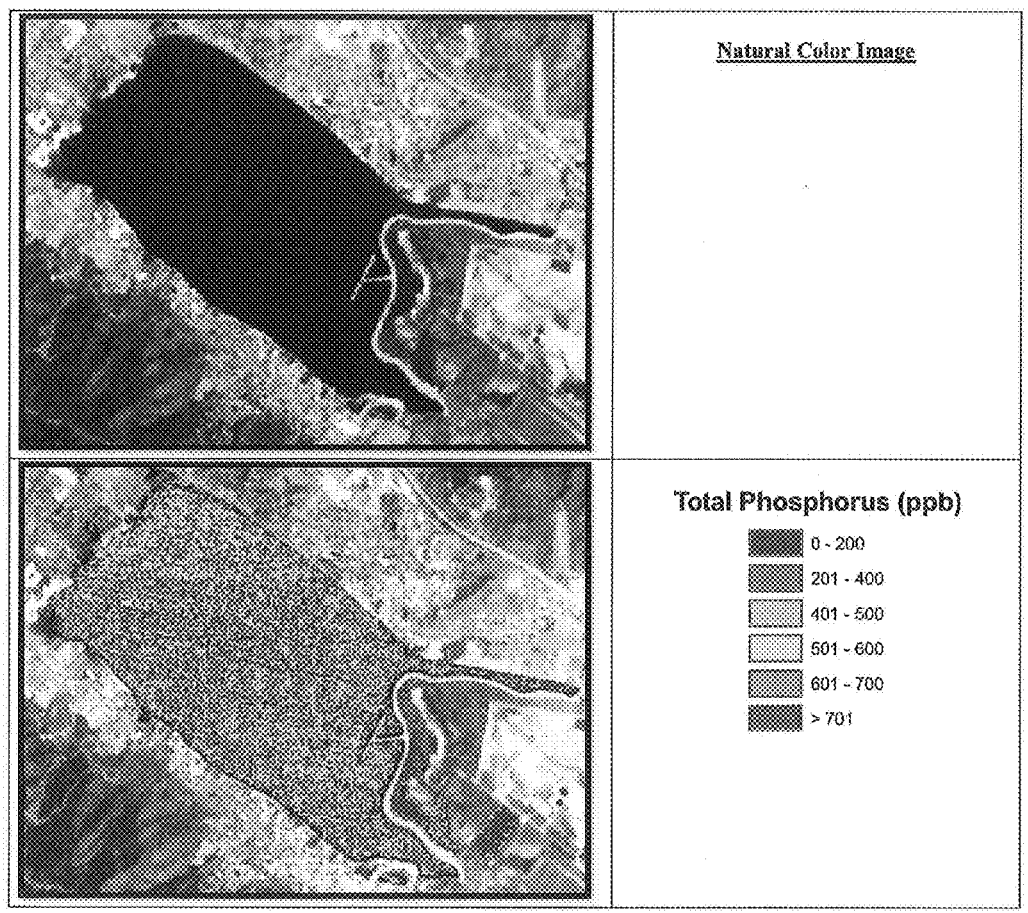
FIG. 54 in Appendix A shows data from a satellite passover on Jul. 6, 2006. Panel A is a natural color image. Panel B is the total phosphorus. Panel C is turbidity. Panel D is chlorophyll-α.
Figure 54:
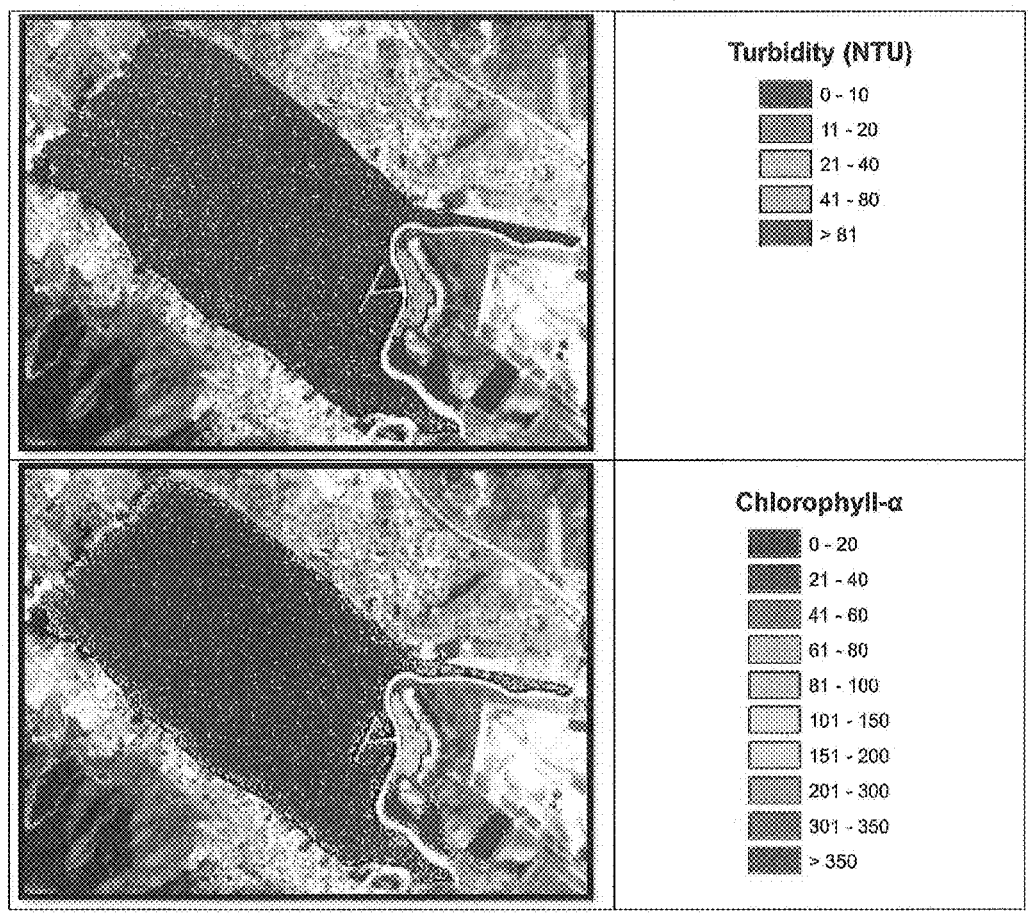
Figure 55:
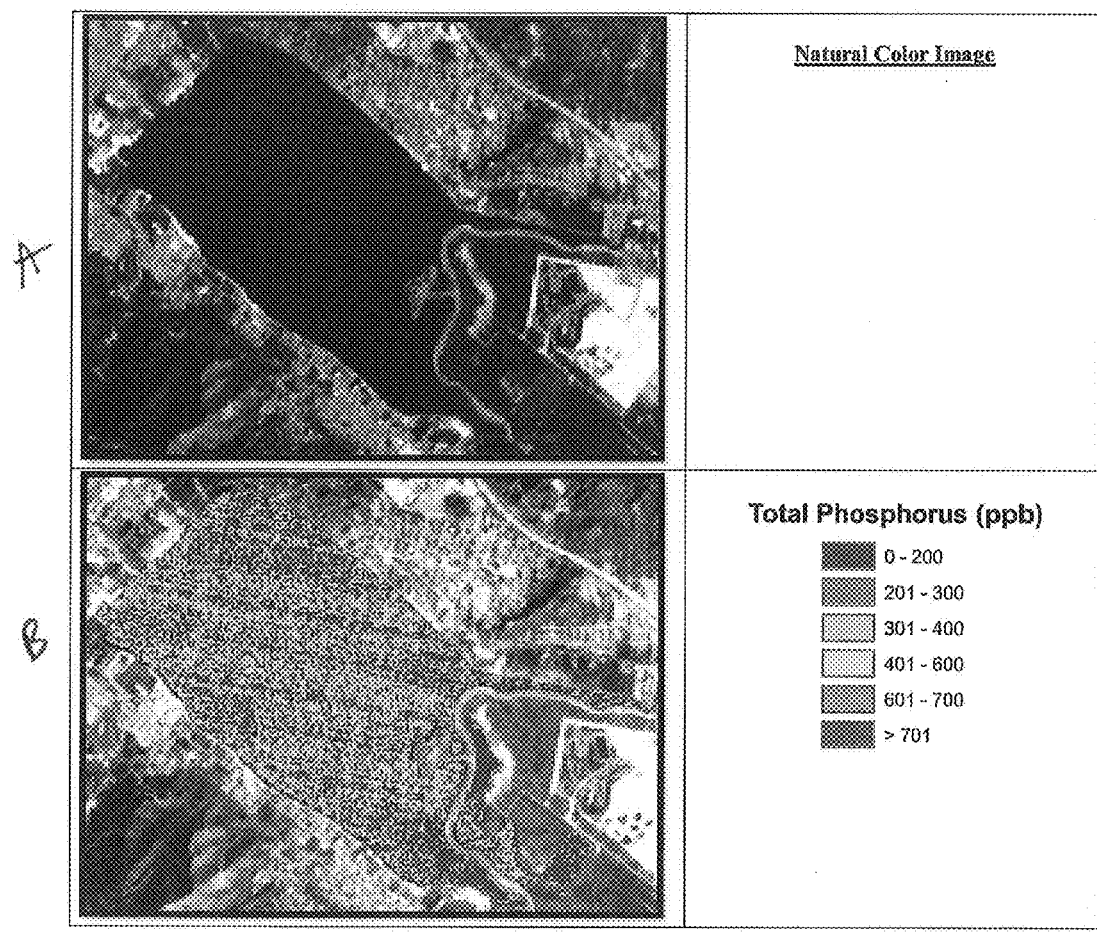
FIG. 55 in Appendix A shows data from a satellite passover on Mar. 5, 2008. Panel A is a natural color image. Panel B is the total phosphorus. Panel C is turbidity.
Figure 55:
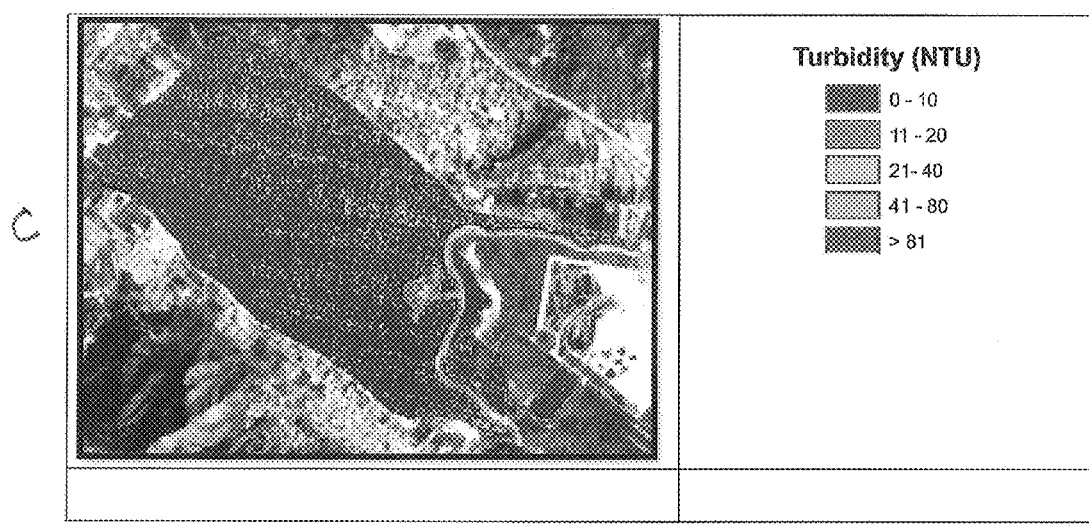
Figure 56:
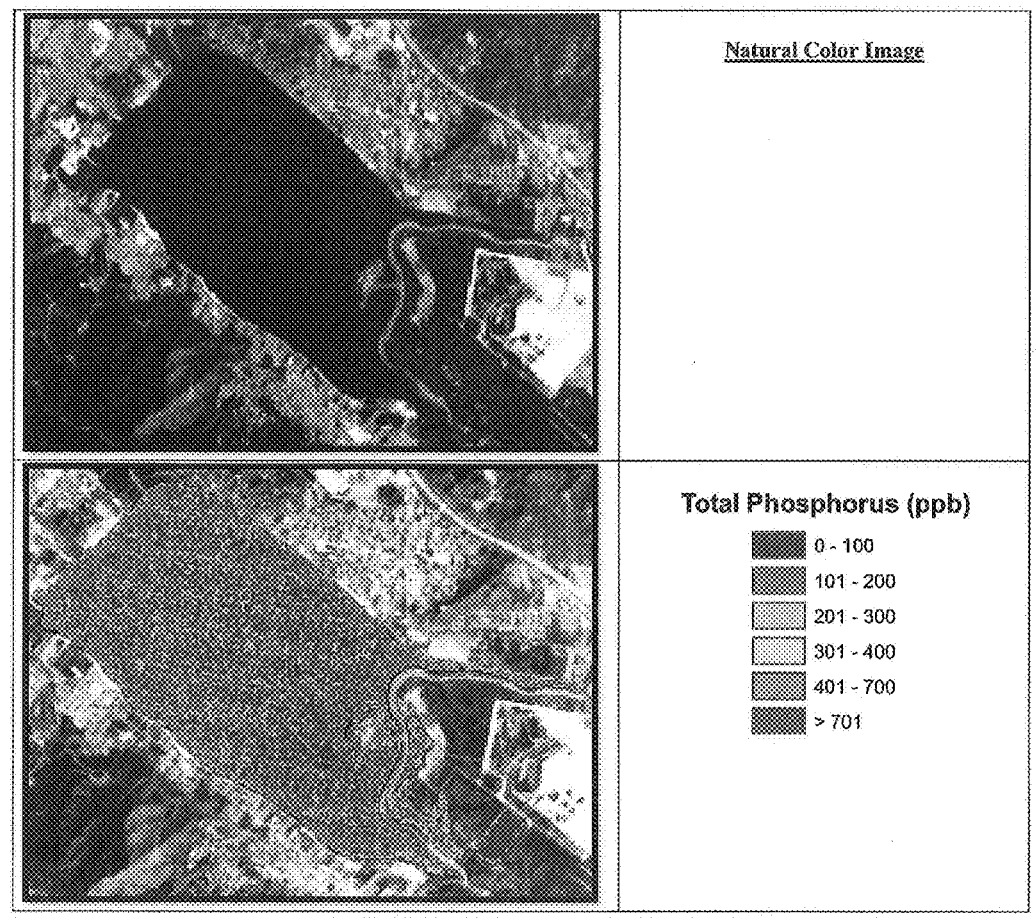
Figure 56:
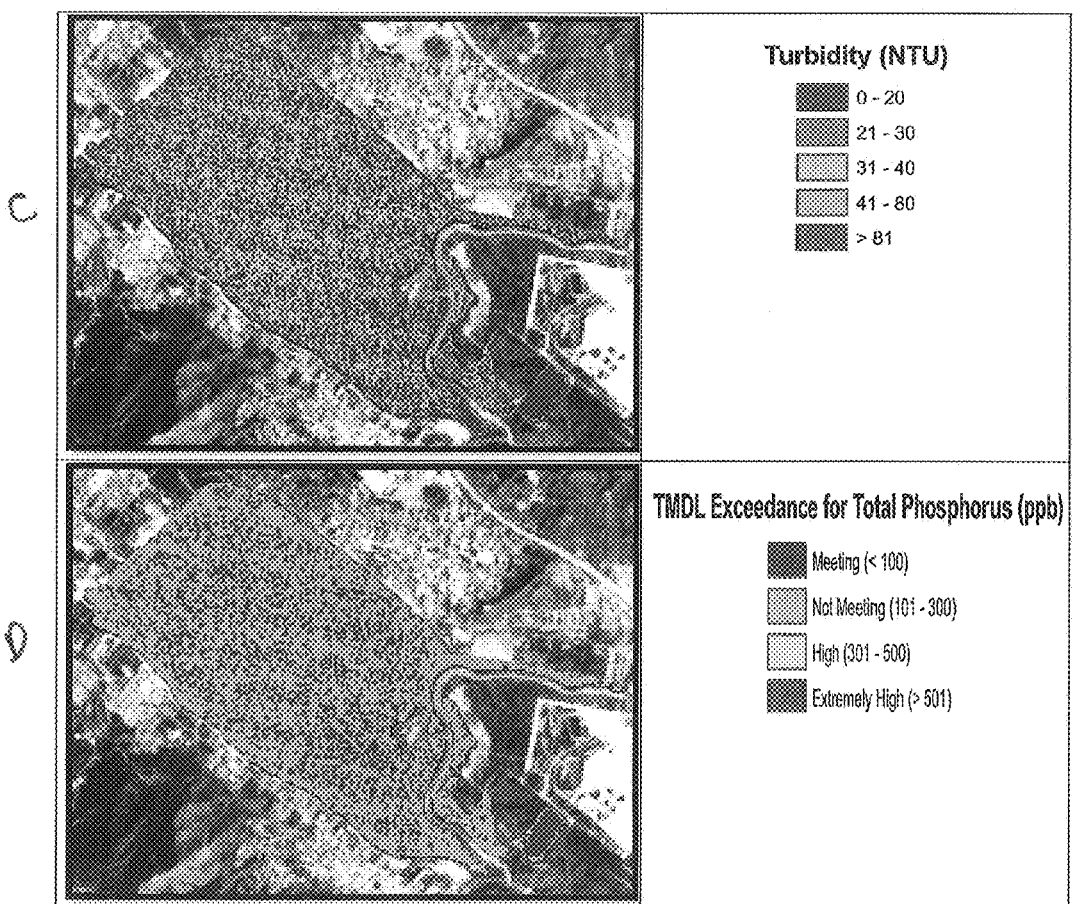
Figure 57:
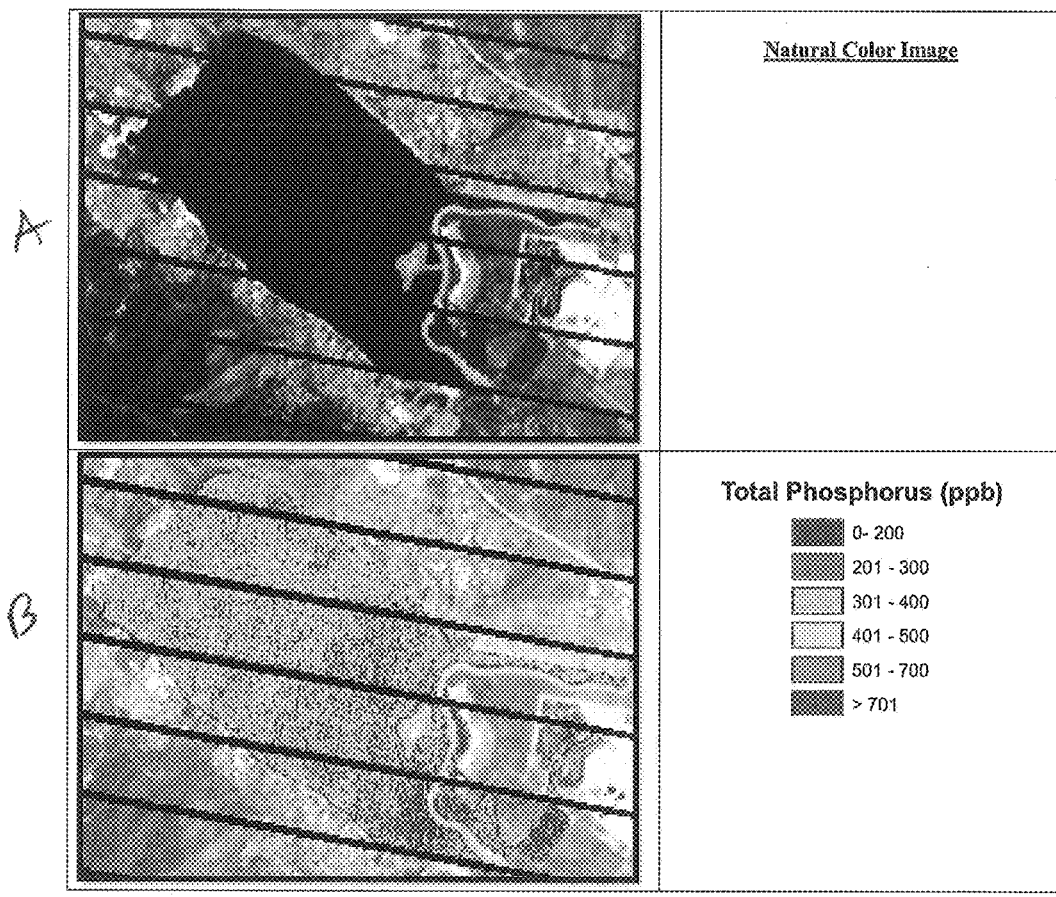
FIG. 57 in Appendix A shows data from a satellite passover on May 16, 2008. Panel A is a natural color image. Panel B is the total phosphorus. Panel C is turbidity. Panel D is chlorophyll-α. Panel E is phycocyanin.
Figure 57:
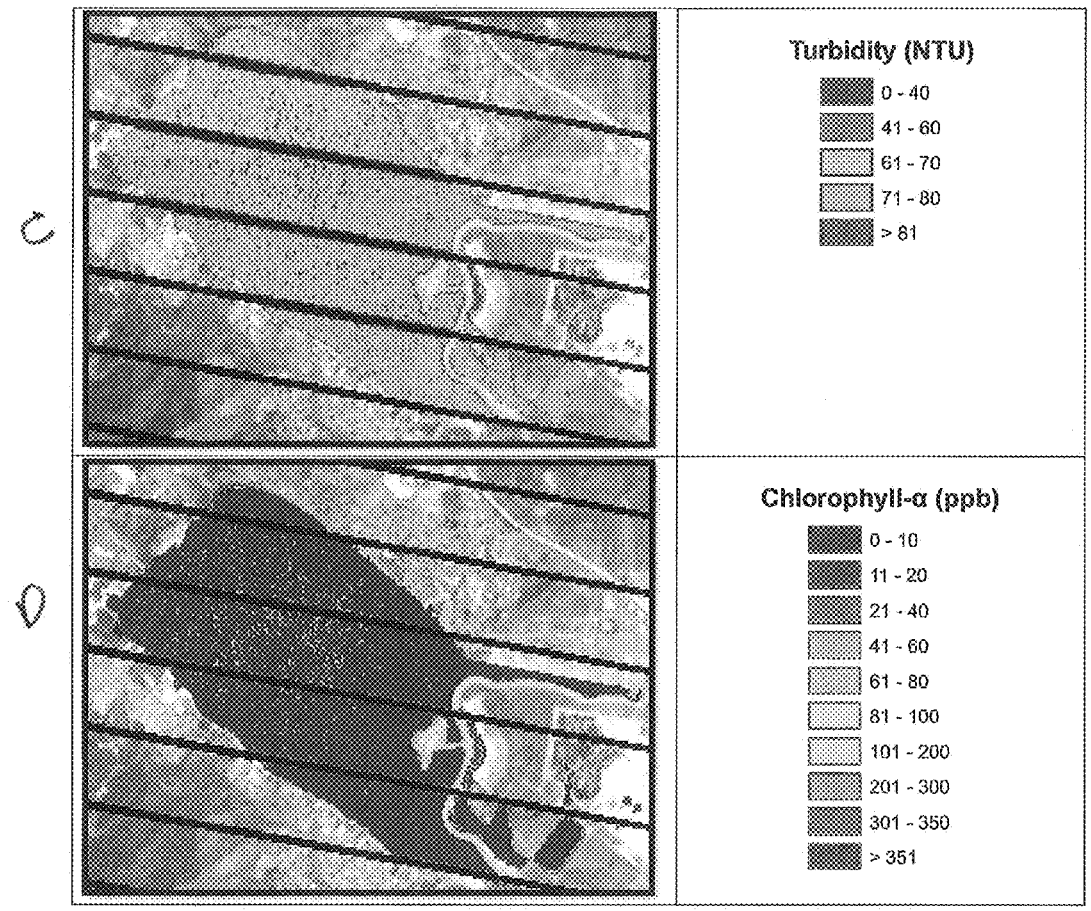
Figure 57:
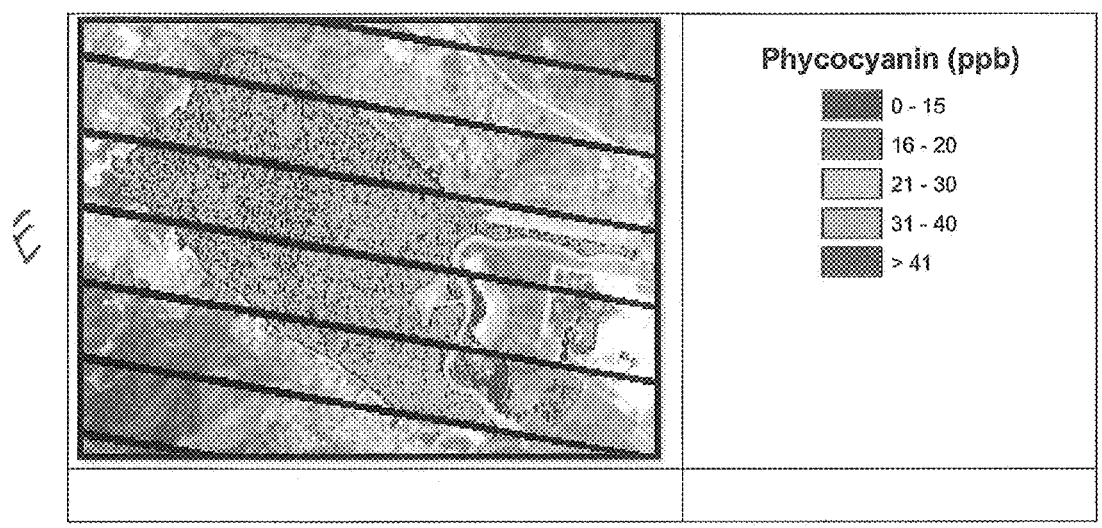
Figure 59:
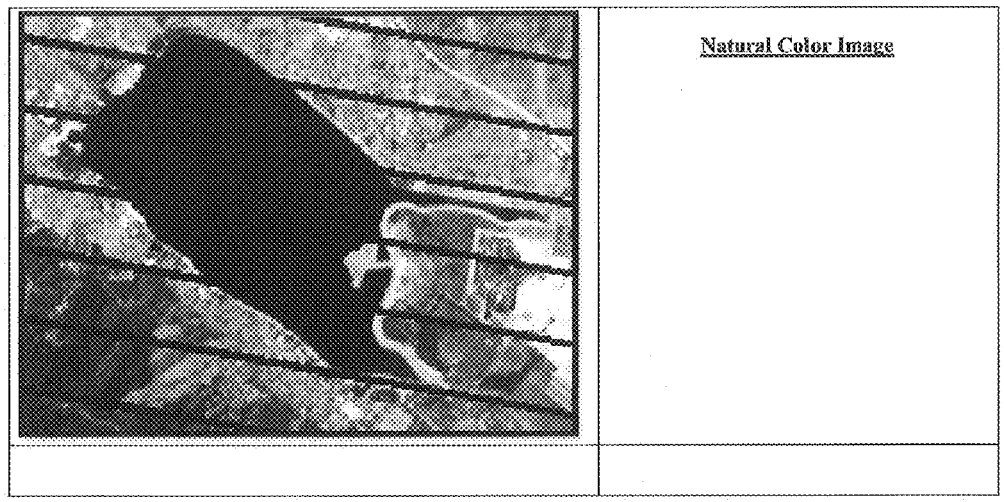
FIG. 59 in Appendix A shows data from a satellite passover on Mar. 24, 2009. Panel A is a natural color image. Panel B is the total phosphorus. Panel C is turbidity. Panel D is chlorophyll-α. Panel E is the TMDL exceedance for total phosphorus. Panel F is the TMDL exceedance chart for chlorophyll-α.
Figure 58:
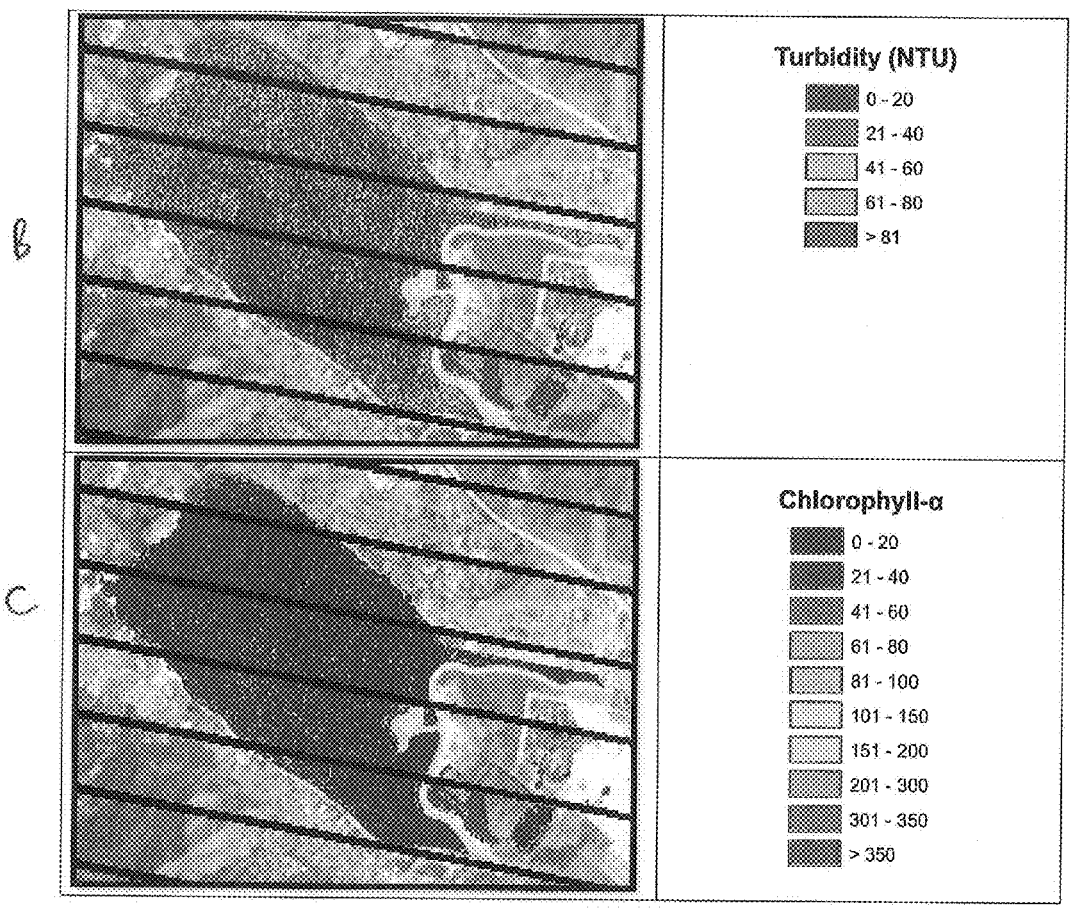
FIG. 58 in Appendix A shows data from a satellite passover on Aug. 20, 2008. Panel A is a natural color image. Panel B is turbidity. Panel C is chlorophyll-α. Panel D is phycocyanin.
Figure 58:
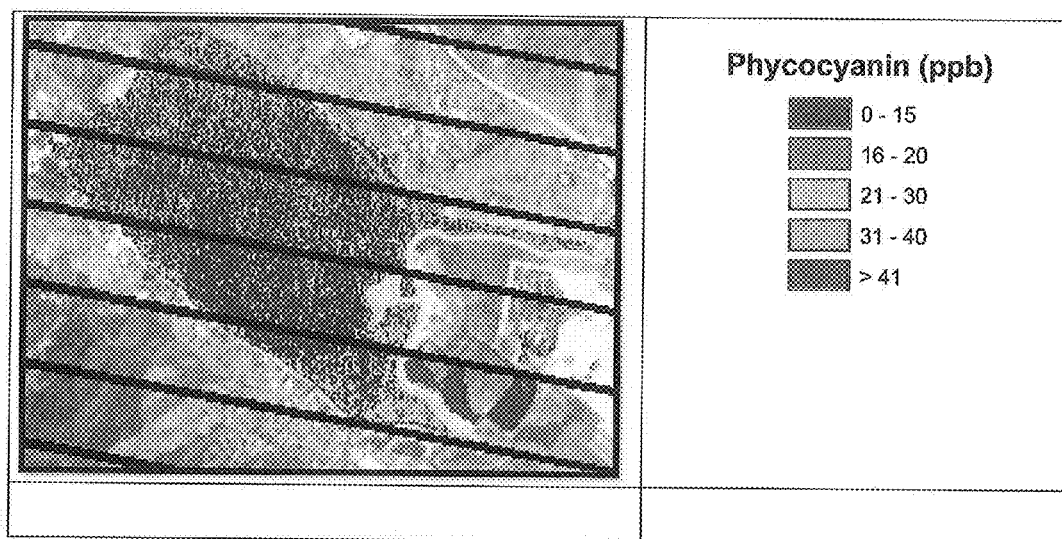
Figure 59:
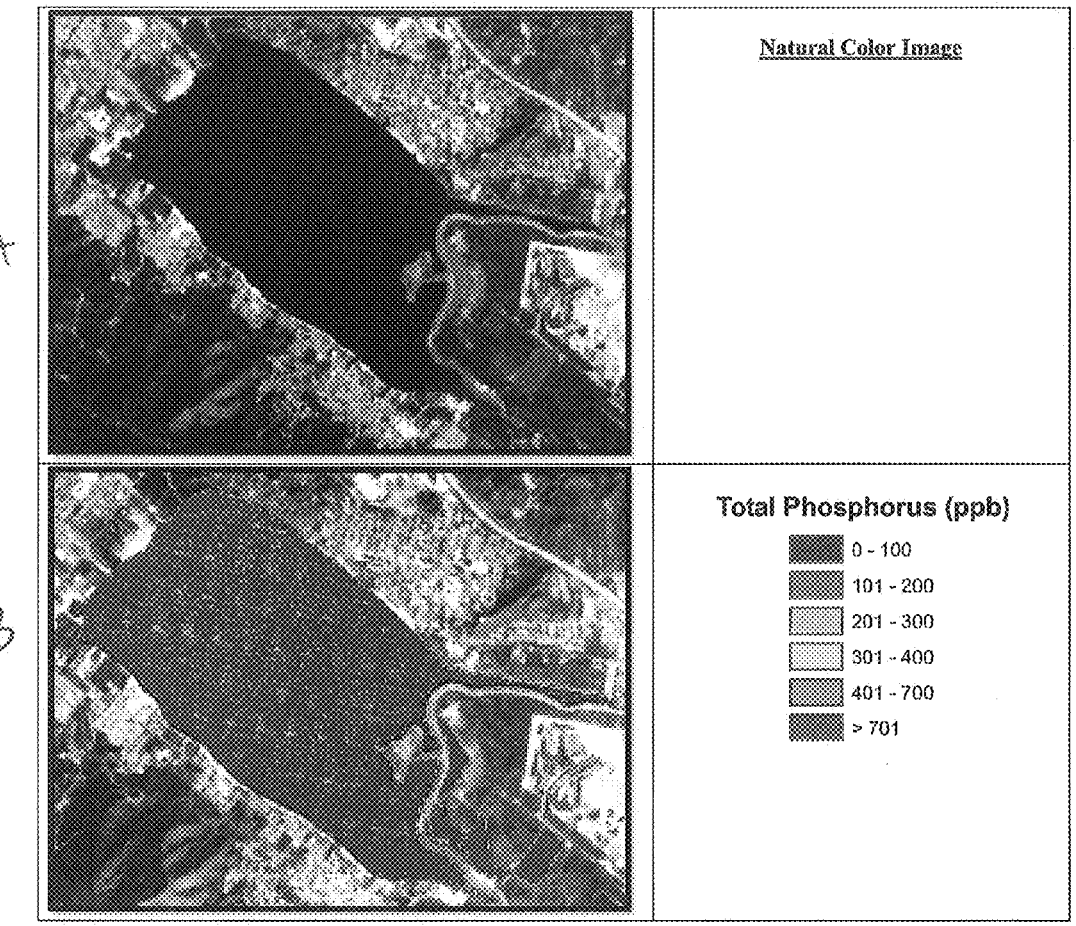
Figure 59:
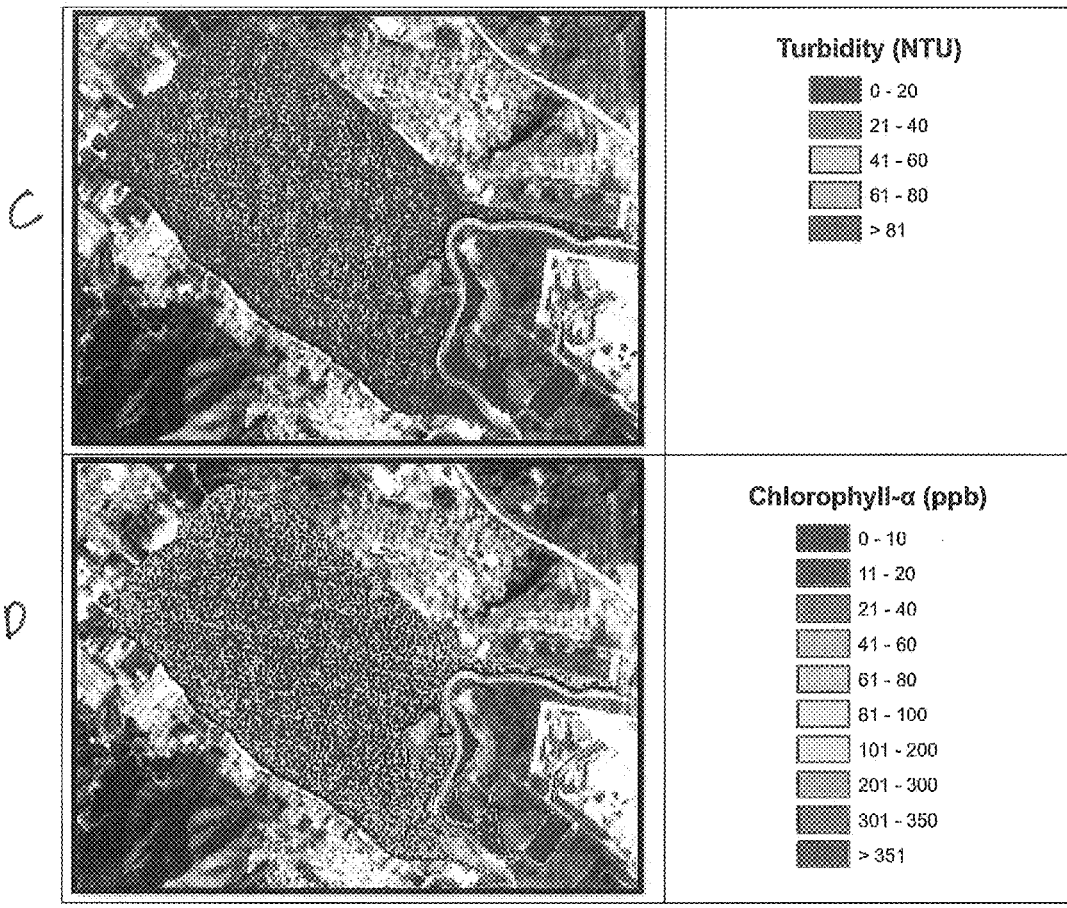
Figure 59:
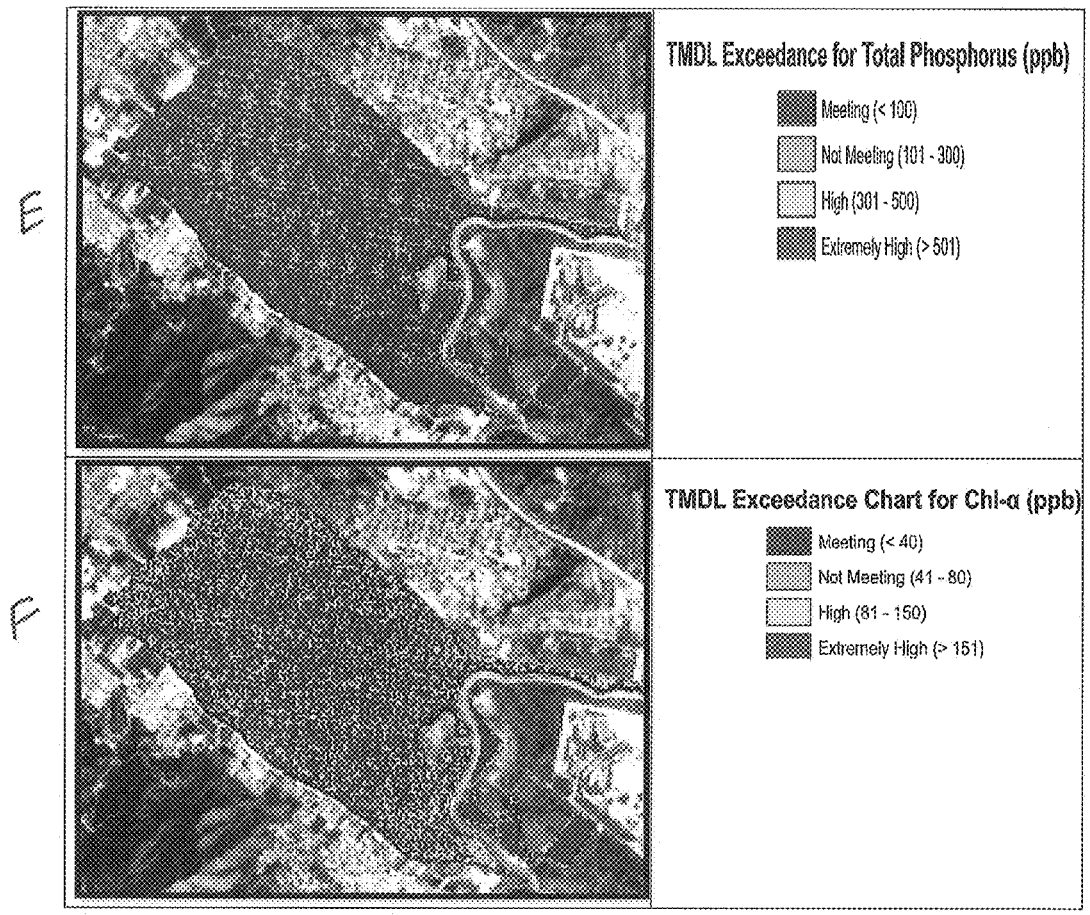
Figure 67:
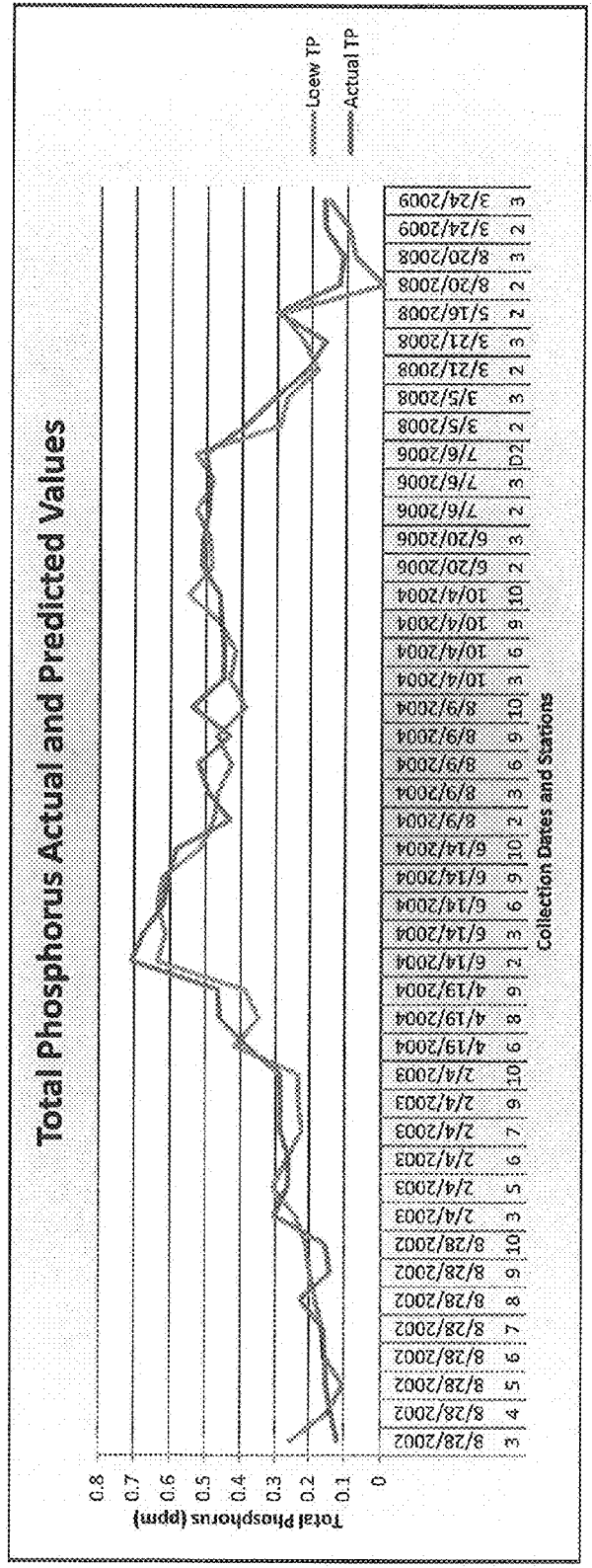
FIG. 67 in Appendix C is a graph representing the actual and predicted values of total phosphorus.
Figure 68:
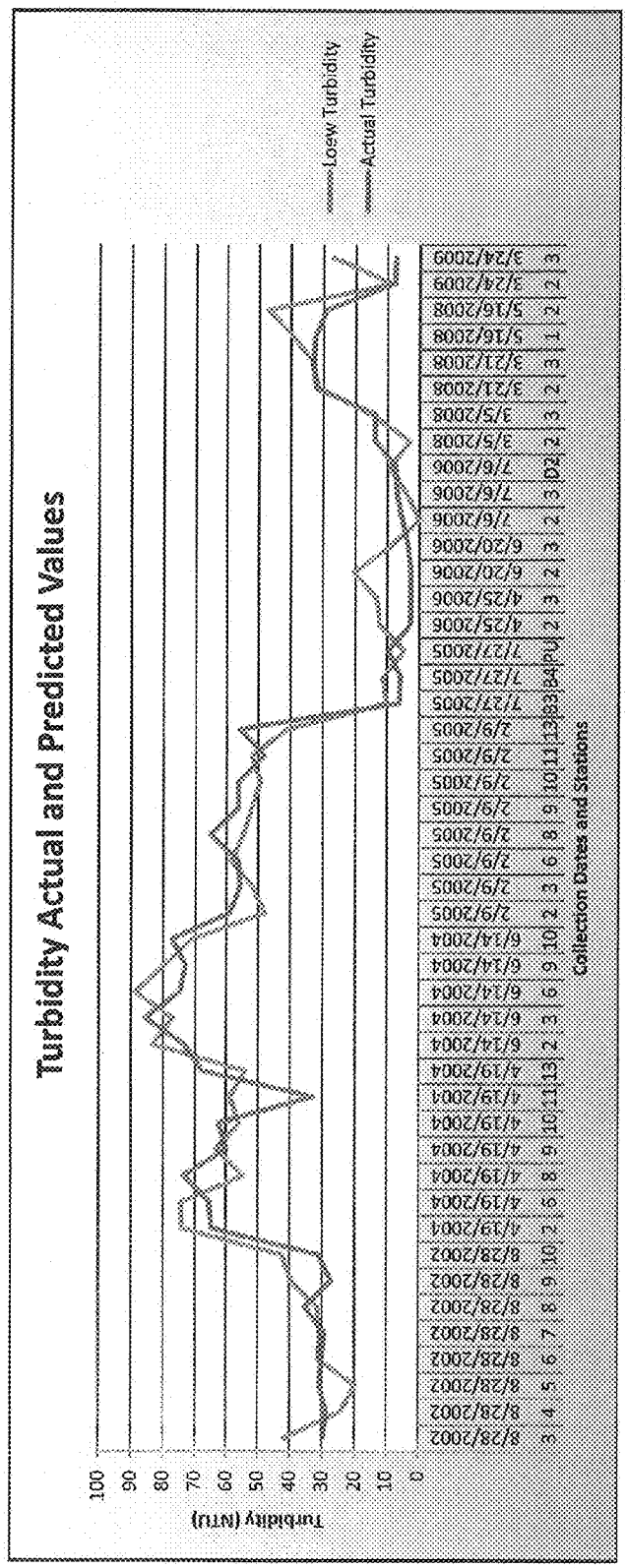
FIG. 68 in Appendix C is a graph representing the actual and predicted values of turbidity.
Figure 69:
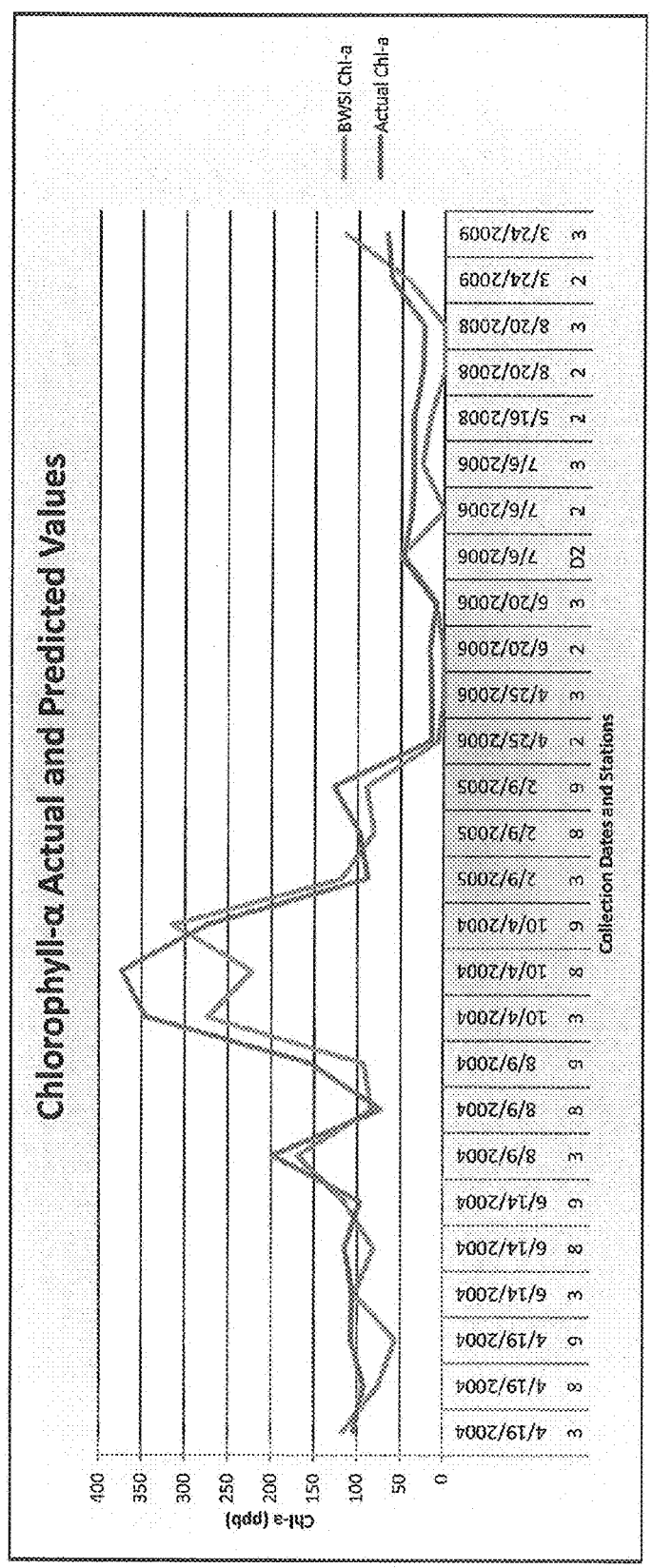
FIG. 69 in Appendix C is a graph representing the actual and predicted values of chlorophyll-α.
Figure 70:
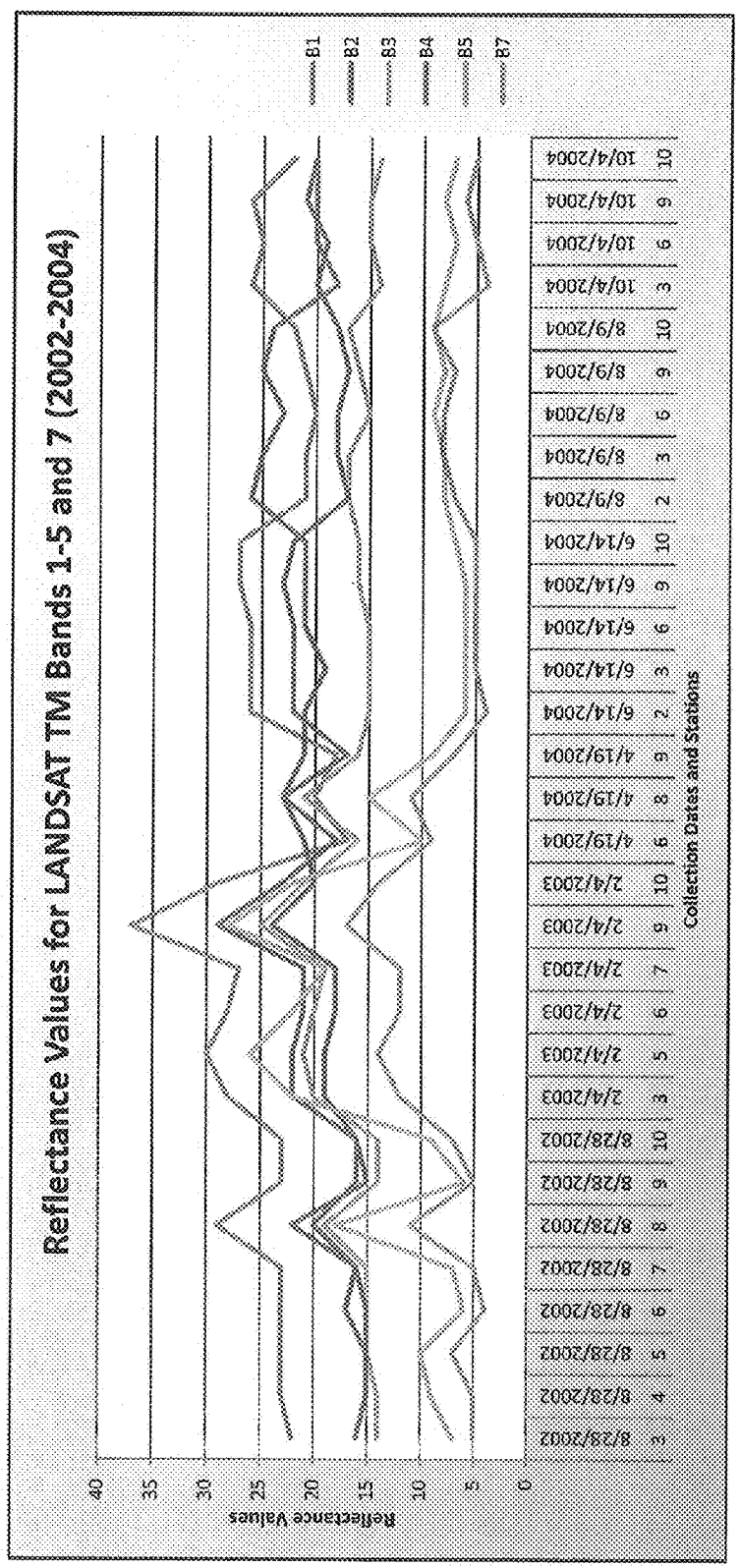
FIG. 70 in Appendix C is a graph representing the reflectance values for LANDSAT TM bands 1-5 and 7 (2002-2004).
Figure 71:
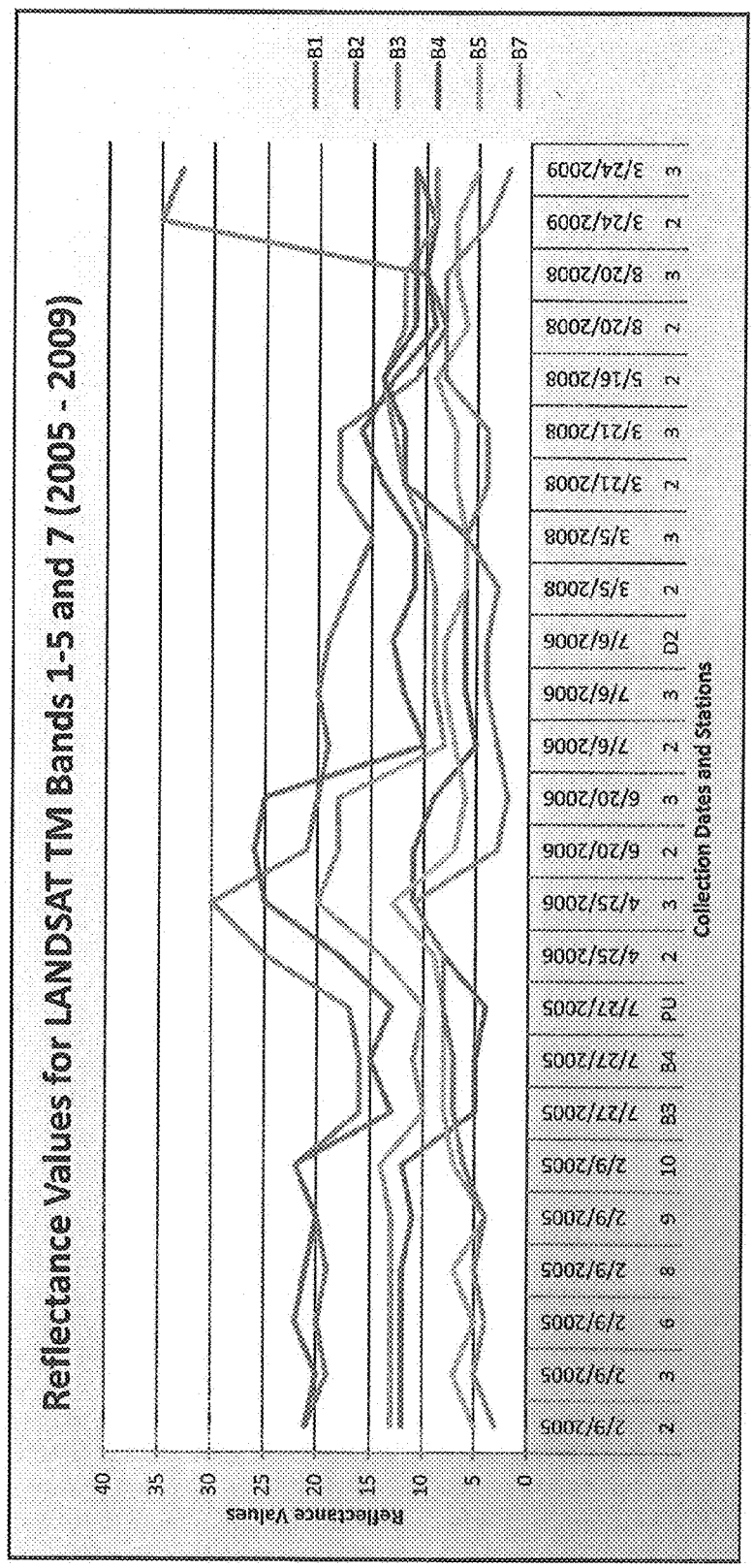
FIG. 71 in Appendix C is a graph representing the reflectance values for LANDSAT TM bands 1-5 and 7 (2005-2009).

The water levels within Lake Elsinore appear to have an effect on the quality, with lower levels affecting the lake negatively. Lake Elsinore is a discontinuous, warm polymictic lake, which are often shallow and subject to strong winds which drives the mixing state the lake is normally in. As discussed earlier, the release of nutrients from bottom sediment can be high, due to dissolved oxygen levels in this region caused by short periods of stratification (Lawson & Anderson, 2007). These winds drive internal loading, mixing the lake and nutrients throughout the water column, and resuspending nutrients that have settled, both of which fuel algal blooms. Within the year 2004 the lake levels were very low (376 meter average), and these images clearly highlighted high total phosphorus levels, turbidity, and algal blooms. The year 2005 brought near record rain fall, raising the lake levels to a maximum (Lawson & Anderson, 2007). Recycled water inputs were used throughout the remainder of the period studied, to keep the lake levels at an optimum level (FIG. 42).

The high bloom phycocyanin model displays phycocyanin levels within the lake to be relatively constant throughout the overpass dates for L7. These levels normally fall around 25 ppb, with a range of 20 to 30 ppb. Some regions of the lake shows what appear to be bigger blooms than others, and these are visible within the turbidity images as well. In a majority of the images the region that is used as a fish habitat, mentioned in the next paragraph, consistently contains larger blooms of cyanobacteria within the phycocyanin images.

Two areas in the south eastern portion of the lake are often colored as "red", indicating the highest levels for each parameter. One of the areas is constructed wetlands, located directly underneath a golf course and an airport. The other is a small channel surrounded by a constructed level that is used as a fish habitat. A small submerged roadway, located at the end of this channel, connects the levee wall to the other side directly across. This channel is blocked on all sides, by the levee walls and roadway, shielding it from wind and wave action. This limits the amount of mixing within this region with the rest of the lake, which is evident in many of the processed images, especially when the water levels are lower.

CONCLUSIONS

In Remote Sensing of the Environment, author and remote sensing scientist John R. Jensen refers to most remote sensing work for creating algorithms to as "local", meaning they are created for one specific location and cannot be transported through space or time. While these local algorithms are obviously still useful, he also calls for the need of "transportable algorithms", which are spatially and temporally invariant and can work anywhere, anytime (Jensen, 2000). About 12 years have passed since this book was written, and while there is an immense lack of studies that focus on ratio algorithms for monitoring water quality, as well as applying these algorithms to different water bodies, what Jensen was hoping for is very possible. The temporal robustness he calls for was proven within this study, as algorithms were applied to withheld data sets that included data from dates and times that were temporally different from the data the algorithm was constructed on. This study also took an algorithm created on an ecoregion completely different than the study site, and applied it to this thesis site's in situ data. While further work needs to be completed to prove the spatial accuracy of this algorithm, the results displayed some hope for these types of spatially robust algorithms. Previous work completed by BWSI involved applying a low range total phosphorus algorithm constructed on Lake Erie (discussed in section 3.2) to in situ data from both Lake Washington (Washington) and Lake Champlain (New Hampshire). The results were strong, with an $R^2$ of 86.1% and a standard error of 0.01 (BWSI, 2010). As long as pre-processing correction methods are applied, and the steps in creating the algorithm are carefully constructed, the creation of spatially and temporally robust algorithms is possible.

The TMDL program desperately needs aid in the measurement and monitoring process of impaired water bodies. Within this thesis two successful algorithms were created to measure total phosphorus and turbidity using satellite remote sensing. The total phosphorus algorithm is dealing with high to very high measurements, and according to trophic classification systems, would be applicable to water bodies that are eutrophic to hypereutrophic (Carlson, 1996). The turbidity algorithm was built on a large range of measurements, and could be successfully applied and tested on a wide range of water bodies concerning their trophic classification. Each algorithm tested, examined, and discussed within this study deals with or is linked to eutrophication and algal blooms. A primary point discussed within this study is the importance of knowing if cyanobacteria are present within a water body that has a nutrient impairment.

Phycocyanin is a pigment nearly unique to this bacterium and can successfully be measured and monitored by satellite remote sensing. Any water body that has a nutrient impairment should not only be monitoring algal blooms by chlorophyll-α, but also by phycocyanin, to determine if harmful algal blooms (HABs) may be present.

Considering that nutrient TMDLs are one the most common TMDL being created, implemented, and monitored, satellite remote sensing and the algorithms within this thesis could especially aid in this specific category of the TMDL program. With the launch of new satellites, advancements in technology, and more resources geared toward using satellites for this purpose, new algorithms and methods of monitoring for various parameters will certainly increase, as will the ways satellite remote sensing can make improvements to the TMDL measurement and monitoring process.

REFERENCES

All references, listed below and elsewhere throughout the description, are hereby incorporated by reference to the extent permitted by applicable law.

Benham, B. & Zeckoski, R. (2007). Lessons learned from TMDL implementation case studies. *Proceedings of the Water Environment Federation*, pp. Volume 15, 428-442.

Blue Water Satellite Inc. Lake Elsinore and Canyon Lake, CA Chlorophyll-a Data Report, 1997-2009, Bowling Green, Ohio, 2010.

Blue Water Satellite Inc. (2010, June). *Mapping total phosphorus concentrations in water bodies using LANDSAT TM and ETM+ data*. Poster presented at the Florida Lakes Management Conference, St. Augustine, Fla.

Bryne, R., Kirby, M., Lund, S., Poulsen, C., & Reidy, L. (2004). Changing sedimentation rates during the last three centuries at lake elsinore, riverside county, California. *Regional Water Quality Board*, 1-49.

Carlson, R. E., and Simpson, J. (1996). A coordinator's guide to volunteer lake monitoring methods. *North American Lake Management Society*. 96 pp.

Copeland, C. (2000). *EPA's Total Maximum Daily Load program: highlights of the final revised rule (CRS report for Congress)*. Washington, D.C.: National Council for Science and the Envirnoment, www.ncseonline.org/nle/crsreports/water/h2o-36.cfm.

Cooper, C. M & Ritchie, J. C. of USDA Agriculture Research Service, *Remote Sensing Techniques for Determining Water Quality: Applications to TMDLs*, Beltsville, Md., 2001.

Diamata, B. N. & Lee, T. C. (1986). Geothermal exploration in the vicinity of lake elsinore, southern California. *Geothermal Resources Council*, Volume 10, 119-123.

Durbin, J. & Watson G. S. (1951) Testing for serial correlation in least squares regression: II. *Biometrica*, Volume 38, 159-178.

Furtak, S & Norton, D. (2009). The TMDL Program Results Analysis Project: New 2008-2009 Products [PowerPoint slides]. www.tmdls.net/docs/DougSarahEPA.pdf Gons, H. J., Peters, S. W. M., & Simis, S. G. H. (2005). Remote sensing of cyanobacterial pigment phycocyanin in turbid inland water. *Limnology and Oceanography*, Volume 50 (1), 237-245.

Govender, M, Chetty, K. & Bulcck, H. (2006). A review of hyperspectral remote sensing and its application in vegetation and water resource studies. *Water SA*, Volume 33 (2), 145-152.

Hadjimitsis, D. G. & Clayton, Chris. (2011). Field spectroscopy for assisting water quality monitoring and assessment in water treatment reservoirs using atmospheric corrected satellite remotely sensed imagery. *Remote Sensing*, Volume 3, 362-377.

Hull, A. G. & Nicolson, C. (1992). Seismotectonics of the northern elsinore fault zone, southern California. *Bulletin of the Seismological Society of America*, Volume 82 (2), 800-818.

Ingraham, C. A. & Ingraham, J. L. *Introduction to Microbiology*. Pacific Grove, Calif.: Brooks/Cole Publishers, 2000.

Jensen, J. R. *Remote Sensing of the Environment*. Upper Saddle River, N.J.: Prentice Hall, 2000.

Kirby, M. E., Lund, S. P., & Poulsen, C. J. (2004). Hydrologic variability and the onset of the modern el niño-southern oscillation: a 19 250-year record from lake elsinore, southern California. *Journal of Quaternary Science*, Volume 20, 239-254.

Lake Elsinore and San Jacinto Watersheds Authority. *Lake Elisnore and Canyon Lake Nutrient TMDL Monitoring Plan*, Santa Ana, Calif., 2006.

Lake Elsinore and Canyon Lake Nutrient TMDL Task Force, *Lake Elsinore & Canyon Lake Nutrient TMDL Annual Water Quality Report*, Santa Ana, Calif., 2010.

Lawson, R. & Anderson, M. A. (2007). Stratification and mixing in Lake Elsinore, California: an assessment of axial flow pumps for improving water quality in a shallow eutrophic lake. *Water Research*, Volume 41, 4457-4467.

Lebowitz, P. J. (2001). Land use, land abuse, and land re-use: a framework for the implementation of TMDLs for nonpoint source polluted waterbodies. *Pace Environmental Law Review*, Volume 19 (1), 97-133.

Li, X. (California Regional Water Quality Control Board: Santa Ana Region). *Lake Elsinore and Canyon Lake Nutrient Total Maximum Daily Loads*, Santa Ana, Calif., 2004.

Mann Jr., J. F. (1951). The sediments of lake elsinore, riverside county, California. *Journal of Sedimentary Petrology*, Volume 21 (3), 151-161.

Mann Jr., J. F. (1956). The origin of elsinore lake basin. *Southern California Academy of Sciences Bulletin*, Volume 55 (2), 71-79.

Merchant, Linda, Ohio EPA, personal communication, November 2010.

MINITAB Statistical Software Version 15, State College, Pa.: MINITAB Inc: 2007-2008.

Oza, H. I. (2003). Nutrient levels and phytoplankton abundance in canyon lake and elsinore, California. *University of California, Riverside*; Master of Science thesis.

U.S. EPA. (1999). *Draft Guidance for Water Quality-based Decisions: The TMDL Process (Second Edition)*, Washington, D.C. www.epa.gov/owow/tmdl/propguid/tmdl-guid.pdf.

U.S. EPA. (2011). *Ecoregions of North America*. Washington, D.C.

U.S. EPA. National Lakes Assessment: A Collaborative Survey of the Nation's Lakes; http://www.epa.gov/owow/LAKES/lakessurvey/pdf/nla_report_low_res.pdf, 2009.

U.S. EPA. (2012). *National summary of impaired waters and TMDL information*. Washington, D.C.

U.S. EPA. (2000). *Nutrient Criteria Technical Guidance Manual: Lakes and Reservoirs* (1$^{st}$ ed.), Washington, D.C. www.epa.gov/waterscience/standards/lakenut2.pdf U.S. EPA. (2003). *Strategy for Water Quality Standards and Criteria*, Washington, D.C. www.water.epa.gov/scitech/swguidance/standards/strategy/upload/2003_08_28_standards_strategy_final.pdf.

U.S. EPA. Using Chemical Data as Indicators of Water Quality http://waterepa.gov/type/watersheds/monitoring/upload/2003_07_02_monitoring_calm_calm_ch4.pdf, 2002.

Vincent, R. K. (2009) *Final Technical Report for NOAA Award #NA080AR4600909 Monitoring of Lake Erie Water Quality with Remote Sensing Oct.* 8, 2008 *through Sep.* 30, 2009, Bowling Green State University.

Vincent, R. K. *Fundamentals of Geological and Environmental Remote Sensing*, Upper Saddle River, N.J.: Prentice Hall, 1997.

Vincent, R. K. (2010) Remote sensing of environmental insults with characteristic spectral features, Presented at Art, Science, and Applications of Reflectance Spectroscopy Symposium, Feb. 23-25, 2010, Boulder, Colo.

Vincent, R. K., Quinn, X., & McKay, R., Miner, J., Czajkowski, K., Savino, J., & Bridgeman, T. (2004). Phycocyanin detection from LANDSAT TM data for mapping cyanobacterial blooms in lake erie. *Remote Sensing of the Environment*, Volume 89 (3), 381-392.

Virginia Tech: The Center for TMDL and Watershed Studiess. (2006). *TMDL Implementation—Characteristics of Successful Projects: Final Report*, Virginia Tech. www.b-se.vt.edu.

Wicks, J. W. (2011). Calibrating Landsat-5 to Landsat-7 spectral band values: empirically derived estimates from matched sets of image pairs. *Lake Erie Water Quality Research Project*.

Younos, T. *Total Maximum Daily Loads: Approaches & Challenges*, Tulsa, Okla.: PennWell Corporation, 2005.

In accordance with the provisions of the patent statutes, the present invention has been described in what is considered to represent its preferred embodiments. However, it should be noted that the invention can be practiced otherwise than as specifically illustrated and described without departing from its spirit or scope.

What is claimed:

1. A method of determining the amount of total phosphate in a body of water from light reflected therefrom, said method comprising the steps of:
   a. using a light measuring device to obtain a measurement of reflected light from said body of water, said measurement comprising a measurement of respective amounts of light in at least five wavelength ranges; and
   b. using a processor to determine the amount of said total phosphate from said respective amounts of light by applying an algorithm relating said respective amounts of light in said wavelength ranges to said amount of said total phosphate in said body of water, wherein said algorithm comprises a quantitative relationship between: (i) the ratio of the amount of light in a first of the wavelength ranges to the amount of light in a second of the wavelength ranges, (ii) the ratio of the amount of light in a third of the wavelength ranges to the amount of light in the first of the wavelength ranges, (iii) the ratio of the amount of light in a fourth of the wavelength ranges to the amount of light in the first of the wavelength ranges, (iv) the ratio amount of light in a fifth of the wavelength ranges to the amount of light in the first of the wavelength ranges, (v) the ratio of the amount of light in a fifth of the wavelength ranges to the amount of light in the third of the wavelength ranges, and (vi) the ratio of the amount of light in the fifth of the wavelength ranges to the amount of light in the fourth of the wavelength ranges, and the amount of the total phosphate in a body of water.

2. A method according to claim 1 wherein said at least five wavelength ranges comprise the measurement, respectively, of: (i) LANDSAT TM band 1, (ii) LANDSAT TM band 2, (iii) LANDSAT TM band 3, (iv) LANDSAT TM band 4, and (v) LANDSAT TM band 5.

3. A method according to claim 1 wherein said at least five wavelength ranges comprise the measurement, respectively, of: (i) from about 0.45 µm to about 0.52 µm, (ii) from about 0.52 µm to about 0.61 µm, (iii) from about 0.63 µm to about 0.69 µm, (iv) from about 0.76 µm to about 0.9 µm, and (v) from about 1.55 µm to about 1.75 µm.

4. A method according to claim 1 wherein said algorithm comprises a measurement of the respective amounts of light in (i) LANDSAT TM band 1, (ii) LANDSAT TM band 2, (iii) LANDSAT TM band 3, (iv) LANDSAT TM band 4, and (v) LANDSAT TM band 5, and wherein said algorithm comprises a quantitative relationship between the sum of the following ratios:
   (a) the reflectance in LANDSAT TM band 2 divided by the reflectance in LANDSAT TM band 1, after subtraction of the reflectance of atmospheric haze separately in each band;
   (b) the reflectance in LANDSAT TM band 3 divided by the reflectance in LANDSAT TM band 2, after subtraction of the reflectance of atmospheric haze separately in each band;
   (c) the reflectance in LANDSAT TM band 4 divided by the reflectance in LANDSAT TM band 2, after subtraction of the reflectance of atmospheric haze separately in each band;
   (d) the reflectance in LANDSAT TM band 5 divided by the reflectance in LANDSAT TM band 2, after subtraction of the reflectance of atmospheric haze separately in each band;
   (e) the reflectance in LANDSAT TM band 5 divided by the reflectance in LANDSAT TM band 3, after subtraction of the reflectance of atmospheric haze separately in each band; and
   (f) the reflectance in LANDSAT TM band 5 divided by the reflectance in LANDSAT TM band 4, after subtraction of the reflectance of atmospheric haze separately in each band.

5. A method according to claim 1 wherein said algorithm is $TP=1.14+0.385*R21-3.16*R32+1.72*R42+1.88*R52-3.52*R53+1.87*R54$, wherein:
   (i) TP is the approximate amount of total phosphate expressed in parts per million or milligrams of phosphate per liter of water;
   (ii) R21 is the value of LANDSAT TM band 2 divided by LANDSAT TM band 1, after subtraction for atmospheric haze separately in each band;
   (iii) R32 is the value of LANDSAT TM band 3 divided by LANDSAT TM band 2, after subtraction for atmospheric haze separately in each band;
   (iv) R42 is the value of LANDSAT TM band 4 divided by LANDSAT TM band 2, after subtraction for atmospheric haze separately in each band;
   (v) R52 is the value of LANDSAT TM band 5 divided by LANDSAT TM band 2, after subtraction for atmospheric haze separately in each band;
   (vi) R53 is the value of LANDSAT TM band 5 divided by LANDSAT TM band 3, after subtraction for atmospheric haze separately in each band; and
   (vii) R54 is the value of LANDSAT TM band 5 divided by LANDSAT TM band 4, after subtraction for atmospheric haze separately in each band.

6. A method according to claim 1 additionally comprising the step of generating a report of said approximate amount of said total phosphate in water.

7. A method according to claim 1 wherein said measurement of reflected light is obtained using a light measurement device selected from the group consisting of a photosensor, camera, digital camera and video camera.

8. A method according to claim 1 wherein said measurement takes place at a first site and said determination takes place at a second site remote from said first site.

9. A method according to claim 1 wherein said at least five wavelength ranges are all in the visible and infrared ranges.

10. A method according to claim 1 wherein the determined amount of said total phosphate in said body of water correlates to the actual amount of said total phosphate in said body of water by a correlation value in excess of 70%.

11. A method according to claim 1 wherein the determined amount of said total phosphate in said body of water correlates to the actual amount of said total phosphate in said body of water by a correlation value in excess of 80%.

12. A method according to claim 1 additionally comprising the step of transmitting data relating to said total phosphate in said body of water to a site remote from the site where said measurement takes place.

13. A method of determining the presence of phosphate in water from light reflected therefrom, said method comprising the steps of:
  a. using a light measuring device to obtain a measurement of reflected light from said water, said measurement comprising a measurement of the respective amount of light in at least five wavelength ranges comprising, respectively: (i) LANDSAT TM band 1, (ii) LANDSAT TM band 2, (iii) LANDSAT TM band 3, (iv) LANDSAT TM band 4, and (v) LANDSAT TM band 5;
  b. using a processor to relate the approximate amount of said total phosphate in said water to said respective amount of light by applying an algorithm relating said respective amount of light in said at least five wavelength ranges to the amount of total phosphate in said water, wherein said algorithm is: TP=1.14+0.385*R21−3.16*R32+1.72*R42+1.88*R52−3.52*R53+1.87*R54, wherein:
  (i) TP is the approximate amount of total phosphate expressed in parts per million or milligrams of phosphate per liter of water;
  (ii) R21 is the value of LANDSAT TM band 2 divided by LANDSAT TM band 1, after subtraction for atmospheric haze separately in each band;
  (iii) R32 is the value of LANDSAT TM band 3 divided by LANDSAT TM band 2, after subtraction for atmospheric haze separately in each band;
  (iv) R42 is the value of LANDSAT TM band 4 divided by LANDSAT TM band 2, after subtraction for atmospheric haze separately in each band;
  (v) R52 is the value of LANDSAT TM band 5 divided by LANDSAT TM band 2, after subtraction for atmospheric haze separately in each band;
  (vi) R53 is the value of LANDSAT TM band 5 divided by LANDSAT TM band 3, after subtraction for atmospheric haze separately in each band; and
  (vii) R54 is the value of LANDSAT TM band 5 divided by LANDSAT TM band 4, after subtraction for atmospheric haze separately in each band.

14. A method according to claim 13 additionally comprising the step of generating a report of said approximate amount of said total phosphate in water.

15. A method according to claim 13 wherein said measurement of reflected light is obtained using a light measurement device selected from the group consisting of a photosensor, camera, digital camera and video camera.

16. A method according to claim 13 wherein said measurement takes place at a first site and said determination takes place at a second site remote from said first site.

17. A method according to claim 13 wherein said at least five wavelength ranges are all in the visible and infrared ranges.

18. A method according to claim 13 wherein the determined amount of said total phosphate in said body of water correlates to the actual amount of said total phosphate in said body of water by a correlation value in excess of 70%.

19. A method according to claim 13 wherein the determined amount of said total phosphate in said body of water correlates to the actual amount of said total phosphate in said body of water by a correlation value in excess of 80%.

20. A method according to claim 13 additionally comprising the step of transmitting data relating to said total phosphate in said body of water to a site remote from the site where said measurement takes place.

21. A method of determining the amount of total phosphate in a body of water from light reflected therefrom, said method comprising the steps of:
  a. using a light measuring device to obtain a measurement of reflected light from said body of water, said measurement comprising a measurement of respective amounts of light in at least five wavelength ranges (i) from about 0.45 μm to about 0.52 μm, (ii) from about 0.52 μm to about 0.61 μm, (iii) from about 0.63 μm to about 0.69 μm, (iv) from about 0.76 μm to about 0.9 μm, and (v) from about 1.55 μm to about 1.75 μm;
  b. using a processor to determine the approximate amount of total phosphate in water from said respective amount of light of light by applying an algorithm relating said respective amounts of light in said at least five wavelength ranges to the amount of total phosphate in said water, wherein said algorithm comprises a quantitative relationship between: (i) the ratio of the amount of light in a first of the wavelength ranges to the amount of light in a second of the wavelength ranges, (ii) the ratio of the amount of light in a third of the wavelength ranges to the amount of light in the first of the wavelength ranges, (iii) the ratio of the amount of light in a fourth of the wavelength ranges to the amount of light in the first of the wavelength ranges, (iv) the ratio amount of light in a fifth of the wavelength ranges to the amount of light in the first of the wavelength ranges, (v) the ratio of the amount of light in a fifth of the wavelength ranges to the amount of light in the third of the wavelength ranges, and (vi) the ratio of the amount of light in the fifth of the wavelength ranges to the amount of light in the fourth of the wavelength ranges, and the amount of the total phosphate in a body of water.

22. A system for determining the amount of total phosphate in a body of water from light reflected therefrom, said system comprising:
  a. a measurement device adapted to obtain a measurement of reflected light from said body of water, said measurement comprising a measurement of respective amounts of light in at least five wavelength ranges; and
  b. a processor capable of determining the amount of said total phosphate from said respective amounts of light by applying an algorithm relating said respective amounts of light in said wavelength ranges to said amount of said total phosphate in said body of water, wherein said algorithm comprises a quantitative relationship between: (i) the ratio of the amount of light in a first of the wavelength ranges to the amount of light in a second of the wavelength ranges, (ii) the ratio of the amount of light in a third of the wavelength ranges to the amount of light in the first of the wavelength ranges, (iii) the ratio of the amount of light in a fourth of the wavelength ranges to the amount of light in the first of the wavelength ranges, (iv) the ratio amount of light in a fifth of the wavelength ranges to the amount of light in the first of the wavelength ranges, (v) the ratio of the amount of light in a fifth of the wavelength ranges to the amount of light in the third of the wavelength ranges, and (vi) the ratio of the amount of light in the fifth of the wavelength ranges to the amount of light in the fourth of the wavelength ranges, and the amount of the total phosphate in a body of water.

23. A system according to claim 22 wherein said at least five wavelength ranges comprise the measurement, respectively, of: (i) LANDSAT TM band 1, (ii) LANDSAT TM band 2, (iii) LANDSAT TM band 3, (iv) LANDSAT TM band 4, and (v) LANDSAT TM band 5.

24. A system according to claim 22 wherein said at least five wavelength ranges comprise the measurement, respectively, of: (i) from about 0.45 µm to about 0.52 µm, (ii) from about 0.52 µm to about 0.61 µm, (iii) from about 0.63 µm to about 0.69 µm, (iv) from about 0.76 µm to about 0.9 µm, and (v) from about 1.55 µm to about 1.75 µm.

25. A system according to claim 22 wherein said algorithm comprises a measurement of the respective amounts of light in (i) LANDSAT TM band 1, (ii) LANDSAT TM band 2, (iii) LANDSAT TM band 3, (iv) LANDSAT TM band 4, and (v) LANDSAT TM band 5, and wherein said algorithm comprises a quantitative relationship between the sum of the following ratios:
    (a) the reflectance in LANDSAT TM band 2 divided by the reflectance in LANDSAT TM band 1, after subtraction of the reflectance of atmospheric haze separately in each band;
    (b) the reflectance in LANDSAT TM band 3 divided by the reflectance in LANDSAT TM band 2, after subtraction of the reflectance of atmospheric haze separately in each band;
    (c) the reflectance in LANDSAT TM band 4 divided by the reflectance in LANDSAT TM band 2, after subtraction of the reflectance of atmospheric haze separately in each band;
    (d) the reflectance in LANDSAT TM band 5 divided by the reflectance in LANDSAT TM band 2, after subtraction of the reflectance of atmospheric haze separately in each band;
    (e) the reflectance in LANDSAT TM band 5 divided by the reflectance in LANDSAT TM band 3, after subtraction of the reflectance of atmospheric haze separately in each band; and
    (f) the reflectance in LANDSAT TM band 5 divided by the reflectance in LANDSAT TM band 4, after subtraction of the reflectance of atmospheric haze separately in each band.

26. A system according to claim 22 wherein said algorithm is $TP=1.14+0.385*R21-3.16*R32+1.72*R42+1.88*R52-3.52*R53+1.87*R54$, wherein:
    (i) TP is the approximate amount of total phosphate expressed in parts per million or milligrams of phosphate per liter of water;
    (ii) R21 is the value of LANDSAT TM band 2 divided by LANDSAT TM band 1, after subtraction for atmospheric haze separately in each band;
    (iii) R32 is the value of LANDSAT TM band 3 divided by LANDSAT TM band 2, after subtraction for atmospheric haze separately in each band;
    (iv) R42 is the value of LANDSAT TM band 4 divided by LANDSAT TM band 2, after subtraction for atmospheric haze separately in each band;
    (v) R52 is the value of LANDSAT TM band 5 divided by LANDSAT TM band 2, after subtraction for atmospheric haze separately in each band;
    (vi) R53 is the value of LANDSAT TM band 5 divided by LANDSAT TM band 3, after subtraction for atmospheric haze separately in each band; and
    (vii) R54 is the value of LANDSAT TM band 5 divided by LANDSAT TM band 4, after subtraction for atmospheric haze separately in each band.

27. A system according to claim 22 additionally comprising the step of generating a report of said approximate amount of said total phosphate in water.

28. A system according to claim 22 wherein said measurement of reflected light is obtained using a light measurement device selected from the group consisting of a photosensor, camera, digital camera and video camera.

29. A system according to claim 22 wherein said measurement takes place at a first site and said determination takes place at a second site remote from said first site.

30. A system according to claim 22 wherein said at least five wavelength ranges are all in the visible and infrared ranges.

31. A system according to claim 22 wherein the determined amount of said total phosphate in said body of water correlates to the actual amount of said total phosphate in said body of water by a correlation value in excess of 70%.

32. A system according to claim 22 wherein the determined amount of said total phosphate in said body of water correlates to the actual amount of said total phosphate in said body of water by a correlation value in excess of 80%.

33. A system according to claim 22 additionally comprising the step of transmitting data relating to said total phosphate in said body of water to a site remote from the site where said measurement takes place.

34. A system for determining the presence of total phosphate in water from light reflected therefrom, said system comprising:
    a. A measurement device adapted to obtain a measurement of reflected light from said water, said measurement comprising a measurement of the respective amount of light in at least five wavelength ranges comprising, respectively: (i) LANDSAT TM band 1, (ii) LANDSAT TM band 2, (iii) LANDSAT TM band 3, (iv) LANDSAT TM band 4, and (v) LANDSAT TM band 5;
    b. A processor capable of determining the approximate amount of said total phosphate in said water to said respective amount of light by applying an algorithm relating said respective amount of light in said at least five wavelength ranges to the amount of total phosphate in said water, wherein said algorithm is: $TP=1.14+0.385*R21-3.16*R32+1.72*R42+1.88*R52-3.52*R53+1.87*R54$, wherein:
        (i) TP is the approximate amount of total phosphate expressed in parts per million or milligrams of phosphate per liter of water;

(ii) R21 is the value of LANDSAT TM band 2 divided by LANDSAT TM band 1, after subtraction for atmospheric haze separately in each band;

(iii) R32 is the value of LANDSAT TM band 3 divided by LANDSAT TM band 2, after subtraction for atmospheric haze separately in each band;

(iv) R42 is the value of LANDSAT TM band 4 divided by LANDSAT TM band 2, after subtraction for atmospheric haze separately in each band;

(v) R52 is the value of LANDSAT TM band 5 divided by LANDSAT TM band 2, after subtraction for atmospheric haze separately in each band;

(vi) R53 is the value of LANDSAT TM band 5 divided by LANDSAT TM band 3, after subtraction for atmospheric haze separately in each band; and (vii) R54 is the value of LANDSAT TM band 5 divided by LANDSAT TM band 4, after subtraction for atmospheric haze separately in each band.

35. A system according to claim 34 additionally comprising the step of generating a report of said approximate amount of said total phosphate in water.

36. A system according to claim 34 wherein said measurement of reflected light is obtained using a light measurement device selected from the group consisting of a photosensor, camera, digital camera and video camera.

37. A system according to claim 34 wherein said measurement takes place at a first site and said determination takes place at a second site remote from said first site.

38. A system according to claim 34 wherein said at least five wavelength ranges are all in the visible and infrared ranges.

39. A system according to claim 34 wherein the determined amount of said total phosphate in said body of water correlates to the actual amount of said total phosphate in said body of water by a correlation value in excess of 70%.

40. A system according to claim 34 wherein the determined amount of said total phosphate in said body of water correlates to the actual amount of said total phosphate in said body of water by a correlation value in excess of 80%.

41. A system according to claim 34 additionally comprising the step of transmitting data relating to said total phosphate in said body of water to a site remote from the site where said measurement takes place.

42. A system for determining the amount of total phosphate in a body of water from light reflected therefrom, said system comprising:

a. a measurement device adapted to obtain a measurement of reflected light from said body of water, said measurement comprising a measurement of respective amounts of light in at least five wavelength ranges: (i) from about 0.45 µm to about 0.52 µm, (ii) from about 0.52 µm to about 0.61 µm, (iii) from about 0.63 µm to about 0.69 µm, (iv) from about 0.76 µm to about 0.9 µm, and (v) from about 1.55 µm to about 1.75 µm;

b. a processor capable of determining the approximate amount of total phosphate in water from said respective amount of light of light by applying an algorithm relating said respective amounts of light in said at least five wavelength ranges to the amount of total phosphate in said water, wherein said algorithm comprises a quantitative relationship between: (i) the ratio of the amount of light in a first of the wavelength ranges to the amount of light in a second of the wavelength ranges, (ii) the ratio of the amount of light in a third of the wavelength ranges to the amount of light in the first of the wavelength ranges, (iii) the ratio of the amount of light in a fourth of the wavelength ranges to the amount of light in the first of the wavelength ranges, (iv) the ratio amount of light in a fifth of the wavelength ranges to the amount of light in the first of the wavelength ranges, (v) the ratio of the amount of light in a fifth of the wavelength ranges to the amount of light in the third of the wavelength ranges, and (vi) the ratio of the amount of light in the fifth of the wavelength ranges to the amount of light in the fourth of the wavelength ranges, and the amount of the total phosphate in a body of water.

* * * * *